US007398279B2

(12) United States Patent
Muno, Jr. et al.

(10) Patent No.: US 7,398,279 B2
(45) Date of Patent: Jul. 8, 2008

(54) METHOD, ROUTINES AND SYSTEM FOR IDENTIFICATION OF IMPRINTS ON DOSAGE FORMS

(75) Inventors: Francis J. Muno, Jr., 5N021 Munger Rd., Wayne, IL (US) 60184-2484; Douglas C. McKalip, Tinley Park, IL (US)

(73) Assignee: Francis J. Muno, Jr., Wayne, IL (US)

( * ) Notice: Subject to any disclaimer, the term of this patent is extended or adjusted under 35 U.S.C. 154(b) by 560 days.

(21) Appl. No.: 10/185,538

(22) Filed: Jun. 28, 2002

(65) Prior Publication Data

US 2004/0054639 A1 Mar. 18, 2004

(51) Int. Cl.
*G06F 7/00* (2006.01)
(52) U.S. Cl. .................................... 707/104.1
(58) Field of Classification Search .............. 707/1, 707/3, 6, 104.1, 100, 102, 10; 382/181, 229; 705/1, 26, 40
See application file for complete search history.

(56) References Cited

U.S. PATENT DOCUMENTS

| | | | | | |
|---|---|---|---|---|---|
| 4,289,958 | A | * | 9/1981 | Thomas | 235/489 |
| 5,700,998 | A | * | 12/1997 | Palti | 235/375 |
| 5,845,264 | A | * | 12/1998 | Nellhaus | 705/28 |
| 5,928,664 | A | * | 7/1999 | Yang et al. | 424/440 |
| 5,992,742 | A | * | 11/1999 | Sullivan et al. | 235/462.01 |
| 6,025,984 | A | * | 2/2000 | Borkowski | 361/679 |
| 6,496,836 | B1 | * | 12/2002 | Ronchi et al. | 707/104.1 |
| 6,542,902 | B2 | * | 4/2003 | Dulong et al. | 707/104.1 |
| 6,543,692 | B1 | * | 4/2003 | Nellhaus et al. | 235/462.01 |
| 6,778,994 | B2 | * | 8/2004 | Gogolak | 707/102 |
| 2003/0233195 | A1 | * | 12/2003 | Johnson et al. | |

OTHER PUBLICATIONS

First Databank Announces Release of Version 2 of Drug Image Database (TM) and Drug Imprint Database(TM). Apr. 5, 2000, Newswire, Gale Group.*
The Internet Drug Index, Aug. 8, 2001,web.archive.org/web/20010801153921/www.rxlist.com/interact.htm.*
Physicians' Desk Reference, Edition 56, 2002, Medical Economics Company, p. 303-304,309,311,505,507,516,1108,1301.*
Caldwell, J. et al, "Identification of Drugs" *The Journal of the American Medical Association*, vol. 187, No. 12, pp. 161-163.
Clinical Pharmacology, www.gsm.com.
Drug Identification Bible, www.drugidbible.com.
"Editorial: Coded-Imprint Drug Identification" *Northwest Medicine*, vol. 70, pp. 243, 281.
ePocrates, www.epocrates.com.

(Continued)

*Primary Examiner*—Greta L Robinson
(74) *Attorney, Agent, or Firm*—Michael Best & Friedrich LLP

(57) ABSTRACT

The invention includes a user method, routines and system for identifying an imprint on a therapeutic dosage form. The method includes reducing imprints to their basic informational components; grouping the basic informational components into searchable basic informational component group databases; searching the databases in an organized manner; and matching features of the imprint to basic informational components, resulting in a positive identification of the imprint.

18 Claims, 34 Drawing Sheets

OTHER PUBLICATIONS

Ident-a-drug.com, www.identadrug.com.

"Identification Guide for Solid Dosage Forms" *The Journal of the American Medical Association*, vol. 182, No. 12, Dec. 22, 1962, pp. 101-258.

Micromedex, www.micromedex.com.

Muno, F., "Call Our Pharmacist" *Law and Order*, Nov. 1995, p. 50.

Muno, F., "Drug Information Rendered 'Pay-By-Call'" *Journal of Pharmacy Practice*, vol. X, No. 4, Aug. 1997, pp. 286-291.

Muno, Jr., F, "Broadening Utility of Tablet and Capsule Imprints" *Journal of Pharmacy Practice*, vol. XIII, No. 2, Apr. 2000, pp. 130-140.

Physician's Desk Reference, www.pdr.com.

Robertson, W. "Drug-Imprint Coding" *The Journal of the American Medical Association*, vol. 229, No. 7, Aug. 12, 1974, p. 766.

RxList.com, www.rxlist.com.

Ukens, C., "Patient Counseling is just a Telephone Call Away" *Drug Topics*, Jan. 10, 1994, p. 26.

www.drugs.com.

* cited by examiner

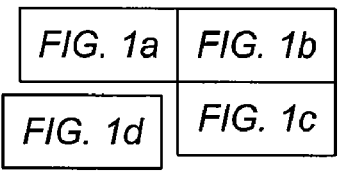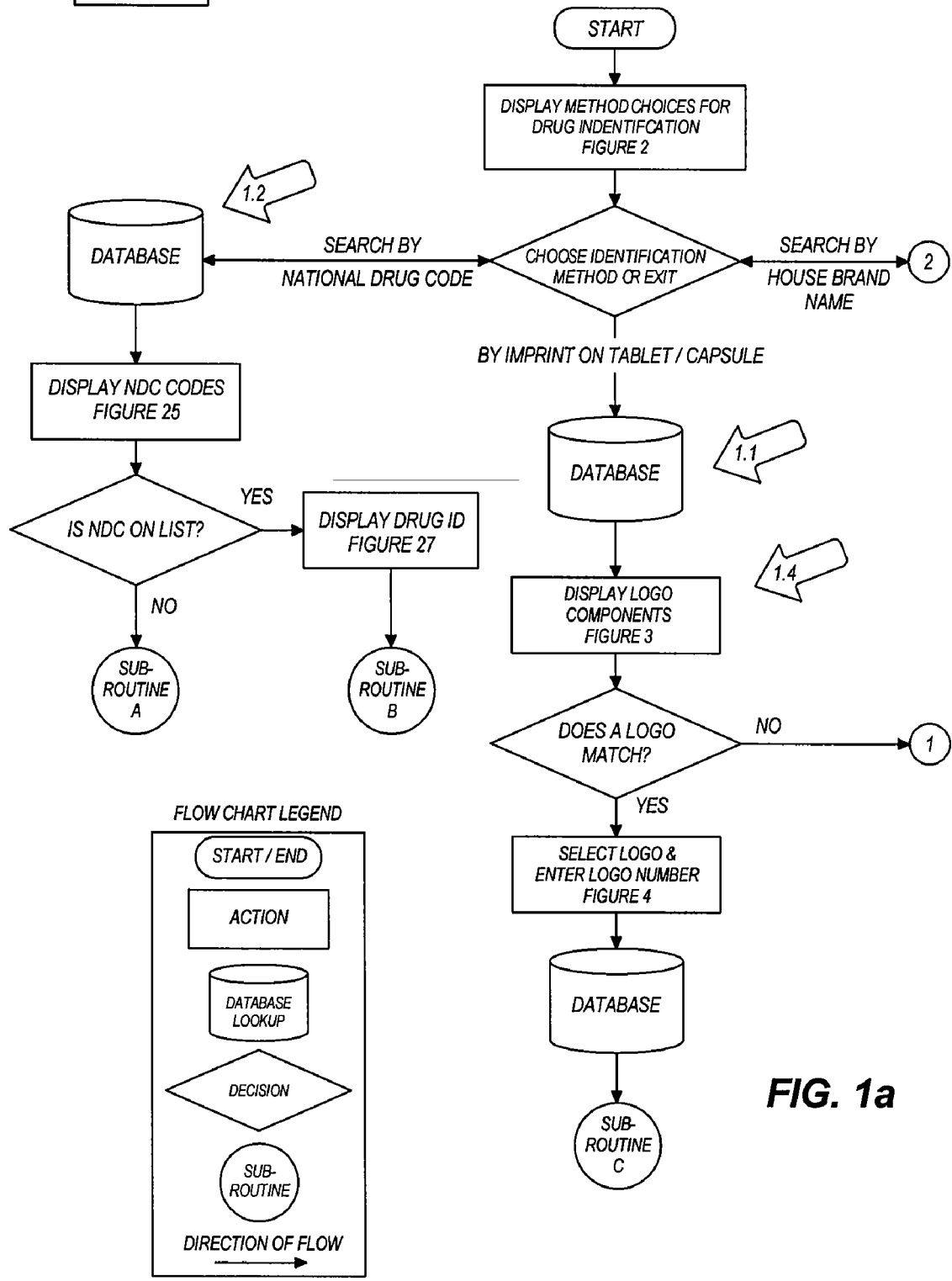

METHOD, ROUTINES AND SYSTEM FOR IDENTIFICATION OF IMPRINTS ON DOSAGE FORMS

BACKGROUND OF THE INVENTION

This invention relates to a method, routines and system for identification of imprints on dosage forms, whether defined by the *United States Pharmacoepia* or not, thereby assisting in the identification of the drug product. In particular, the invention is directed towards dosage forms other than liquids, inhalants and parenterals.

In 1962, the article "Identification Guide for Solid Dosage Forms" by Hefferren et al. (Hefferren, J. J. et al., Identification Guide for Solid Dosage Forms, Journal of the American Medical Association, Dec. 22, 1962), hereinafter the "Guide," described an attempt to identify tablets, capsules and softgels by their size, shape, color and markings for approximately 5000 drug products. The method used physical measurement of size, assignment of the unknown drug product to predetermined shapes, matching color to a standard color reference such as 'paint chips' and markings on dosage forms known within the industry as "imprint." Only a few drug products bore an imprint at that time. The Guide was of particular benefit in emergency rooms and coroners' laboratories because of their need to know and their ability to physically manipulate unknown drug products. However, in the process of identification, the specimen of the drug product was destroyed in many cases. At each step of the decision-tree in the Guide, the user's choices were "narrowed to one or, at most, a relatively few drugs. A tentative identification was thus established.

At that time the state-of-the-art of tablet and capsule identification was primitive by today's standards. Experts, such as forensic scientists, pharmacists and specialists in poison centers could be relied upon to use the Guide, but it had little utility in non-expert hands. The Guide has not been formally maintained and no new products have been cataloged since June 1962.

An effective system to make any physical identification must rely on objective, rather than subjective, information or data points. Size is objective but its measurement is fraught with difficulties—standard tools and methods and their immediate availability are needed in expert hands. However, shape is subjective, as it is difficult at times to describe the overall appearance of a dosage form verbally. The description of a dosage form as oblong, oval or caplet does not provide a definitive description. Similarly, color is subjective. It is difficult to describe the color of a dosage form, as example, such as pink, coral, peach or rose verbally without the use of a color chip.

A survey of the available resources is instructive: no print resource nor existing electronic catalog was or is adequate to fully meet the technical demands of identifying a drug product, by professionals and the public at large. In the current art, both print and electronic resources exclude non-numeric, non-alphabetic information, which leads users to the situation of multiple choices from which to make an identification. Lastly, print resources are dated from the day they are published and rapidly decline in value.

An electronic catalog was copyrighted in 1974. Its methodology presented imprints in text-only format, e.g., 93 150 3 (93=Teva Labs and 150 3 distinguishes it as an acetaminophen 325 mg and codeine 30 mg tablet) even though logos were already a common feature of imprints. Unable to accommodate logos, this catalog increased the possibility of finding an imprint by listing all possible combinations of imprint features but redundancy reduced its ease of use. Burden of these combinations within the catalog soon becomes obvious to the user. Lacking any discriminating routine for attacking imprints, the user has 398 choices from which to make an identification if the feature 93 is used for the initial search, 140 choices if the feature 150 is chosen and 210 choices if the feature 3 is chosen, all of which choices may require the user to assess them individually in order to arrive at a possible identification. Users may also be impeded by the multiplicity of screens needing to be reviewed; as in the exemplary imprint 93 150 3 above, the electronic catalog presents nine or ten screens displaying the multiple records. In another example, the imprint BRA 200 may be identified approaching first the feature BRA then 200 but not by approaching feature 200 and then BRA. After examining a list of 359 possibilities containing the feature 200, the user finds that the feature BRA is absent. In another example, the imprint 230, the user must evaluate 16 records to make a rather simple identification. The electronic catalog presents a multiplicity of choices but makes no definitive declaration of identification for users.

Furthermore, because of the text-only format of the electronic catalog, direct representation of logo features is precluded. The catalog contrives, as an example, the Abbott Laboratories logo with either the capital letter A or E, while a lower-case printed letter 'a' might be a better expression, but still not a direct expression, of the logo itself. Other logos may not lend themselves to such contrivances, consequently expensing valuable information. The user may be left with no direct representation of logo imprint features and at times outright absence of information, all serious deficiencies for a leading reference in the field.

For the above reasons the electronic catalog cannot be definitive in making a positive identification. It follows then that a reasonable strategy for the publisher of the electronic catalog might be to limit its use to experts. In fact, each resultant informational screen bears the legend "All POISONDEX® product information is CONFIDENTIAL, intended for use by healthcare professionals, and may not be released to non-medical personnel."

Lastly, this imprint catalog, initially and for more than a decade afterward, did not include the National Drug Code (NDC) in each record although NDCs were widely in use since the 1960s. Consequently, no search to confirm a drug product by its NDC is currently available. Regardless of its dated features and reflecting the burgeoning drug market, the current electronic catalog has had a market for its more than 30,000 imprints and their combinations, whether they exist or not on a current drug product, for nearly the past three decades.

Recently several websites offer direct searches of databases for imprints on tablets and capsules, specifically www.rxlist.com and identadrug.com. The former site is not easy to use, both lack a comprehensive database of imprints and neither accommodates logo imprint features. More significantly, the former site uses no more technology with which to search for an imprint than a simple 'grep'—input of a string of characters or digits as seen in the imprint, but not logos, leading to the output of multiple records containing the same string somewhere therein and not necessarily related to the imprint itself. At both sites the user is left with making a choice; no definitive declaration of an identification is provided. Their technology is little different from that of the 1974 electronic catalog discussed above.

Yet another database marketed on a CD-ROM disc uses color, shape and scoring as input to its search routines. The routines are difficult to use and the database is incomplete. Again the user is left with choices from a multiplicity of records in order to make the identification. This database has been developed with no more technology than that used by the Guide reported by Hefferren in 1962. If the user misrepresents color, shape or scoring, likely no records will be found and no identification can be made.

A prior art compilation of records for automated database has been developed, containing drug product records of imprint features in text only and associated descriptors. This compilation has the title Readi-TCID©. However, Readi-TCID© does not have nor utilize method and routines for identifying definitively an imprint of dosage forms. The database only displays a collage of imprint logos as found on tablets and capsules in the United States known at the time of development.

U.S. Pat. No. 6,025,984 describes a portable drug information computer. However, the '984 patent is not capable of identifying imprints on dosage forms. Similarly, U.S. Pat. No. 4,289,958 generally relates to a device to take physical measurements and to compare these measurements and shapes to a data set punched into cards. The data set makes no reference to using an imprint as a means of making or confirming an identification of a dosage form. Both patents have the significant drawback that they deal with the least effective means of making an identification today—shape and scoring.

U.S. Pat. Nos. 5,700,998 and 5,845,264 both overlook the current US FDA required imprints on solid dosage forms in certain drug categories and further claim an indicia using bar code that may be applied to the surface of selected dosage forms. Further, pharmacies, hospitals, nursing homes and possibly consumers require specialized equipment to read the indicia whenever and wherever an identification is required for selected dosage forms. Bar code indicia applied to dosage forms is redundant to current practices, cannot be visualized at will by the unaided eye, is far more complex than drug makers' current imprinting methods and may have limited applicability in the case of some solid dosage forms.

All of the previously discussed methods and systems of drug identification have significant drawbacks, relying on technology in use for more than thirty years. It is an object of the present invention to solve these and other problems and to claim the development of new technology in the art of identifying tablets and capsules. The present invention alters no present regulation or production methods and its method and routines are applicable to the unaided eye, readily available computer technology and equipment and any applicable, comprehensive database. The present invention accommodates all dosage forms and all imprint features—both non-numeric and non-alphabetic as well as numeric digits and alphabetic characters—and organizes all imprint features with the goal of the least number of decisions within its routines to arrive at a declarative identification.

Identification of drug products is made by using the common descriptors of the art and associating them with imprint features within an applicable database. First the process involves a method of assigning all, including heretofore unrecognized or unused, imprint features as components within classes in a database. Secondly, routines permit users of the system to compare imprint features, as seen on dosage forms, to database components, presented in a hierarchy of classes and aided by computer programs.

Novel method and routines of the present invention avoid the problems of matching dosage form physical characteristics, of using only partial catalogs or data sets, all of which are significantly devoid of logos and of lacking the cardinal concept: imprints are unique. By method herein, the features of imprints are the sole independent variables and physical characteristics are solely descriptors and dependent variables. The method, routines and system of the present invention are elegant in their simplicity and solve longstanding and intractable problems in the art.

SUMMARY OF THE INVENTION

The invention includes a computer-implemented system of method and routines for identifying definitively imprints of dosage forms, thereby identifying the drug product. Method (1) assesses the imprint on the dosage form for at least one type of feature therein, (2) partitions a plurality of features of imprints into a plurality of respective component class members; (3) assigns each component class member to only one component class, (4) further assigns to each non-numeric, non-alphabetic component class member a unique number within the class and (5) requires the maintenance of the relationship among component class members and respective descriptors of dosage forms bearing the imprint, within the records of an applicable database. The method depends upon the dosage form bearing an imprint.

Routines of the present invention match primary, secondary and tertiary features of the imprint, physically seen or reportedly to be, on an exemplary dosage form to at least one component class. Imprint features are compared by a user to the plurality of logo, numeric, alphabetic and remainder of the code component class members, presented serially by component classes until all features of the imprint are exhausted, thereby obtaining an identification of the imprint on the dosage form. Component class members are correlated one to the other, for the several features of an imprint, in the record of an applicable database, and routines may be typically computer implemented. The dosage form can be selected from a group of dosage forms consisting of a bolus, a capsule, a softgel, an implant, an insert, a lozenge, a tablet, a geltab and a gelcap but not limited to these alone. Component classes are selected from the group consisting of a logo class, a numeric class, an alphabetic class and a remainder of the code class.

In one variant of the invention, at least one of the component class members is selected from the group consisting of a logo component class, a numeric component class, an alphabetic component class and a remainder of the code component class.

In another variant of the invention, the system further includes routine(s) confirming a special descriptor of the identified imprint. The special descriptor is selected from the group consisting of a color descriptor, an opacity descriptor, a scoring descriptor, a shape descriptor, a drug descriptor, a strength descriptor, a dosage form descriptor and a route of administration descriptor.

In yet a further aspect of the invention, the system further includes routines for accessing a database using a computer network. The computer network may include a wireless computer network.

In yet another aspect of the invention, the system includes the step of paying for the identification of an imprint of a dosage form over the computer network. The computer network can be selected from the group consisting of a publicly accessible computer network and a privately accessible computer network. In one variant, the publicly accessible computer network includes the Internet.

In yet another aspect, the invention provides a computer program for identifying an imprint of a dosage form. The computer program includes routines for searching a database having a plurality of component classes. Each of the component classes includes a plurality of component class members. The component classes comprise a respective type of feature of a plurality of imprints. The program also includes a matching routine for matching a feature of the imprint to at least one of the component class members to obtain an identified imprint.

In yet a further aspect, the computer program also includes a routine for confirming a special descriptor of the identified imprint. The special descriptor is selected from the group consisting of a color descriptor, an opacity descriptor, a scoring descriptor, a shape descriptor, a drug descriptor, a strength descriptor, a dosage form descriptor and a route of administration descriptor.

In yet another variant, the invention provides a system utilizing at least one microprocessor or logic circuit controlled device comprising the computer program described above. The microprocessor or logic circuit controlled device is selected from the group consisting of at least all of the following: a personal computer, a notebook computer, a lap top computer, a cellular phone, an electronic device, a two way pager and a server. The server is an Internet server in one variant of the invention.

In yet another aspect, the system also includes a web site accessing routine located on the microprocessor or logic controlled device. The device is selected from the group consisting of a computer, a publicly accessible computer, a private computer network and an Internet server.

In addition to pharmaceutical dosage forms, the system can also provide the identification for other ingested products such as confectioneries. These and other objects of the invention are described below in the various figures and the detailed description of the invention.

BRIEF DESCRIPTION OF THE DRAWINGS

FIGS. 1a, 1b, 1c and 1d illustrate the present invention by way of a flow chart for the computer assisted, inter-related, multi-media routines, files, screens and user options in which the various figures discussed below are related and correlated one to the other; FIG. 1d shows each of the subroutines implemented in FIGS. 1a-1c.

DETAILED DESCRIPTION OF THE INVENTION

Imprints are the markings on dosage forms and are composed of features having the properties of logos, alphabetic characters and numeric digits.

Figure 31:
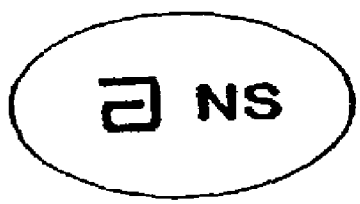
FIG. 31 illustrates four graphic images of exemplary imprints and imprint features.
Figure 31:
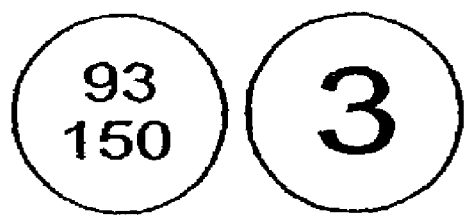
Figure 31:
Figure 31:

In FIG. 31 four such imprints are illustrated by the graphic images 31.1, 31.2, 31.3 and 31.4, of which the first and third images have a combination of feature properties. Imprints are readily observable by individuals and no special competency is required. Imprints were developed initially by some drug makers for their products and then by all in response to United States Food and Drug Administration (US FDA) regulations. The US FDA requires an imprint on drug products for specific classes: controlled substances and prescription drug products and over-the-counter, veterinary and homeopathic products. The drug maker is permitted wide latitude in the specification of features within the imprint. Imprints identify dosage forms and make an identification system possible. Yet no public imprint registry currently exists.

Drug makers understand the advantage of product identification from the perspective of marketing, trade dress and risk management. Typically drug makers use a consistent imprint feature that identifies them as the maker and then assign an added feature which identities the drug products themselves by the brand and generic names, active ingredient(s) and strength, dosage form and formulation.

Maker-specific imprint features may be logos (Abbott Laboratories logo in FIG. 31.1) or a string of digits (93 in FIG. 31.2) or characters (BRA in FIG. 31.3. Maker-specific features derive uniqueness from their establishment in the marketplace and recognition by others.

Product-specific features are typically a string of numeric or alphabetic characters; for a few products the maker has assigned a logo to identify the product.

If the maker-specific feature of an imprint is unique on a drug maker's dosage form and the drug maker further chooses an additional imprint feature unique to it to identify its product, then the combination of the two features makes the imprint unique, not only within the drug maker's catalog, but among all imprints in the marketplace. The product-specific feature without considering the maker-specific feature may not be unique, since product-specific features are arbitrarily chosen and may randomly appear in several product lines. Consequently, alone they cannot lead to a definitive identification.

Method of the present invention posits that imprints on dosage forms are unique. When all imprint features, including features heretofore unrecognized or unused, e.g., logo features, by other workers in the field, are taken into account, definitive identification of drug products becomes possible. Taking all imprint features into account in the present invention is novel with respect to the current state-of-the-art. In fact, using the specifications, method and routines described herein and the database Readi-TCID® a plurality of imprints are solved to only one drug product and the number that do not, by far in the minority, is readily distinguished by further use of its descriptors, e.g., color, shape and scoring. Examples 5, 6 and 7 below so illustrate.

The method assesses imprints for features, assigning features to primary, secondary or tertiary types. The establishment of types of imprint features is a novelty in the present invention and is hitherto unknown in the art. The partitioning of imprints by feature types significantly reduces the number of drug products which need to be considered in order to make a positive identification, increases the efficiency of the several search routines discussed below and further leads to a declarative result. A "primary" imprint feature is one that identifies the maker of the drug product or the drug product itself. Maker-specific features are obvious, for instance, to readers of drug makers' catalogs from which imprints and descriptive information may be collected, since it is the one common feature in all the imprints therein listed. As an example, in the Abbott Laboratories catalog hundreds of solid dosage forms are found and they all bear Abbott's distinctive maker-specific logo. Primary imprint features are also important for they become assigned components in the search routines of the present invention, as the attention of users is first directed to them in a hierarchical scheme.

Examples of primary features are the Abbott Laboratories logo in FIG. 31.1, the number 93 in FIG. 31.2 and the letters BRA in FIG. 31.3. Subsequent to the selection of a primary imprint feature, the method determines directly secondary features.

A "secondary" imprint feature is the feature appearing along with a primary feature within an existing imprint on a drug product. In fact, all remaining features within an imprint after a primary feature is selected are secondary features. Examples of secondary features in FIG. 31 are the numbers 3 and 150 in FIG. 31.2, the number 200 in FIG. 31.3, and the letters NS in FIG. 31 .1. In the case that no selection of a primary, and therefore secondary, feature can be made, the imprint as a whole must be assessed as a tertiary feature, following from the above definitions.

A "tertiary" imprint feature fails the criteria for primary and secondary features. Derived by exclusion therefore, a tertiary feature is the sole feature of, and indeed is, the very imprint of the drug product. Example of a tertiary feature is the number 230 in FIG. 31.4. It is further appreciated that where a tertiary feature is assessed, no primary and secondary features may exist in the imprint. Further by convention of the present invention, imprints which feature the very brand name of the drug product, e.g., variations of the imprint Tylenol® as found on several McNeal Laboratories' analgesic products, are specifically assigned as tertiary features; these brand-specific imprints are few yet are growing in number.

In the present invention the database of imprints along with their descriptors (such as in Readi-TCID®) is arranged by a method that:

1) organizes all imprints by features into three mutually exclusive feature types, i.e., primary, secondary and tertiary, and further
2) assigns these imprint features to the database as components in four mutually exclusive classes, i.e., logo, numeric, alphabetic and remainder of the code classes, in the four search routines,
   a) placing primary features as components respectively into logo, numeric and alphabetic classes, and
   b) secondary and tertiary features as components into the remainder of the code class,
3) requires the graphical expression of each logo feature (see FIG. 3),
4) further assigns a unique number to each logo graphic within the logo class (in FIG. 4, component 4.8), and
5) requires a relationship be maintained between components within classes and the respective set of imprint descriptors, in the records of any applicable database.

In a database or spread sheet built to these specifications (such as Readi-TCID®), the above four classes and related descriptors are assigned to specific data sets or columns as variables, common within each drug product record; the data sets or columns containing mutually exclusive component class members, descriptors or other control values may have entries or may be empty in any one record.

In Tables 1 and 2, an exemplary set of variables and values identified by function as to components, descriptors and control are shown, for the six exemplary imprints herein and their corresponding drug products. As an example, the logo imprint search routine (discussion follows) in FIGS. 2 through 7 sorts hierarchically first for the logo component variable and then for the remainder of the code component variable and then displays the requisite descriptors in FIG. 7, thereby making the identification.

The method of this invention sets up records in an applicable database for the hierarchical search routines to address only the data sets or columns containing the above four component classes, derived from imprint features, in order to make a definitive declaration of identification. By contrast, other methods present indiscriminately any record containing the string of imprint characters or digits as the search criterion is found not only in the imprint but also in descriptor fields, leaving users to make the ultimate choice of an identification from multiple records.

For example, had a user attempted to identity the imprint in image 31.1 in FIG. 31 by the feature NS alone since existing technology does not accommodate logos, all six exemplary records in Tables 1 and 2 would immediately display, having therein 'NS' in some descriptor field.

TABLE 1

Exemplary Drug Product Records

Figure 7:
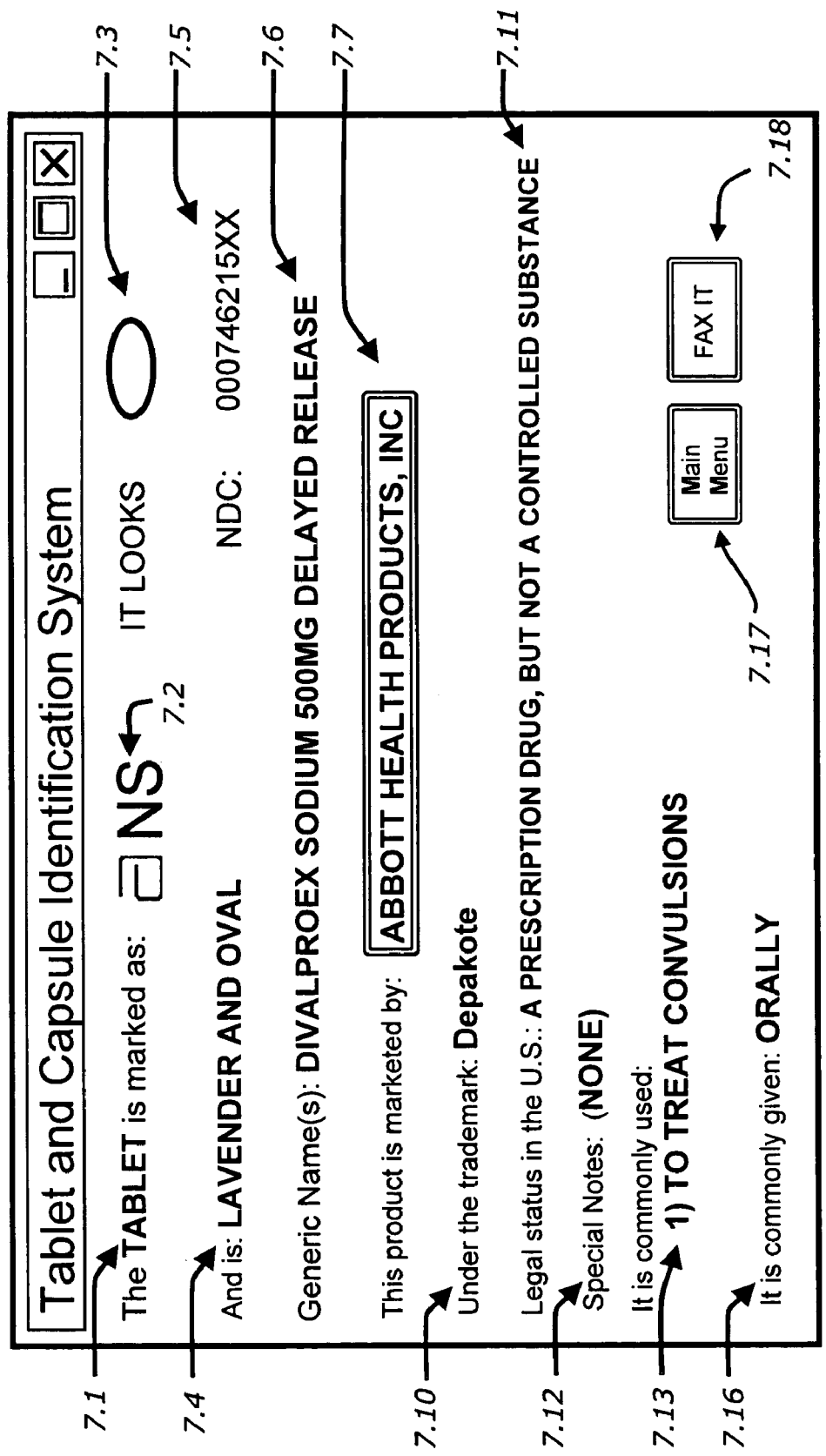
FIG. 7 is a screen shot illustrating a Result screen accessed by designation of the next user option in FIG. 6 and includes the dosage form descriptor (underlined here) within the display (The tablet is marked as) followed by an imprint recap display which represents the imprint features as both a graphical of the logo, and text of remainder of the code, component class members reconfirming positively the imprint on the dosage form, a graphical display of the tablet shape (It looks like field), a physical description display (white, caplet and scored), a NDC display, a generic name(s) display, drug manufacturer's name display and user option (This product is marketed by), a legal status in the US display, a special notes display, it is commonly used display, it is commonly given display, a main menu user option and a fax it user option.
Figure 12:
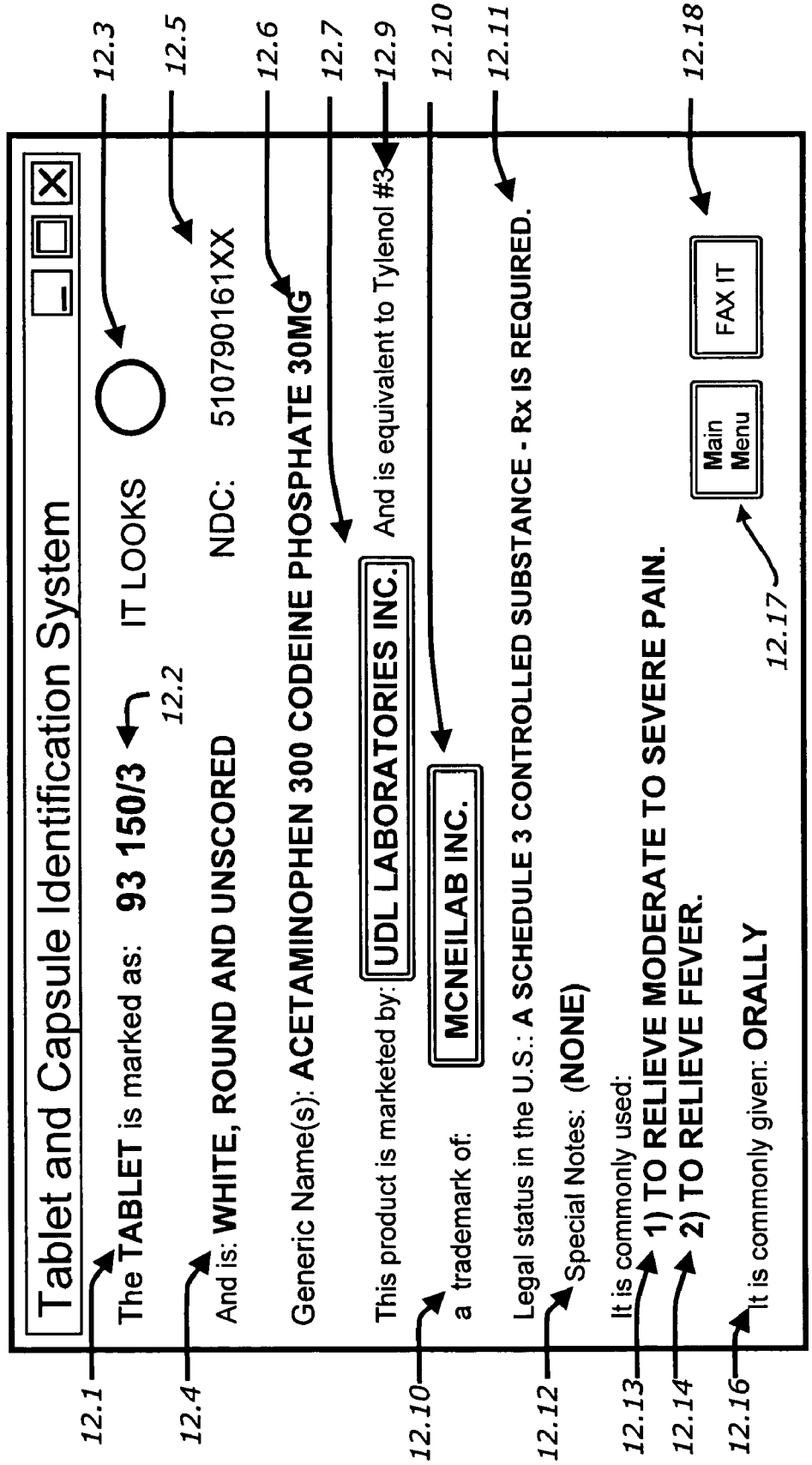
FIG. 12 is a screen shot illustrating a Result screen accessed by designation of the next user option in FIG. 11 and includes the dosage form descriptor within the display (The tablet is marked as) followed by an imprint recap display reconfirming positively the imprint on the dosage form for which the current inquiry is made, a graphical display of the tablet shape (It looks like field), a physical description display (white, round and scored), a NDC display, a generic name(s) display, a drug manufacturer's name display and user option (This product is marketed by), the manufacturer's trademark display (Under the trademark), a legal status in the US display, a special notes display, it is commonly used display, it is commonly given display, a main menu user option and a fax it user option.
Figure 17:
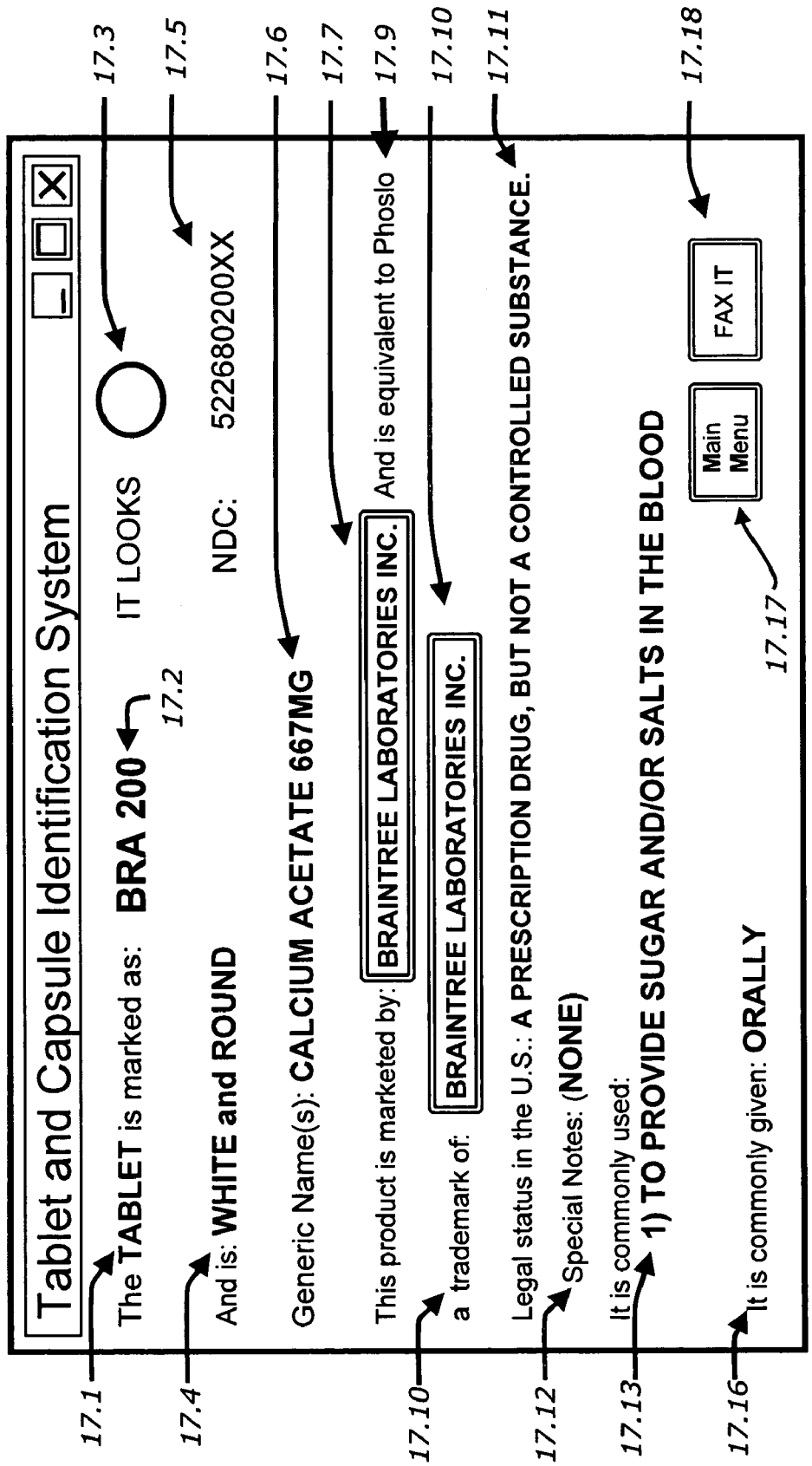
FIG. 17 is a screen shot illustrating a Result screen accessed by designating the next user option of FIG. 16 and includes the dosage form descriptor within the display (The tablet is marked as) followed by an imprint recap display reconfirming positively the imprint on the dosage form for which the current inquiry is made, a graphical display of the tablet shape (It looks like field), a physical description display (It blue caplet and unscored), a NDC display, a generic name(s) display, a drug manufacturer's name display and user option (This product is marketed by), the manufacturer's trademark display (Under the trademark), a legal status in the US display, a special notes display, it is commonly used display, it is commonly given display, a main menu user option and a fax it user option.
Figure 21:
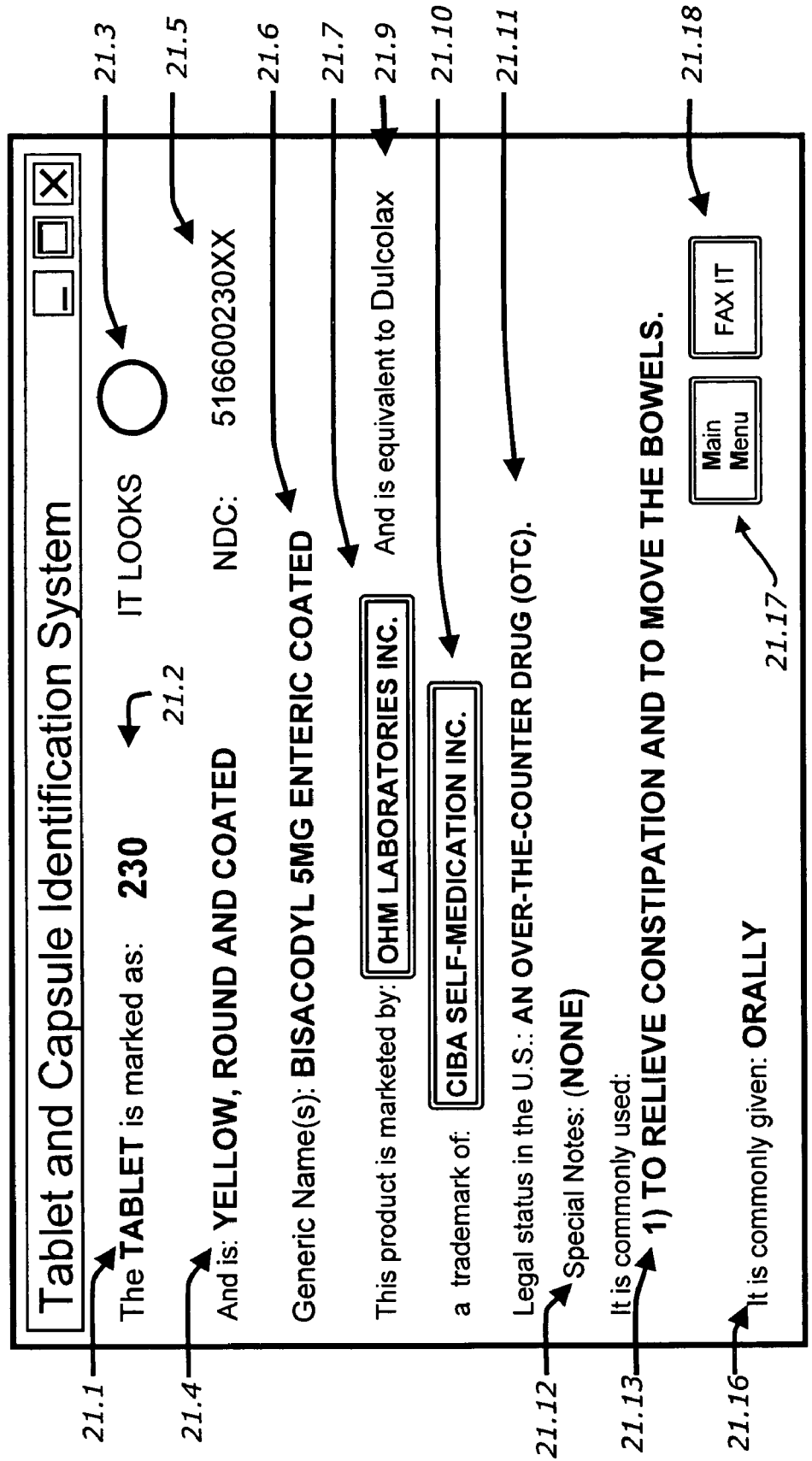
FIG. 21 is a screen shot illustrating a Result screen accessed by designation of the next user option in FIG. 20 and includes the dosage form descriptor within the display (The softgel is marked as) followed by an imprint recap display reconfirming positively the imprint on the dosage form for which the current inquiry is made, a graphical display of the tablet shape (It looks like field), a physical description display (dk maroon clear and oval), a NDC display, a generic name(s) display, a drug manufacturer's name display and user option (This product is marketed by), the therapeutically equivalent trademark display (and is equivalent to), the therapeutically equivalent manufacturer's name display and user option (a trademark of), a legal status in the US display, a special notes display, it is commonly used display, it is commonly given display, a main menu user option and a fax it user option.
Figure 24:
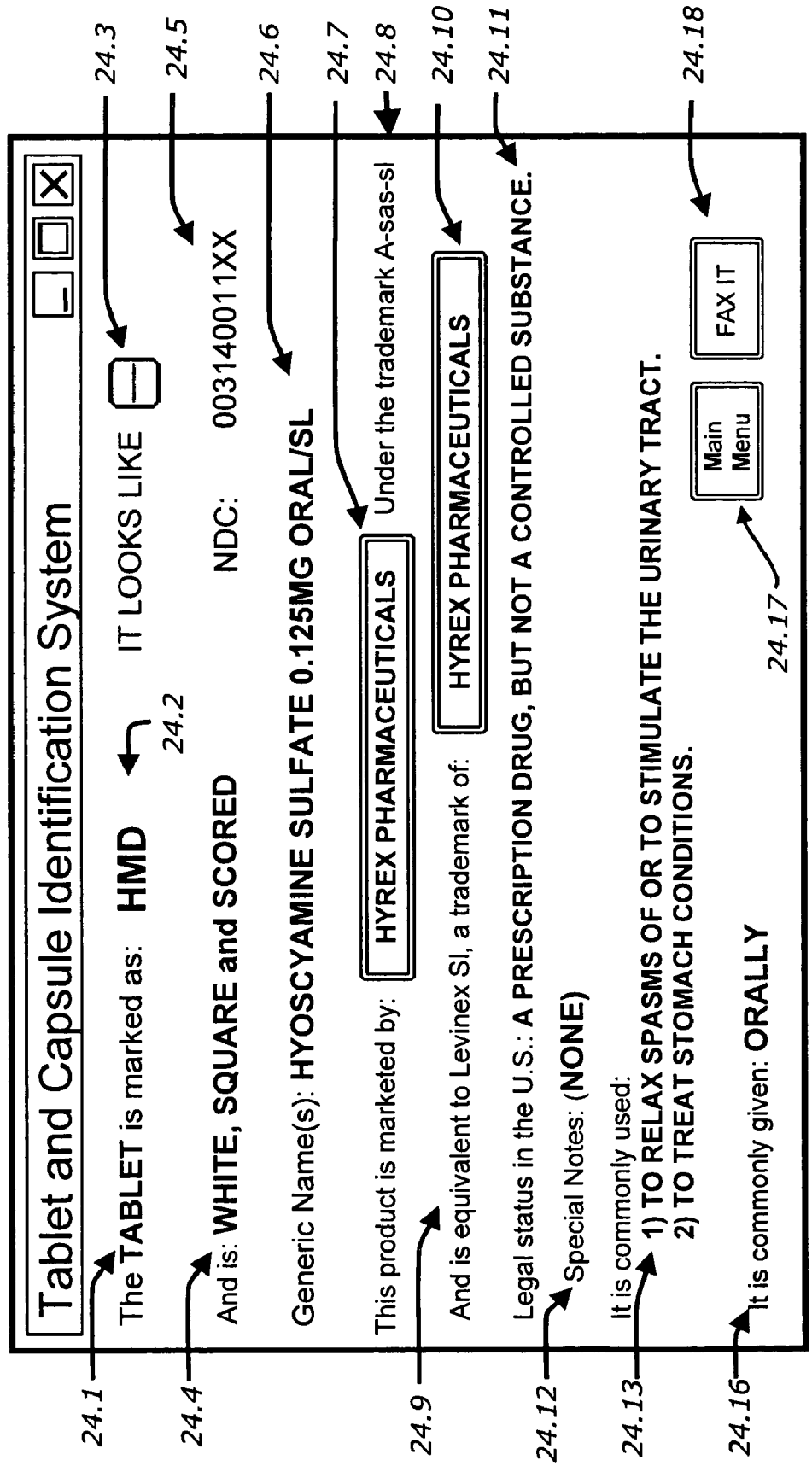
FIG. 24 is a screen shot illustrating a Result screen accessed by designating the next user option of FIG. 23 and includes the dosage form descriptor within the display (The tablet is marked as) followed by an imprint recap display reconfirming positively the imprint on the dosage form for which the current inquiry is made, a graphical display of the tablet shape (It looks like field), a physical description display (white square and scored), a NDC display, a generic name(s) display, a drug manufacturer's name display and user option (This product is marketed by), the manufacturer's trademark (under the trademark), the therapeutically equivalent manufacturer's trademark display (and is equivalent to), the trademark drug manufacturer's name display and user option (a trademark of), a legal status in the US display, a special notes display, it is commonly used display, it is commonly given display, a main menu user option and a fax it user option.

|   | Function | Variable Names | Variables in FIG. 7 | Variables in FIG. 12 | Variables in FIG. 17 | Variables in FIG. 21 | Variables in FIG. 24 |
|---|---|---|---|---|---|---|---|
| 1 | | | | | | | |
| 2 | | | Note: Only Descriptors and (Search) Components Appear in Result Screen Shots, noted here by Figure number. | | | | |
| 3 | Function | Variable Names | Variables in FIG. 7 | Variables in FIG. 12 | Variables in FIG. 17 | Variables in FIG. 21 | Variables in FIG. 24 |
| 4 | Descriptor | NDC | 000748215XX | 510790161XX | 522660200XX | 51660230XX | 003140011XX |
| 5 | Control | LISTINGS_SEQ | 0000033973 | 0000024843 | | 0000104916 | |
| 6 | Descriptor | BRAND_NAME | | TYLENOL #3 | PHOSLO | DULCOLAX | LEVINEX SL |
| 7 | Descriptor | HOUSE_BRAND | DEPAKOTE | | | | A-SAS-SL |
|   | Descriptor | DESCRIPTION | DIVALPROEX SODIUM 500 MG | ACETAMINOPHEN 300 CODEINE | CALCIUM ACETATE | BISACODYL 5 MG | HYOSCYAMINE SULFATE 0.125 MG |
| 8 | | | DELAYED RELSE | PHOSPHATE 30 MG | 667 MG | ENTERIC COATED | ORAL/SL |
| 9 | Control | DFG | 009 | 001 | 001 | 001 | 045 |
| 10 | Descriptor | DOSEFORM | TABLET | TABLET | TABLET | TABLET | TABLET |
| 11 | Descriptor | CATLGR | ABBOTT | UDL*** | BRAINT | OHMLAB | HYREX* |
| 12 | Control | FIRM_SEQ | 0053745 | 0045928 | 0011418 | 0039620 | 0000283 |
| 13 | Control | DFG | 009 | 001 | 001 | 001 | 046 |
| 14 | Descriptor | COLOR | LAVENDER | WHITE | WHITE | YELLOW | WHITE |
| 15 | Descriptor | SHAPE_OPACITY | OVAL | ROUND | ROUND | ROUND | SQUARE |
| 16 | Descriptor | SCORING_OTHER | UNSCORED | | | COATED | SCORED |
| 17 | Control | IMPRINT | (ABBOTT)A/NS | 93/1503 | BRA200 | 230 | HMD |
| 18 | Descriptor | STAT | PRESCRIPTION DRUG, BUT NOT A CONTROLLED SUBSTANCE. | A SCHEDULE 3 CONTROLLED SUBSTANCE-RxlS REQUIRED. | PRESCRIPTION DRUG, BUT NOT A CONTROLLED SUBSTANCE. | AN OVER-THE-COUNTER DRUG (OTC). | PRESCRIPTION DRUG, BUT NOT A CONTROLLED SUBSTANCE. |
| 19 | Control | NB | (NONE) | (NONE) | (NONE) | (NONE) | (NONE) |
| 20 | Control | DOC_TYPE | PDR1995 | CATALOG | PDR1995 | CATALOG | CATALOG |
| 21 | Control | DOC_DATE | 121995 | 199503 | 199511 | 199412 | 199607 |
| 22 | Control | INT | FDR | FDR | FDR | FDR | FDR |
| 23 | Descriptor | ROUTE_OF_ADM | ORALLY | ORALLY | ORALLY | ORALLY | ORALLY |
| 24 | Control | USE1 | 1374 | 1721 | 0915 | 0876 | 0509 |
| 25 | Control | USE2 | | 1728 | | | 0677 |
| 26 | Control | USE3 | | | | | |
| 27 | Control | USE4 | | | | | |
| 28 | Control | Component LOGO1 | 103 | | | | |
| 29 | Component | LOGO2 | | | | | |
| 30 | Component | NUM | | 93 | | | |
| 31 | Component | ALPHA1 | | | BRA | | |
| 32 | Component | ALPHA2 | | | | | |
| 33 | Component | REMAINDER | NS | 150/3 | 200 | 230 | HMD |

TABLE 2

EXEMPLARY RELATIONAL RECORDS

Figure 28:
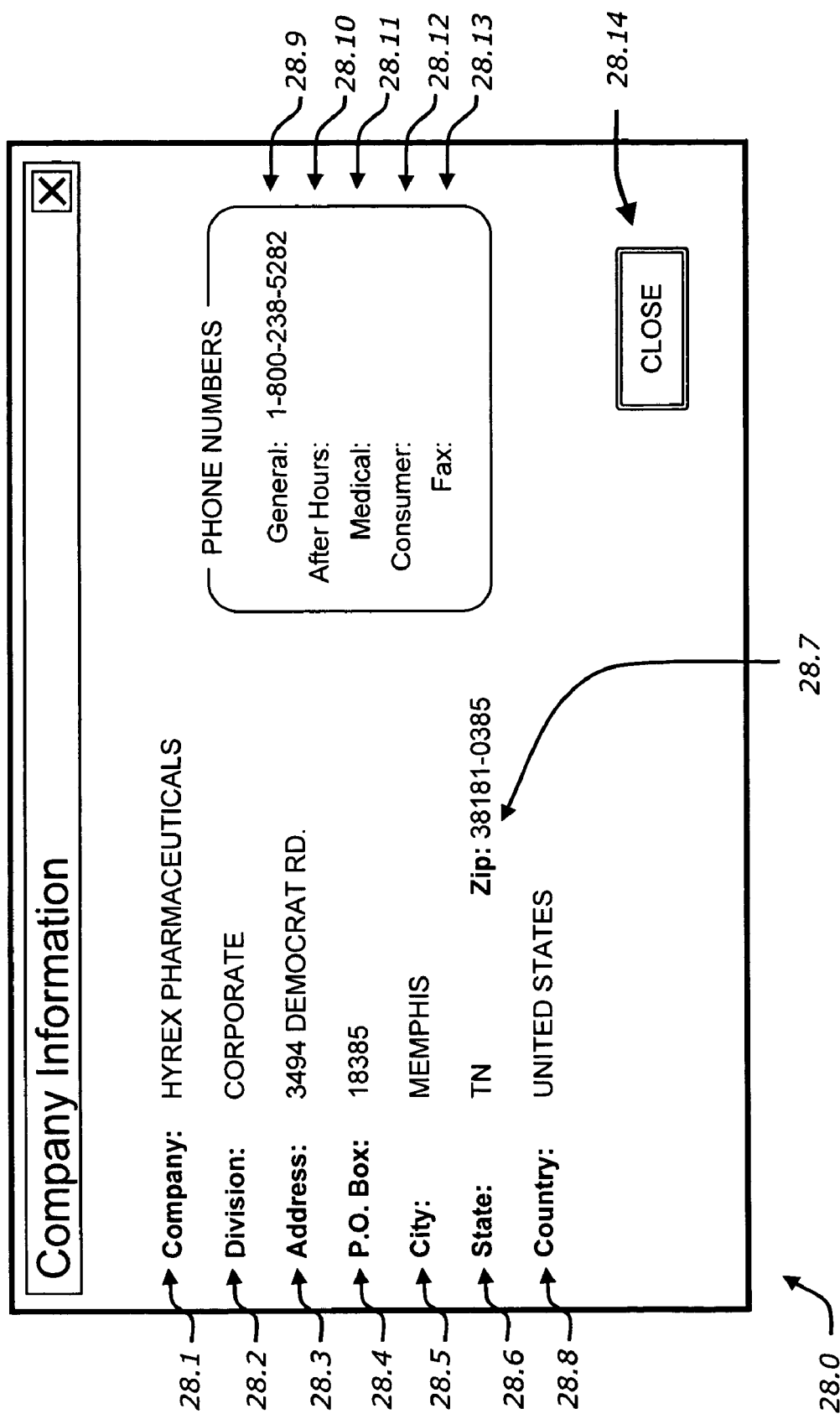
FIG. 28 is a screen shot illustrating a company information screen, accessed by the drug manufacturer's name displays and user options of FIGS. 7, 12, 17, 21, 24 and 27, showing, but not limited to, a company identifier, a division identifier, an address identifier, a P.O. Box identifier, a city identifier, a state identifier, a zip code identifier, a country identifier, phone numbers identifier and a close user option.

RE: Table 1 line 12 - 'FIRM_SEQ' Variables as seen in FIG. 28

| 12 | Control | FIRM_SEQ | 0063745 | 0045928 | 0011418 | 0039620 | 0000263 | 0000001 |
|---|---|---|---|---|---|---|---|---|
| | | NDC_LABELER_CODE | 00074 | 51079 | 52268 | 51660 | 00314 | 00002, 59075 |
| | | SHORT_NAME | ABBOTT | UDL*** | BRAINT | OHMLAB | HYREX* | LILLY* |
| | | COMPANY_NAME | ABBOTT HEALTH PRODUCTS INC | UDL LABORATORIES INC | BRAINTREE LABORATORIES INC | OHM LABORATORIES INC | HYREX PHARMACEUTICALS | ELI LILLY AND COMPANY |
| | | DIVISION | | CORPORATE | CORPORATE | CORPORATE | CORPORATE | CORPORATE |
| | | STREET_ADDRESS | D387 AP6C1 100 ABBOTT PARK RD | | 60 COLUMBIAN ST | | 3494 DEMOCRAT RD | LILLY CORPORATE DROP CODE 2542 |
| | | PO_BOX | | 10319 | 850929 | 7397 | 18385 | |
| | | CITY | ABBOTT PARK | ROCKFORD | BRAINTREE | NORTH BRUNSWICK | MEMPHIS | INDIANAPOLIS |
| | | STATE_PROV | IL | IL | MA | NJ | TN | IN |
| | | ZIP | 60064-3500 | 61131-3019 | 02185-0929 | 08902 | 38181-0385 | 48285 |
| | | COUNTRY | UNITED STATES | UNITED STATES | UNITED STATES | UNITED STATES | UNITED STATES | UNITED STATES |
| | | GENERAL_PHONE | 1-800-222-8883 | 1-800-435-5272 | 1-617-843-2202 | 1-800-527-8481 | 1-800-2385282 | 1-317-276-2000 |
| | | AFTER_HOURS | 1-708-937-7970 | 1-815-282-1201 | | | | 1-800-545-5979 |
| | | MEDICAL | 1-800-633-9110 | 1-800-435-5272 | | | | |
| | | CONSUMER_INFO | | 1-815-282-9391 | 1-617-843-6758 | | | |
| | | FAX | | | 1-617-843-7932 | | | 1-317-277-1827 |

RE: Table 1 lines 25 & 26 - 'USE'

| | Function | Variable Names | Value |
|---|---|---|---|
| 24 | Descriptor | USE1 1374 | TO TREAT CONVULSIONS. |
| | | 1721 | TO RELIEVE MODERATE TO SEVERE PAIN. |
| | | 0915 | TO PROVIDE SUGAR AND/OR SALTS IN THE BLOOD. |
| | | 0876 | TO RELIEVE CONSTIPATION AND TO MOVE THE BOWELS. |
| | | 0509 | TO RELAX SPASMS OF OR TO STIMULATE THE URINARY TRACT, |
| | | 0408 | TO TREAT DEFICIENCY ANEMIAS. |
| 25 | Descriptor | USE2 1728 | TO RELIEVE FEVER. |
| | | 0877 | TO TREAT STOMACH CONDITIONS. |
| | | 0913 | TO ADD VITAMINS AND/OR MINERALS TO YOUR DIET. |

RE: Table 1 lines 9 - 'DFG'

| | Function | Variable Names | | | |
|---|---|---|---|---|---|
| 29 | Control | DFG 001 | DFG 009 | DFG 046 | DFG051 |
| | Component | RNDUNSCR.ICO | OVALUNSC.ICO | SQRSCRD.ICO | OPAQOPAQ.ICO |
| | Value |  |  |  | |

RE: FIG. 32, lines 28 - 'CONTROL LOGO1'

| | Function | Variable Names | | Variable Names | |
|---|---|---|---|---|---|
| | Control | | Logo 103: | | Logo 163: |
| | Component | | ABBOTT.ICO | | LILLY.ICO |
| | Value | | | | |

It is appreciated that all of the imprint features above, except the Abbott Laboratories logo feature, could easily appear in many descriptor fields in a large database. Such fields might be strength of the active ingredient or as a part of the National Drug Code or as a part of the address of the drug maker, producing multiple records from which a user must make an identification. Patently the results are different from the method and routines of the present invention. It is novel therefore in this invention to exclude boldly descriptor data sets from search routines and to focus solely on four data sets containing imprint components, definitively leading to a declarative product identification.

The search routines are the obverse of method and an inseparable part of the present invention, exemplified by Screen Shots, FIGS. 2 through 28. The search routines leading to a declarative identification of a drug product:

1) present component class members, derived from only primary features in step 2-*a* of Method, serially by logo (see FIG. 3), numeric (see FIG. 8) and alphabetic (see FIG. 13) classes, from which users may make an initial selection, then
2) present remainder of the code component class members, derived solely from secondary imprint features in step 2-*b* of Method, correlated only to an above selected component (respectively in FIG. 5, 10 or 15) through the hierarchical search of these features,
3) or having made no selection in the routines of 1 and 2 above, thereby excluding hierarchically all components in the above logo, numeric and alphabetic classes and their corresponding components derived from secondary imprint features in the fourth remainder of the code class, thereby significantly improving the precision of the following routine,
4) alternatively present remainder of the code component class members (see FIG. 18), derived exclusively from tertiary imprint features in step 2-*b* of method and brand-specific components, where all secondary component class members are excluded, from which users alternatively may make an initial selection,
5) further present physical descriptors of the resultant declarative drug product (see FIG. 6, 11, 16 or 20) as chosen by either of the above step(s) 1 and 2 or 4,
6) require users to confirm the declaration of identification by comparing positively imprint physical descriptors with the drug product physical characteristics, in hand or as reported to the user, thus avoiding a false-positive identification, and
7) declare identification of the drug product by descriptors (see FIG. 7, 12, 17 or 21), associated with the component variables in an applicable database.

In FIG. 31, exemplary physical descriptors for the graphic images of imprints include: lavender, oval and film-coated for FIG. 31.1 (corresponding to the screen in FIG. 7); white, round and unscored for FIG. 31.2 (corresponding to the screen in FIG. 12); white, round and unscored for FIG. 31.3 (corresponding to the screen in FIG. 17); and orange, round and coated (corresponding to the screen in FIG. 21).

The convention of including brand-specific imprints in the fourth search routine is a further novelty to current practices in the art. Isolation of brand-specific components to the last search routine increases the efficiency of the preceding three search routines, by exclusion of obviously identified drug products, for the real task of identifying the preponderance of otherwise unknown drug products.

Routines further accommodate searches by National Drug Code and by House Brand Name, while not novel in and of themselves. These two additional search routines are included herein for their novelty within the present invention: (1) the user arrives at a declarative identification, (2) the addition of the graphics of imprint logos and of dosage forms is further confirmatory of a positive identity, (3) the system is not restricted to experts and (4) use by the public is intended.

The concept that imprints are unique, establishment of three feature types, assignment of features as components to four searchable classes and the hierarchy of the search routines using the four classes lead directly to the definitive declaration of drug product identity. A sixth novelty, contributing to making the search definitive and efficient, is the counterintuitive method of assigning one feature type to three searchable classes and two feature types to a single fourth searchable class and of correlating hierarchically the three feature types and four classes in the search routines.

In FIGS. 1*a*, 1*b*, 1*c* and 1*d*, a flowchart illustrates the routines of the present invention and their relationships to several figures illustrating screens from derivative exemplary computer programs. The search routines are demonstrated, using a suite of inter-related multi-media files, screens, user options, arrays, displays and input fields, all leading to the rapid positive identification of drug products. In the flowchart the three principal routines for accessing drug product information are illustrated: by way of imprint (1.1), National Drug Code (1.2) and House Brand Name (1.3). Imprint subroutines address by logo (1.4), numeric (1.5), and alphabetic (1.6) or by exclusion remainder of the code (1.7) component class members, with respect to observable imprint features on candidate dosage forms. The three sub-routines (1.4, 1.5 and 1.6) converge upon the common sub-routine, i.e., (1.7), for remainder of the code imprint components or as the 'remaining' sub-routine when the other three have been excluded. Sub-routine (1.8) is invoked, should imprint features not be identifiable at any point in the search subroutines. The various routines and sub-routines are derivative of the method of the present invention and extract from the database the identity of drug products by imprint, virtually using method in reverse, and by brand name or NDC. Sub-routine (1.9) provides the user with the option of further information about a specific drug maker or distributor.

Figure 29:
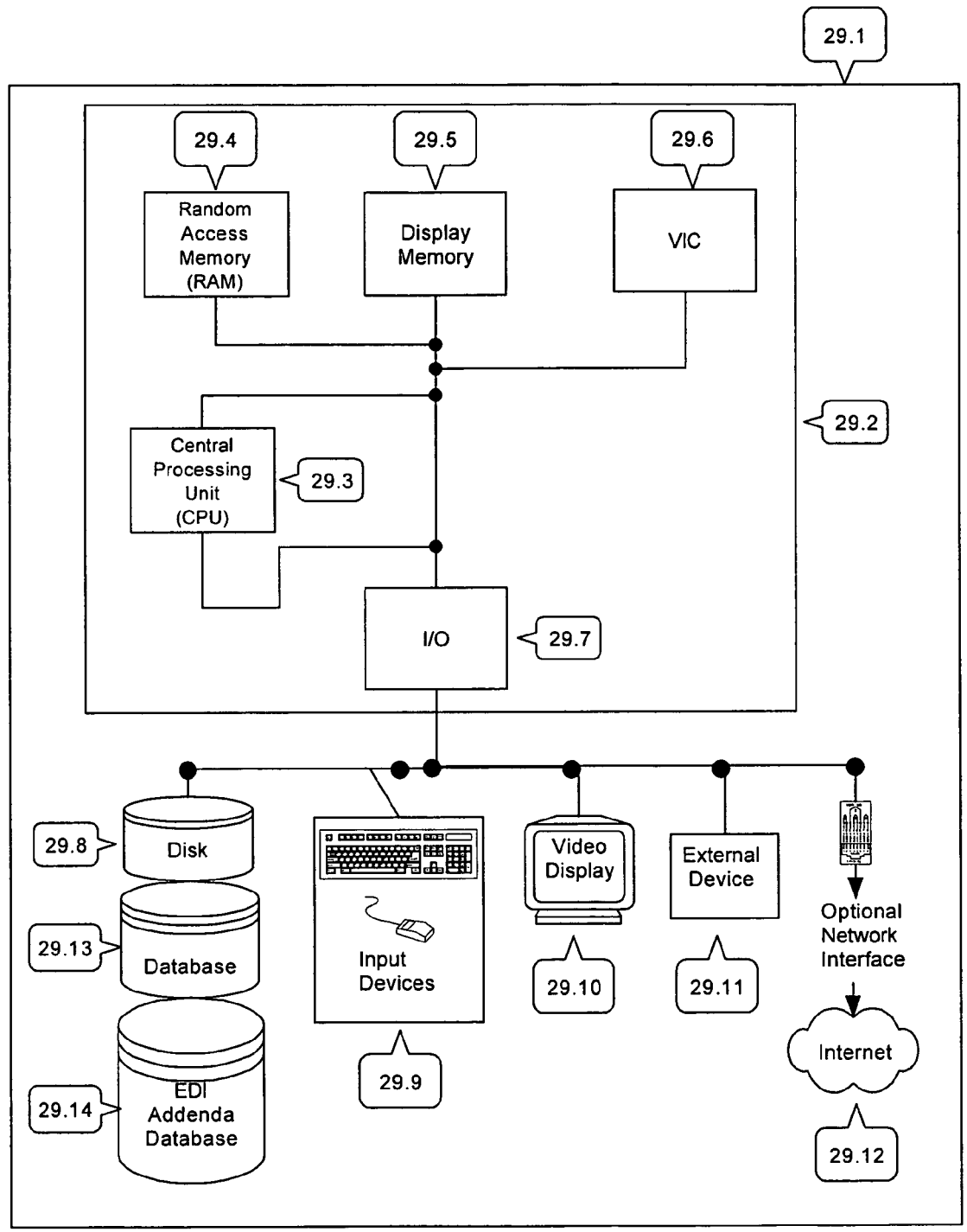
FIG. 29 is a diagram of the modalities of data distribution via a network where the program may operate in all manner of computers—personal, workstation and personal data assistant (PDA), and within local area network, intranet and internet, whether 'hardwired' or wireless.
Figure 30:
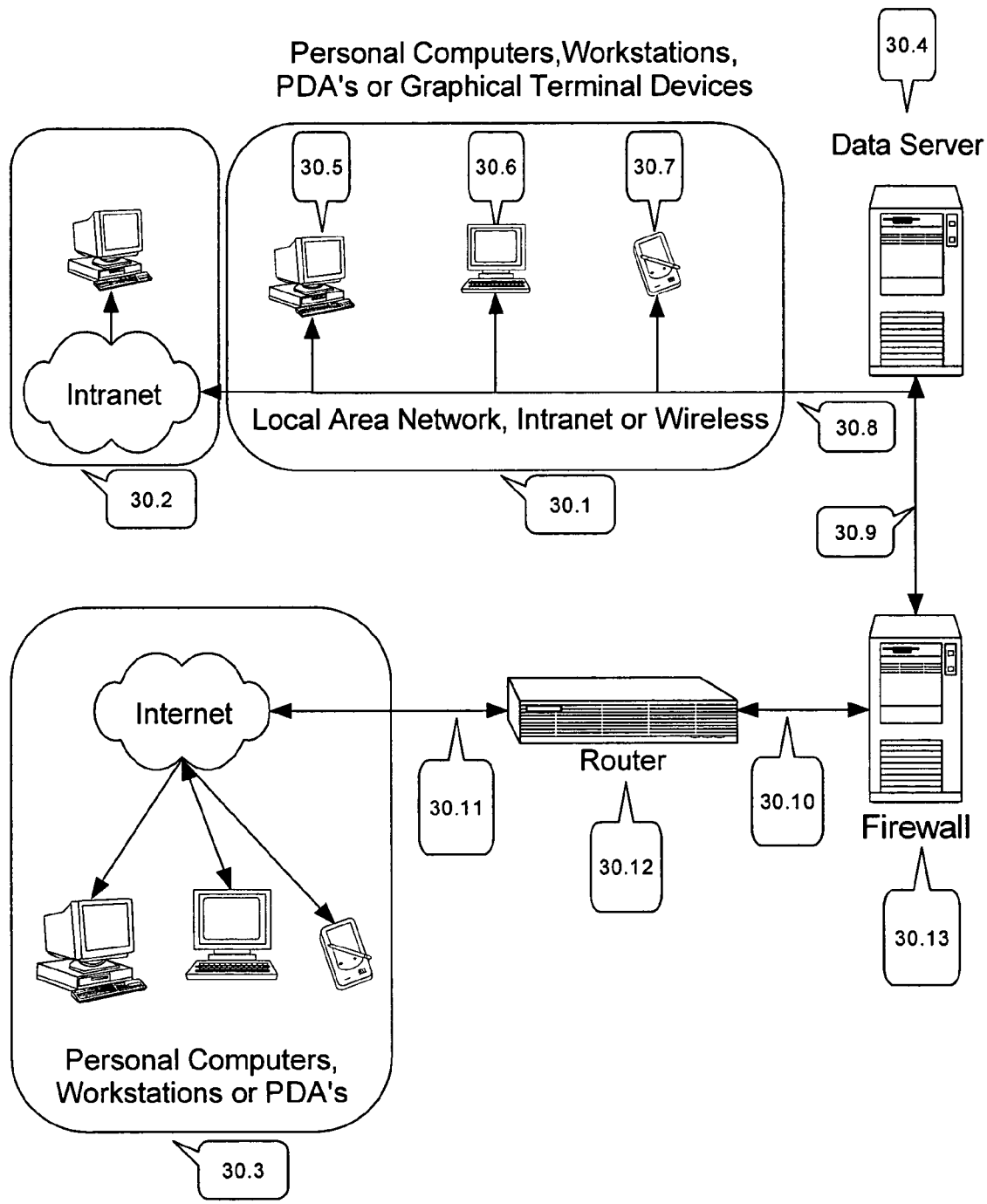
FIG. 30 is a diagram of a personal computer which may utilize the program along with an applicable database in a stand-alone mode; the same program and database may include a PDA (not shown)

FIGS. 2 through 28 illustrate screen shots from the computer-assisted routines in the flowchart. FIGS. 29 and 30 illustrate exemplary computing systems in which the routines and method of the present invention may be functional.

Figure 1B:
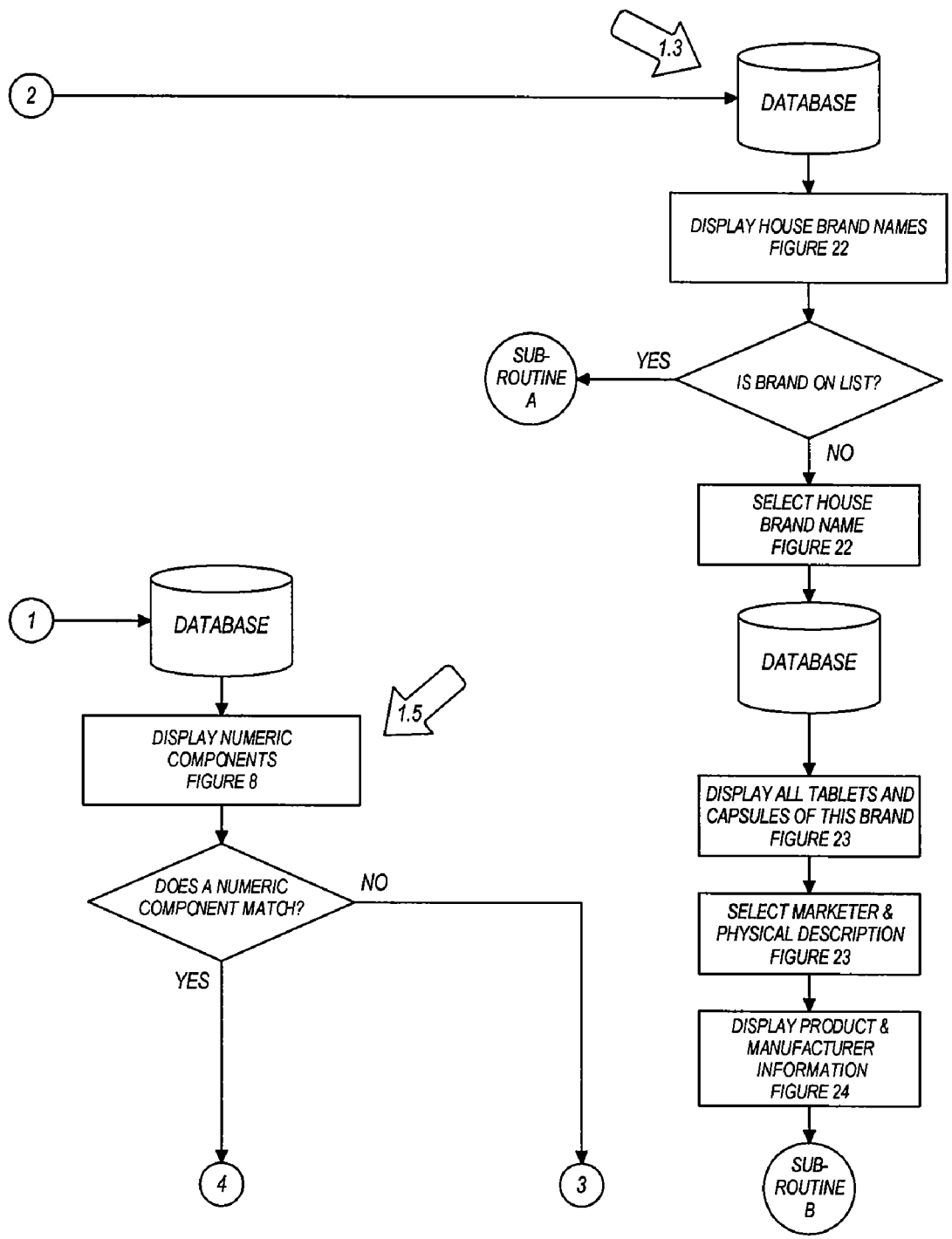
Figure 1C:
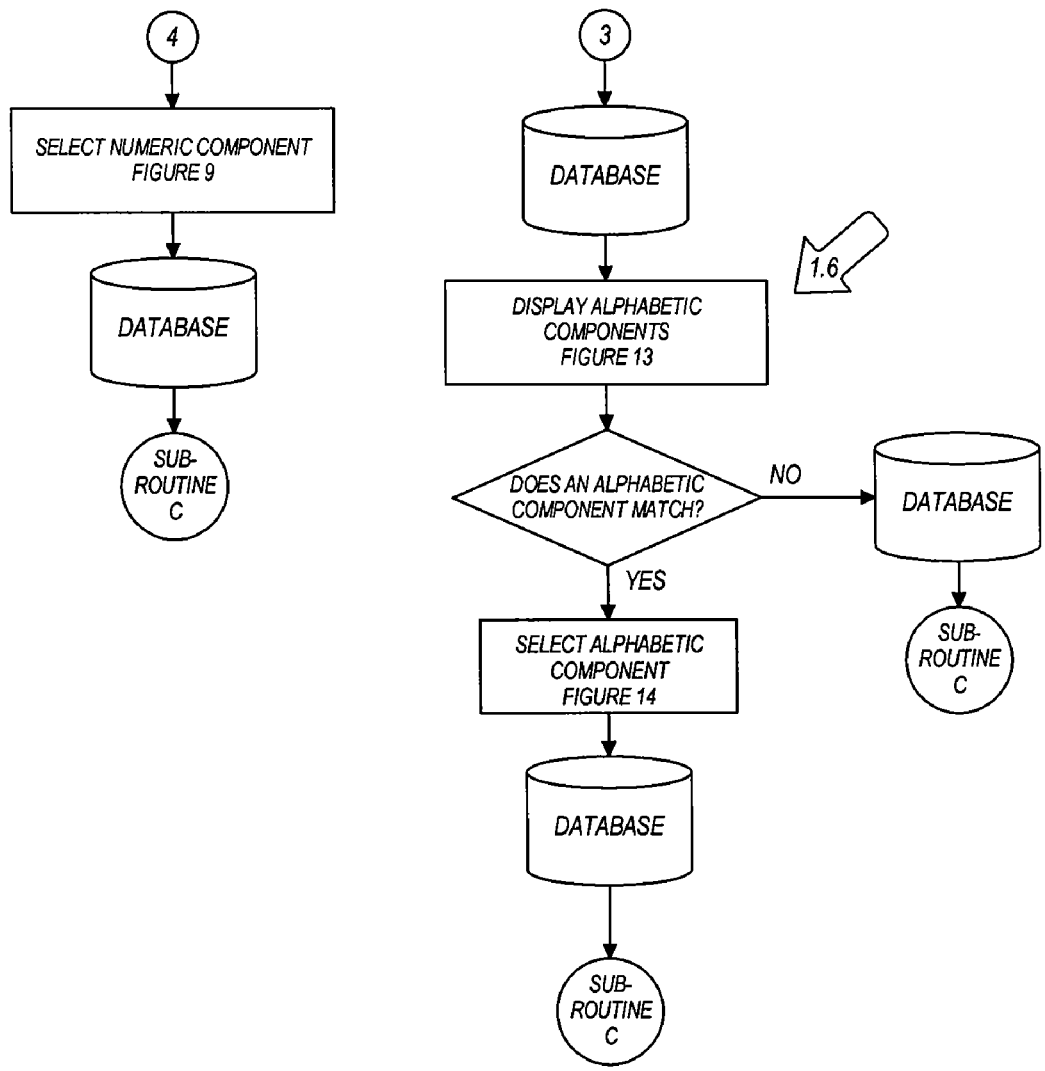
Figure 1D:
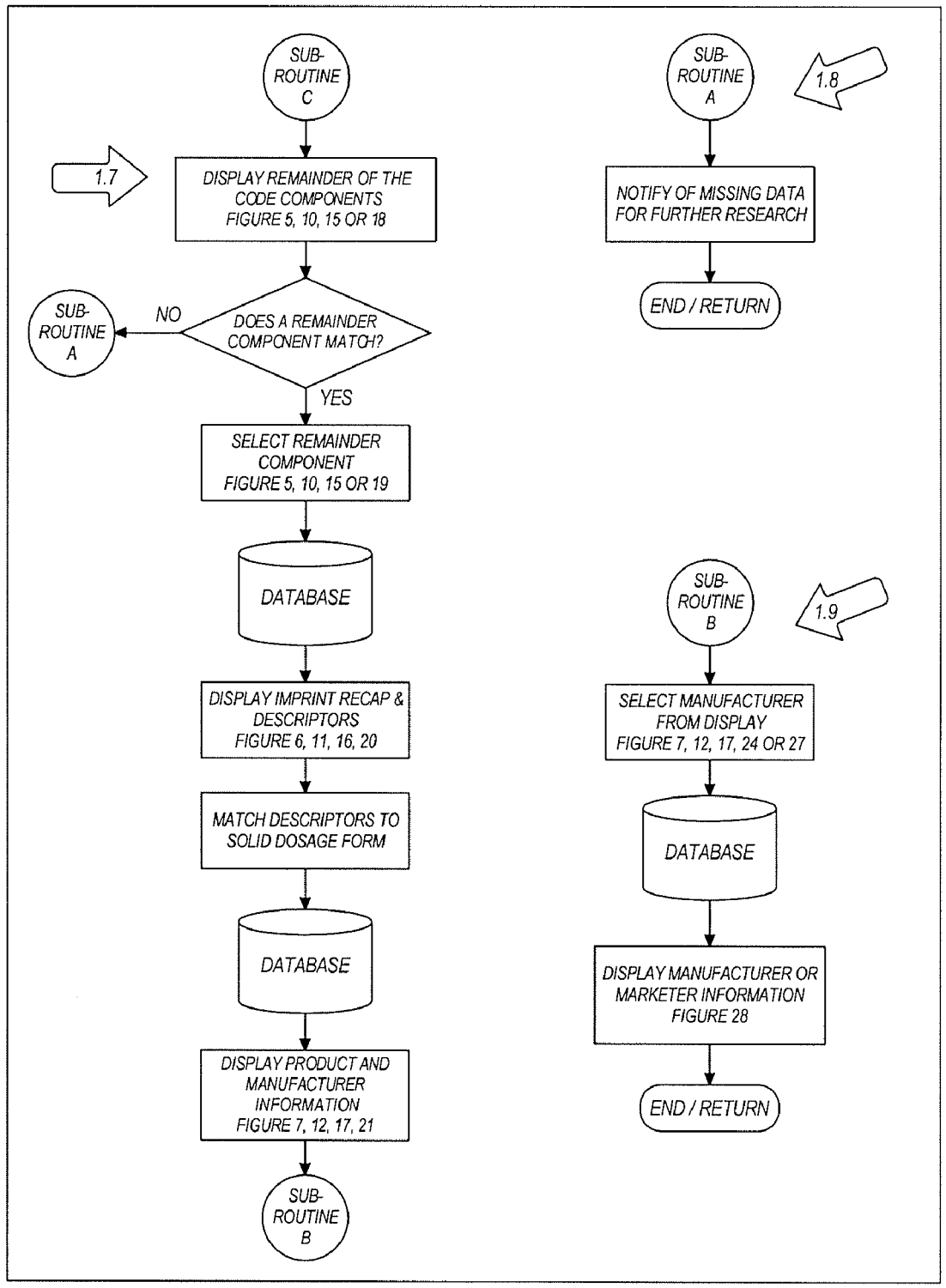
Figure 2:
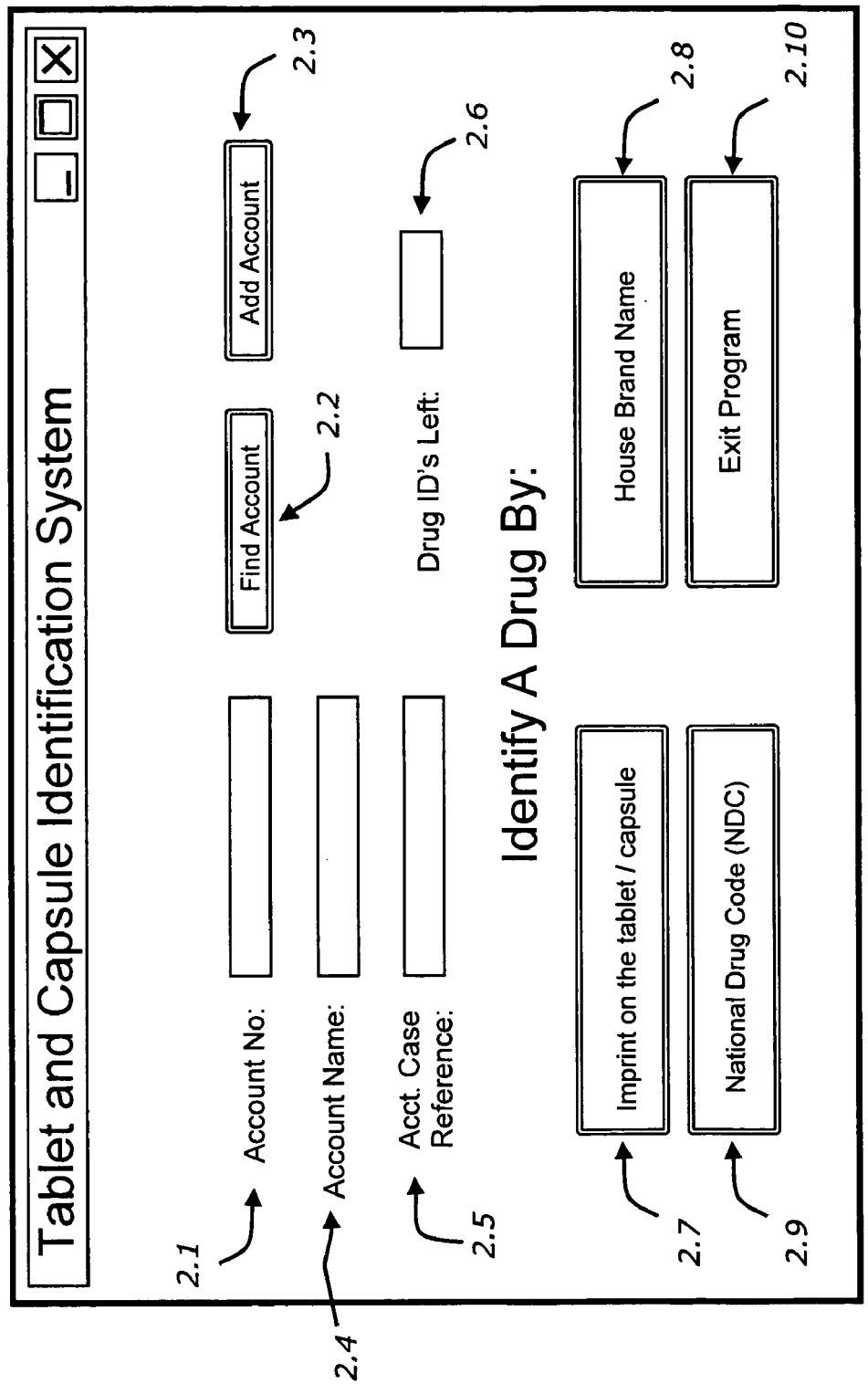
FIG. 2 is a screen shot illustrating a graphical user interface showing a tablet and capsule identification system screen of the present invention including an account number field, a find account user option, an add account user option, an account name display, an account case reference user field, a drug IDs left display, an imprint on the tablet/capsule user option, a house brand name user option, a national drug code (NDC) user option and an exit program user option.

FIG. 2 is a screen shot illustrating a graphical user interface of the present invention showing a tablet and capsule identification system screen 2.0, an account number field 2.1, a find account user option 2.2, an add account user option 2.3, an account name display 2.4, an account case reference user field 2.5, a drug ID's left display 2.6, an imprint on the tablet/capsule user option 2.7, a house brand name user option 2.8, a national drug code user option 2.9, and an exit program user option 2.10.

Through routines of the present invention, exemplified by a series of tablet and capsule identification case-based screens, FIGS. 2-28, a user has the opportunity to identify positively a dosage form on a case by case basis. Because of this contextuality, the methods and routines of the system do more than just identify the dosage form; they provide a value-added, consultative client relationship. Since the materials are developed by experienced practitioners, they are both authoritative and current. Since they are delivered on CD/ROM (not shown) or other form of computer storage medium, over the internet, or over an intranet, they can be used in private or in combination with the advice of a practitioner.

It is appreciated in the present invention that the imprint of interest is partitioned by its feature(s) and correlated to at least one of the component classes identified above. Each respective component class is then correlated or associated with another component class or sub-class thereof; and, then there is a match made between the plurality of component classes and subclasses to obtain an identified imprint.

The various screens identified in FIGS. 2-28 inclusively are the expression of computer-assisted routines for identifying positively an imprint of a dosage form. The dosage form is selected from at least one group consisting of, but not limited to, a tablet, a capsule, a softgel, a gelcap, a geltab, a vaginal tablet, a chewable tablet and a wafer. It is one of the points of novelty of this invention that all dosage forms can be identified; prior art systems involving bar coding were not applicable to every type of solid dosage form.

Figure 3:
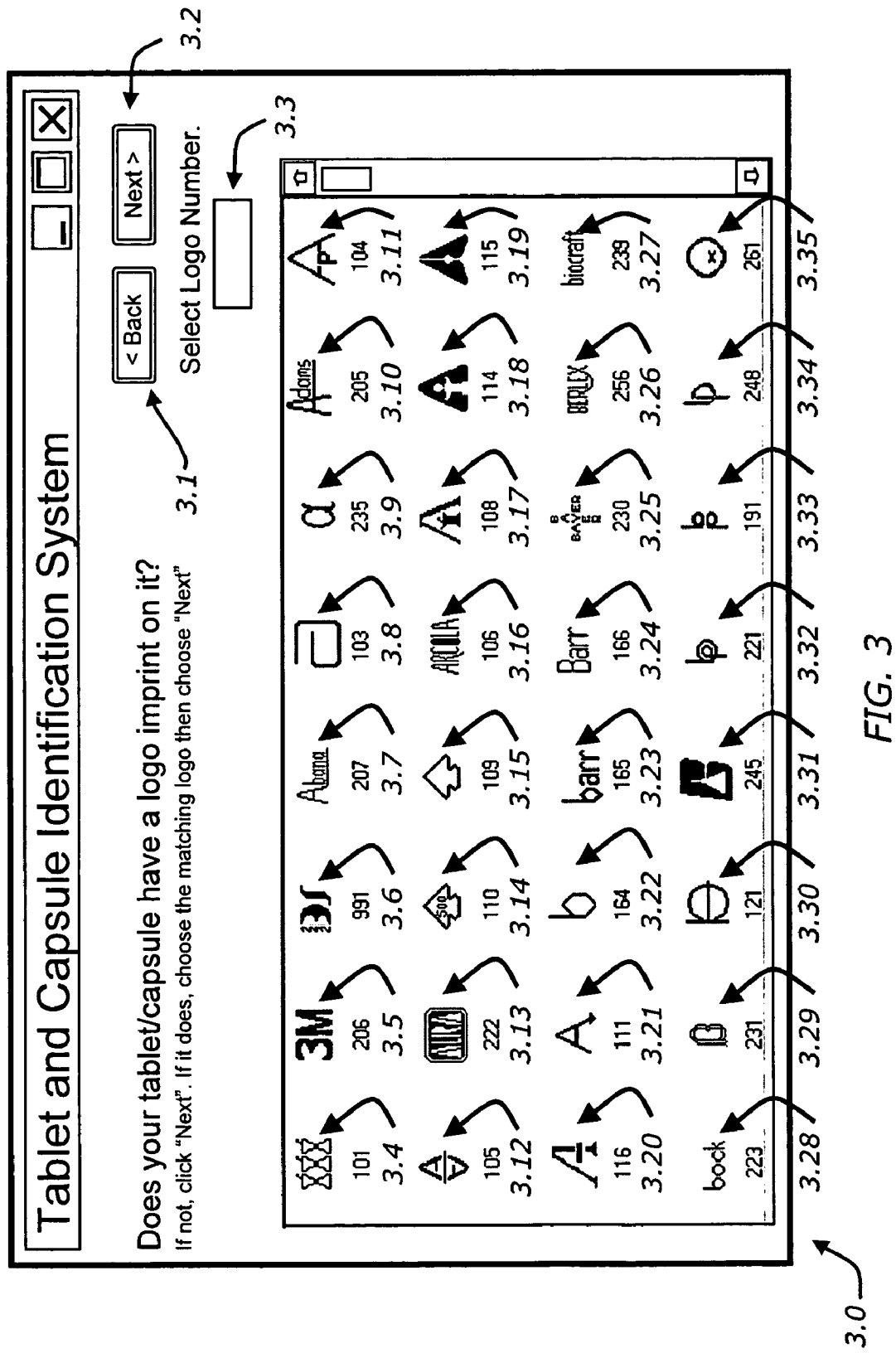
FIG. 3 is a screen shot illustrating a "Does your tablet/capsule have a logo imprinted on it?" screen selected by designating an imprint on the tablet/capsule user option of FIG. 2 and further includes a back user option, a next user option, a selected logo number input field and a scrollable array of a plurality of logo component class members.
Figure 8:
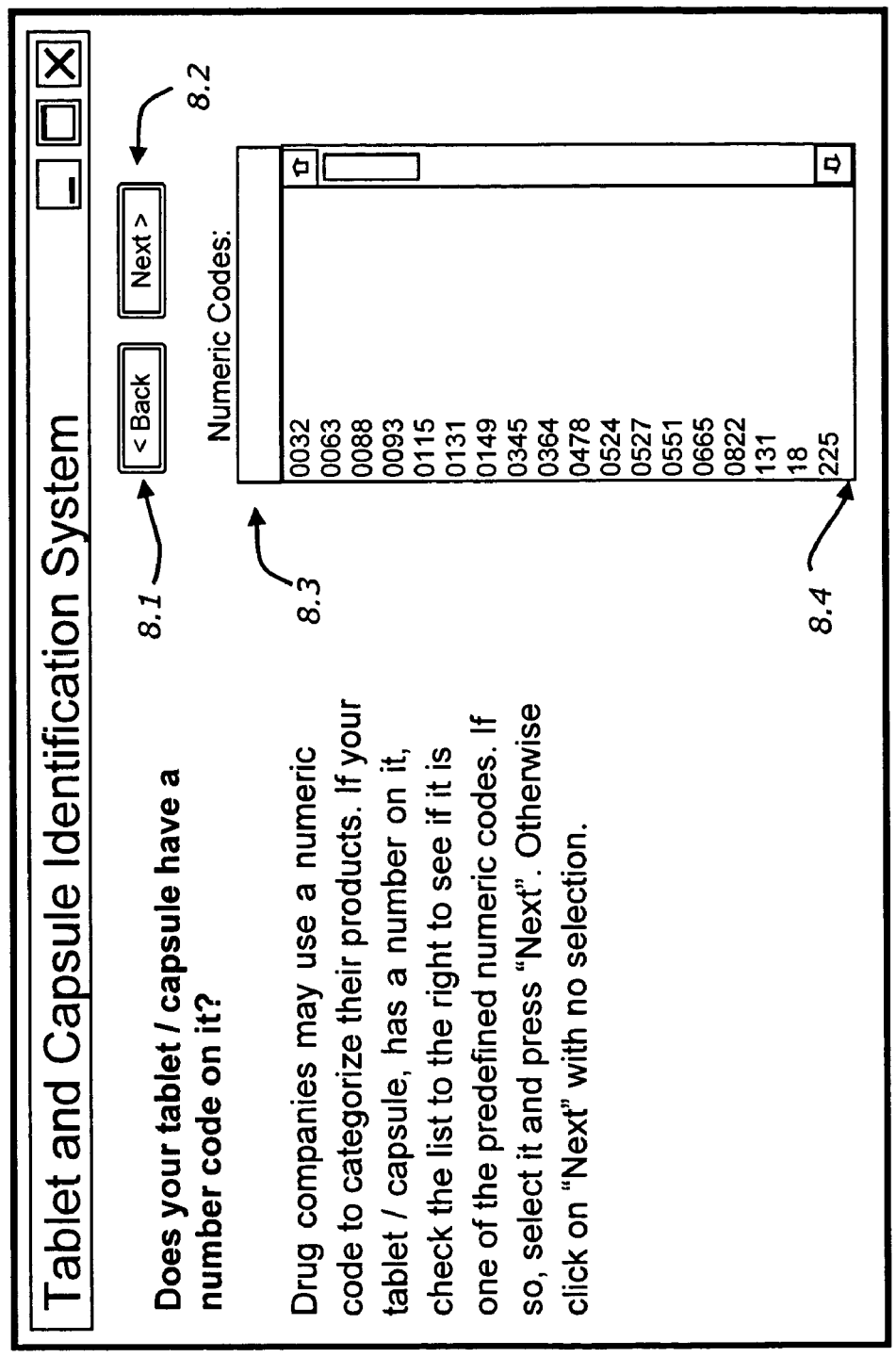
FIG. 8 is a screen shot illustrating a "Does your tablet/capsule have a number code (feature) on it?" screen that follows the screen of FIG. 3 upon designation of the imprint on the next user option and further includes a numeric codes input field, a scrollable numeric code list, a back user option and a next user option.
Figure 13:
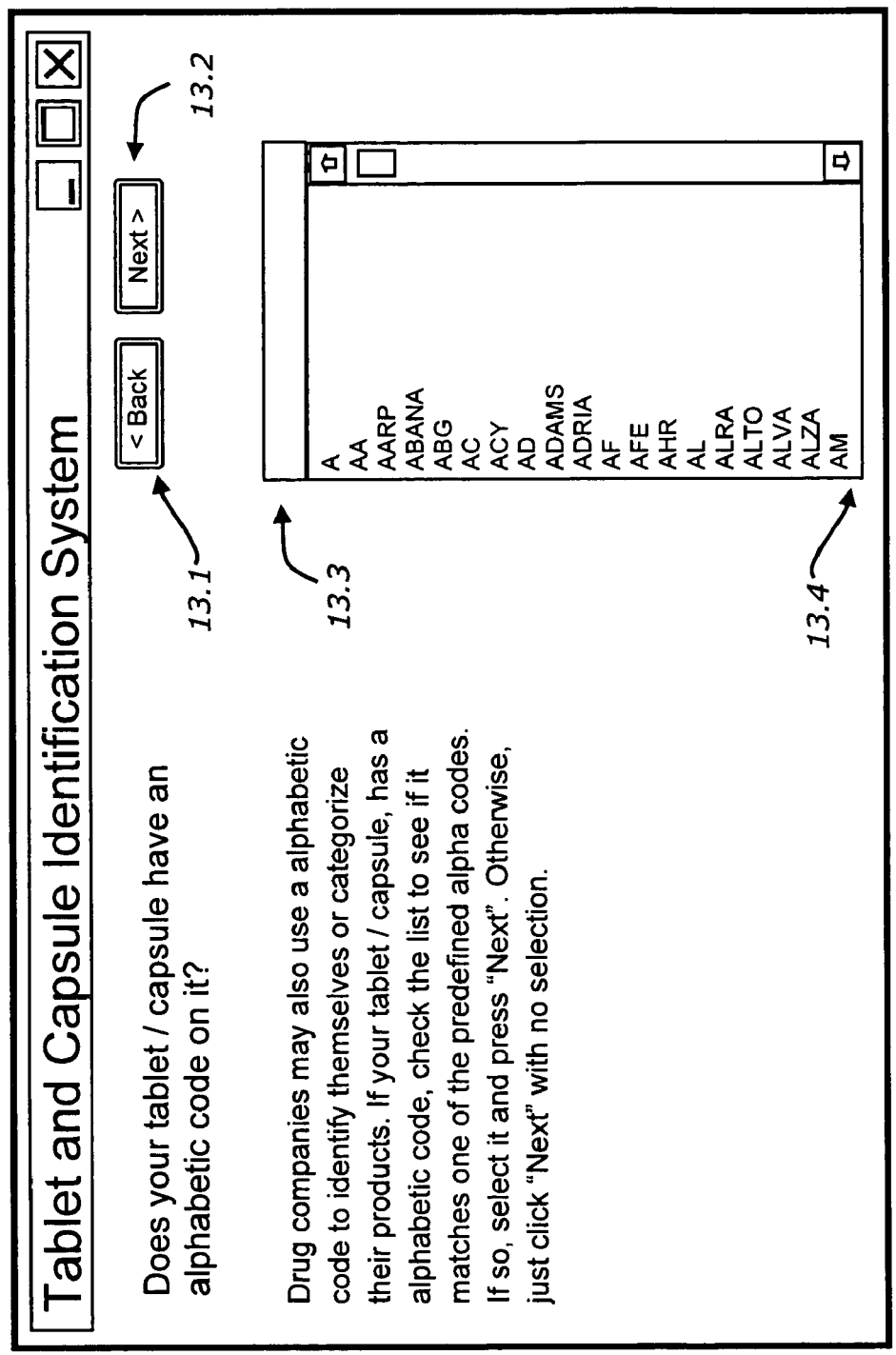
FIG. 13 is a screen shot illustrating a "Does your tablet/capsule have an alphabetic code (feature) on it?" screen that follows the screen of FIG. 8 upon designation of the next user option and also includes an alphabetic code input field, a scrollable alphabetic code list, a back user option and a next user option.
Figure 18:
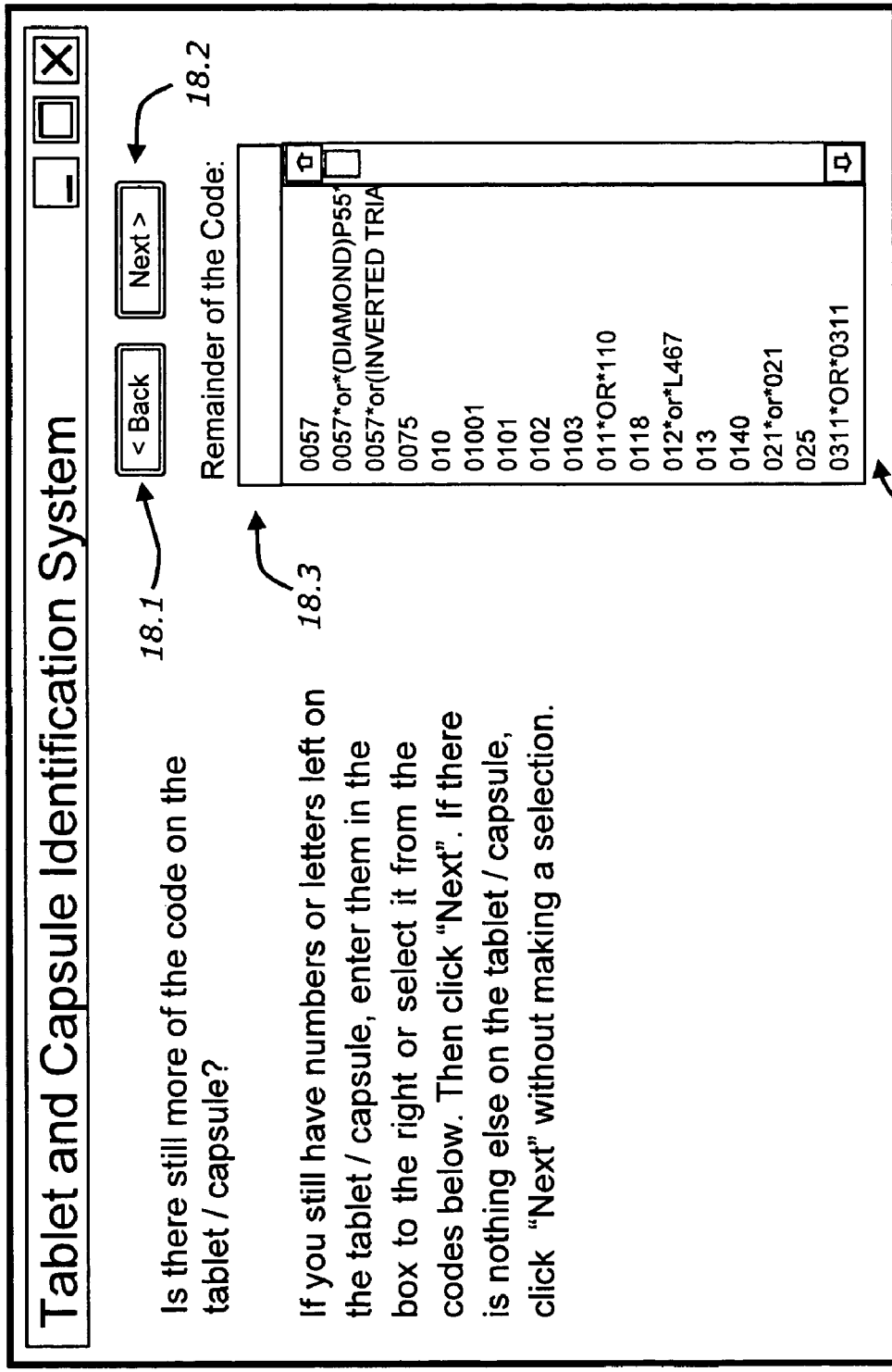
FIG. 18 is a screen shot illustrating a "Is there still more of the code (features) on the tablet/capsule?" screen that follows the screen of FIG. 13 upon designation of the next user option and also includes a remainder of the code input field, a scrollable remainder of the code list, a back user option and a next user option.

The method, routines and system of the present invention are demonstrated with an applicable database having a plurality of component classes (which may also be called basic informational components) and a plurality of associated descriptors that are commonly used in the art. Component classes include, by way of example, any of the following: a logo class, a numeric class, an alphabetic class and a remainder of the code class. An exemplary logo class is shown in FIG. 3 in the logo component class member array 3.4 through 3.35. An exemplary numeric class is shown in FIG. 8 and is presented in the scrollable list 8.4. An exemplary alphabetic class is shown in FIG. 13 and is presented in the scrollable list 13.4. An exemplary remainder of the code class is shown in FIG. 18 and is presented in the scrollable list 18.4.

The method, routines and system of the present invention originate from screen 2.0 of FIG. 2 which is the main screen and menu from which all next and back user options originate and to which they ultimately return. To initiate an identification of an imprint (code) on a dosage form using an exemplary computer program and an applicable data base, the user designates the imprint on tablet/capsule user option 2.7 of FIG. 2 which takes the user to screen 3.0 of FIG. 3.

Screen 3.0 of FIG. 3 illustrates "Does your tablet/capsule have a logo imprinted on it?" which was selected by designating an imprint on the tablet/capsule user option 2.7 of FIG. 2. Screen 3.0 also includes a back user option 3.1, a next user option 3.2, a selected logo number field 3.3, and a plurality of logos in the scrollable logo array 3.4 through 3.35.

Figure 4:
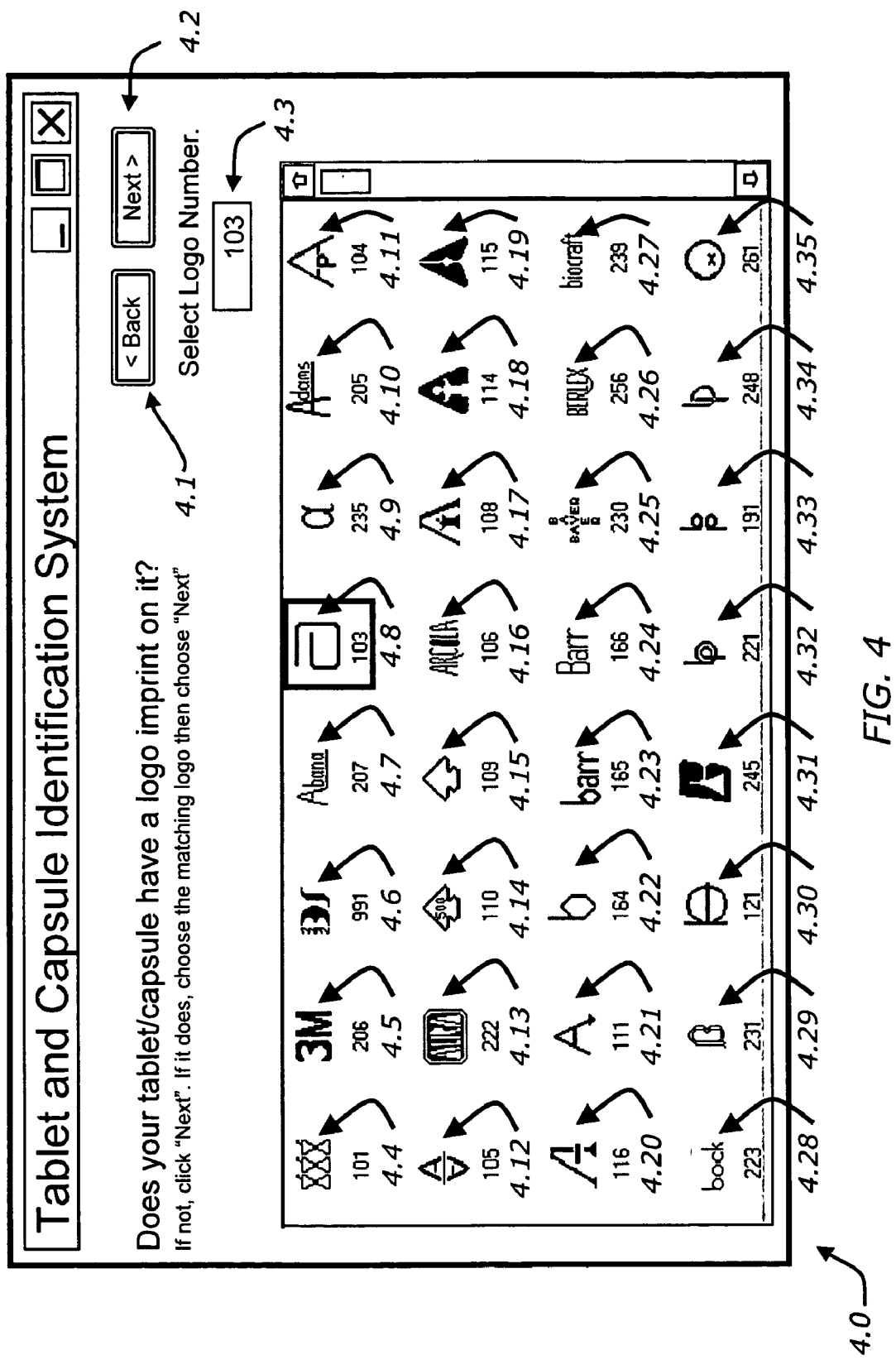
FIG. 4 is a screen shot illustrating "Does your tablet/capsule have a logo imprint on it?" screen with an identical scrollable logo array as in FIG. 3 and shows one of the logo component class members highlighted by a cursor positioning device and the logo number entered in the selected logo number input field and which screen also includes a back user option and a next user option.

A user looks at the dosage form that needs to be identified, determines that a feature of the imprint is a logo and compares the logo feature on the dosage form with the scrollable array of exemplary logo component class members 3.4 through 3.35. Once a match has been made, the logo number or other identifier is inputted into the selected logo number field, as illustrated next in field 4.3 of FIG. 4 in the present invention. The logo component class member 4.8 appears highlighted in screen 4.0 and the logo number 103 appears in the selected logo number input field 4.3. FIG. 4 also includes a back user option 4.1 and a next user option 4.2. The user is instructed to actuate the next user option 4.2 in FIG. 4, and the user is drawn to screen 5.0 in FIG. 5. For the identification of a dosage form without a logo feature, those options and routines are discussed subsequently.

Figure 5:
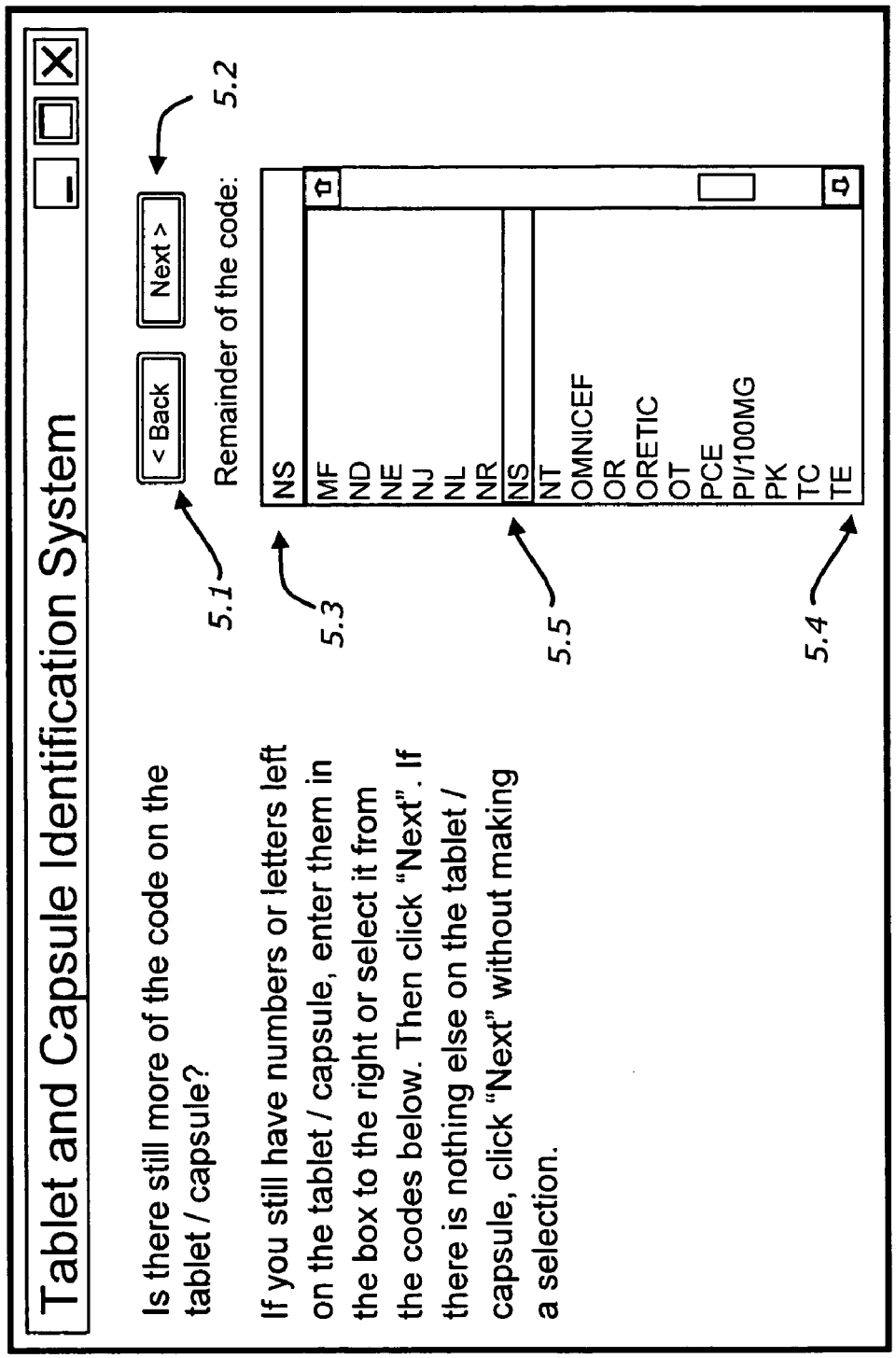
FIG. 5 is a screen shot illustrating a "Is there still more of the code (features) on the tablet/capsule?" screen that follows the screen of FIG. 4 upon designation of the next user option and further includes a remainder of the code input field, a remainder of the code list, both of which have been highlighted by a cursor positioning device for the remainder of the code component class member matching the remaining feature found on the dosage form of the current inquiry, a back user option and a next user option.

The remaining relevant feature in the imprint on the dosage form, associated with the exemplary logo component class member 4.8 in screen 4.0, is not found specifically in the numeric, alphabetical and the unqualified remainder of the code component class members respectively in FIGS. 8, 13 and 18. The user is systematically directed to screen 5.0 shown in FIG. 5 where only the associated remainder of the code component class members for the exemplary logo component class member is found. Screen 5.0 of FIG. 5 illustrates an "Is there still more of the code (features) on the tablet/capsule?" where two highlights, one in the remainder of the code user input field 5.3 and the other in the remainder of the code list 5.4, correspond to the remainder of the code component class member 5.5 and matches the remaining feature, as visualized by the user, on the exemplary tablet. Back user option 5.1 and a next user option 5.2 also appear in this screen 5.0.

It is appreciated that the remainder of the code list 5.4 appears as a unique set of component class members, derived from secondary features which correlate with only one of the logo component class members, derived from a unique primary feature, specifically the logo expressed as the component class member 4.8 in the scrollable logo array 3.4 through 3.35 of FIG. 3, by definition of primary and secondary imprint features. Through method of the present invention, relationship between a specific remainder of the code list and a specific logo component class member is a direct consequence of assessing imprint features into types, assigning them to respective component classes and maintaining further these relationships as a systematic requirement. It is further appreciated that the remainder of the code components may be only alphabetic or numeric in character since logo features are systematically maintained in, and accommodated by, the logo component class member array and may appear only in a single component class.

The user looks at the dosage form to determine if the imprint has any remaining features (code). A user reviews remainder of the code list 5.4 and matches a remainder of the code component class member with the remaining feature (code) appearing with the logo on the dosage form of interest. The matched remainder of the code 5.5 is highlighted using a cursor-positioning device and then inputted in the remainder of the code user field 5.4. Actuation of the next user option 5.2 on screen 5.0 brings up screen 6.0 of FIG. 6.

Figure 6:
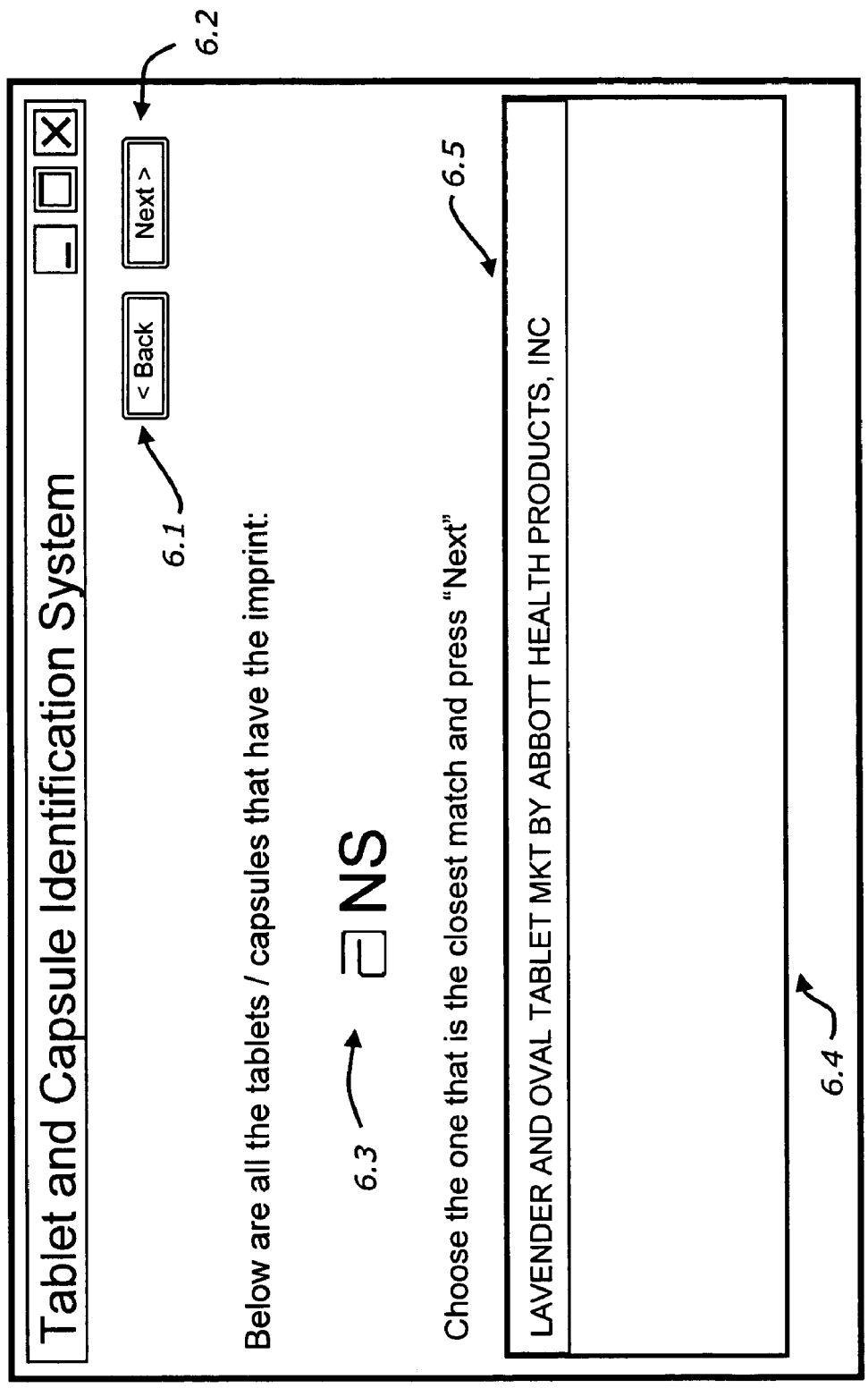
FIG. 6 is a screen shot illustrating a "Below are all the tablets/capsules that have the imprint" screen accessed by designating the next user option of FIG. 5 and also includes an imprint recap display, reconfirming positively the imprint on the dosage form for which the current inquiry is made, a physical and marketer descriptors display that appears in an array (Choose the one that is the closest match and press Next) and highlighted by a cursor positioning device, a next user option and a back user option.

In screen 6.0, as shown in FIG. 6, the logo component class member and remainder of the code component class member appear together in the imprint recap display 6.3, confirming a match has been found for the exemplary dosage form bearing the Abbott Laboratories logo feature and the remainder of the code feature NS. The array 6.4 itemizes the physical and marketer descriptors of dosage forms which bear the imprint of interest. The user agrees with the match between the physical and marketer descriptors display 6.5 and the appearance of the dosage form, highlights it using a cursor positioning device and actuates the next user option 6.2; had the user wished to return to the previous screen the back user option 6.1 may be actuated. The logo and remainder of the code component class members are displayed together in the Result screen 7.0 of FIG. 7.

FIG. 7. illustrates Result screen 7.0 accessed by designating next user option 6.2 of FIG. 6. This screen presents the results of various correlations of data inputs based upon routines and systems of the present invention. The tablet is marked as display 7.1 confirms that the dosage form of interest is a tablet, followed by the imprint recap display 7.2 which presents the imprint with both a graphical of the logo and text of remainder of the code component class members. Display 7.3 indicates a graphical representation of its physical appearance. The description display 7.4 indicates the descriptors that the tablet is lavender and oval. The NDC display 7.5 indicates an NDC number of 000746215XX. The generic name(s) display 7.6 indicates that the generic name of the dosage form is Divalproex Sodium 500 mg Delayed Relse. This product is marketed by display and user option 7.7 indicates that the tablet is marketed by Abbott Health Products Inc. The display and user option 7.7 may be clicked on by a cursor position device so that more information regarding the marketer can be supplied on a separate screen 28.0, FIG. 28. Legal status in the US display 7.11 indicates that the tablet is a prescription drug, but not a controlled substance. The special notes display 7.12 provides no special notes for this drug product at this time. It is commonly used display indicates that the tablet is used to treat convulsions 7.13. The route of administration display (It is commonly given orally) 7.16 specifies that the drug product is taken by mouth. Screen 7.0 also includes a return to main menu user option 7.17 and a fax it user option 7.18 which can provide a hard copy of screen 7.0 to an electronic printer or facsimile device.

Figure 9:
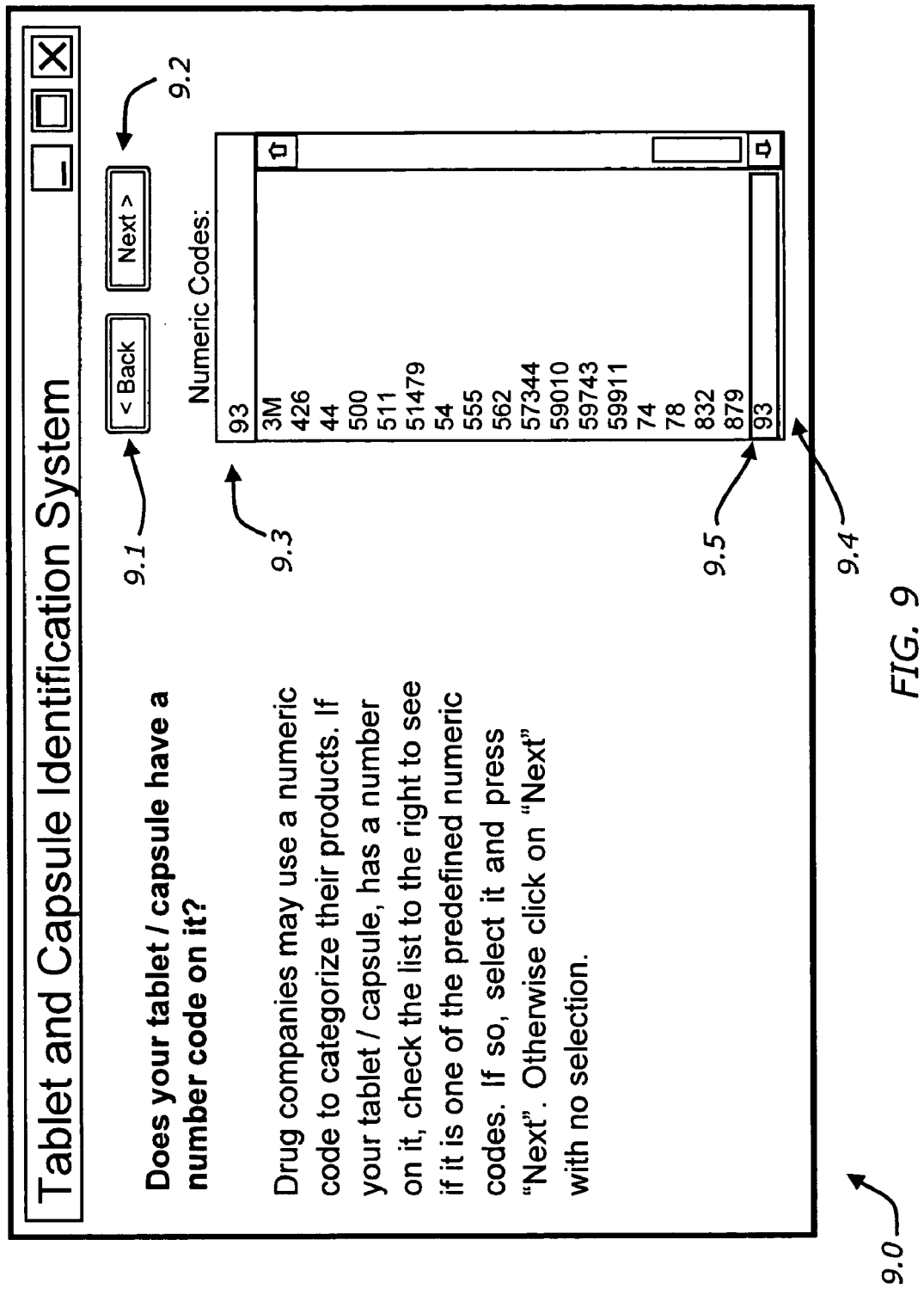
FIG. 9 is a screen shot illustrating a "Does your tablet/capsule have a number code (feature) on it?" screen in which a numeric code in FIG. 8 has been designated with a cursor positioning device and shows the resultant highlights in the numeric code input field and in the scrollable numeric code list and which screen also includes a back user option and a next user option.

Returning to FIG. 2, a user again designates user option 2.7 taking the user to screen 3.0 of FIG. 3. The user looks at another exemplary dosage form that needs to be identified and compares the imprint on the dosage form with the scrollable array of exemplary logo component class members 3.4 through 3.35 and observes that the imprint contains no logo feature to match. In the present invention, a user actuates the next user option 3.2 in screen 3.0 and attention is drawn to screen 8.0, FIG. 8. FIG. 8 illustrates "Does your tablet/capsule have a number code (feature) on it?" screen 8.0. The user then inspects the imprint on the dosage form to determine if it has a numeric feature. If the imprint does have an apparent numeric feature, then the user compares the imprint feature with the scrollable numeric codes list 8.4. In this example, a match is found for the exemplary numeric component class member 93 of an exemplary imprint 93 150 3 and further illustrated in FIGS. 31, 31.6. FIG. 9 illustrates screen 9.0 where the user has highlighted from FIG. 8 the numeric component class member 9.5 in the scrollable numeric codes list 9.4 and in the numeric codes input field 9.3, using a cursor positioning device. The user actuates the next user option 9.2 and the various routines of the present invention then associate or correlate the numeric component class member in numeric codes field 9.3 with remainder of the code component class members hierarchically inputted in an applicable database and derived from only secondary imprint features. The user arrives at screen 10.0, FIG. 10. Should users not find the numeric feature in the scrollable numeric codes list, users are instructed to click next user option 9.2. The fourth routine below makes the identification from remainder of the code component class members derived from tertiary imprint features.

Figure 10:
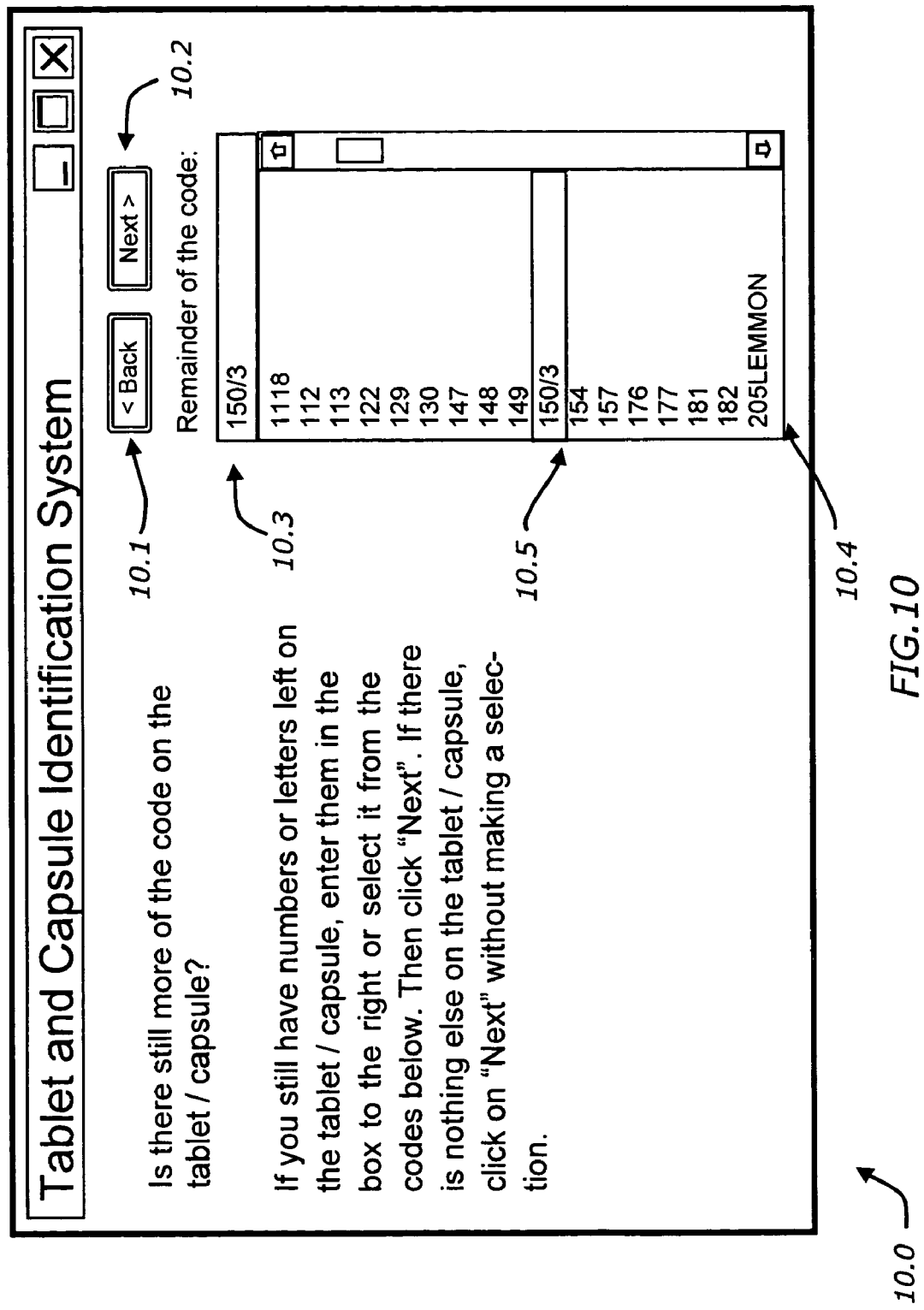
FIG. 10 is a screen shot illustrating an "Is there still more of the code (features) on the tablet/capsule?" screen that follows the screen of FIG. 9 upon designation of the next user option and further includes a remainder of the code input field, a remainder of the code list, in both of which the remainder of the code component class member has been highlighted for the remaining feature of the imprint on the dose form of the current inquiry using a cursor positioning device, a back user option and a next user option.

FIG. 10 illustrates "Is there still more of the code (features) on the tablet/capsule?" screen 10.0. A user reviews the remaining feature 150 3 on the dosage form, finds a match in the remainder of the code list 10.4 which appears as 150/3, and highlights component class member 10.5 using a cursor positioning device. The matched remainder of the code component class member is then entered in remainder of the code input field 10.3. Actuation of the next user option 10.2 brings up FIG. 11 screen 110.

It is appreciated that the remainder of the code list 10.4 appears as a unique set of remainder of the code component class members, derived from secondary features, which correlate with only one numeric component class member, derived from a unique primary feature, in the numeric codes list 8.4 of FIG. 8, by definition of primary and secondary imprint feature types. Relationship between the components of a specific remainder of the code list and a specific numeric component class member is a direct consequence of the method in the present invention. Consequently tertiary features may only appear in the fourth routine.

Figure 11:
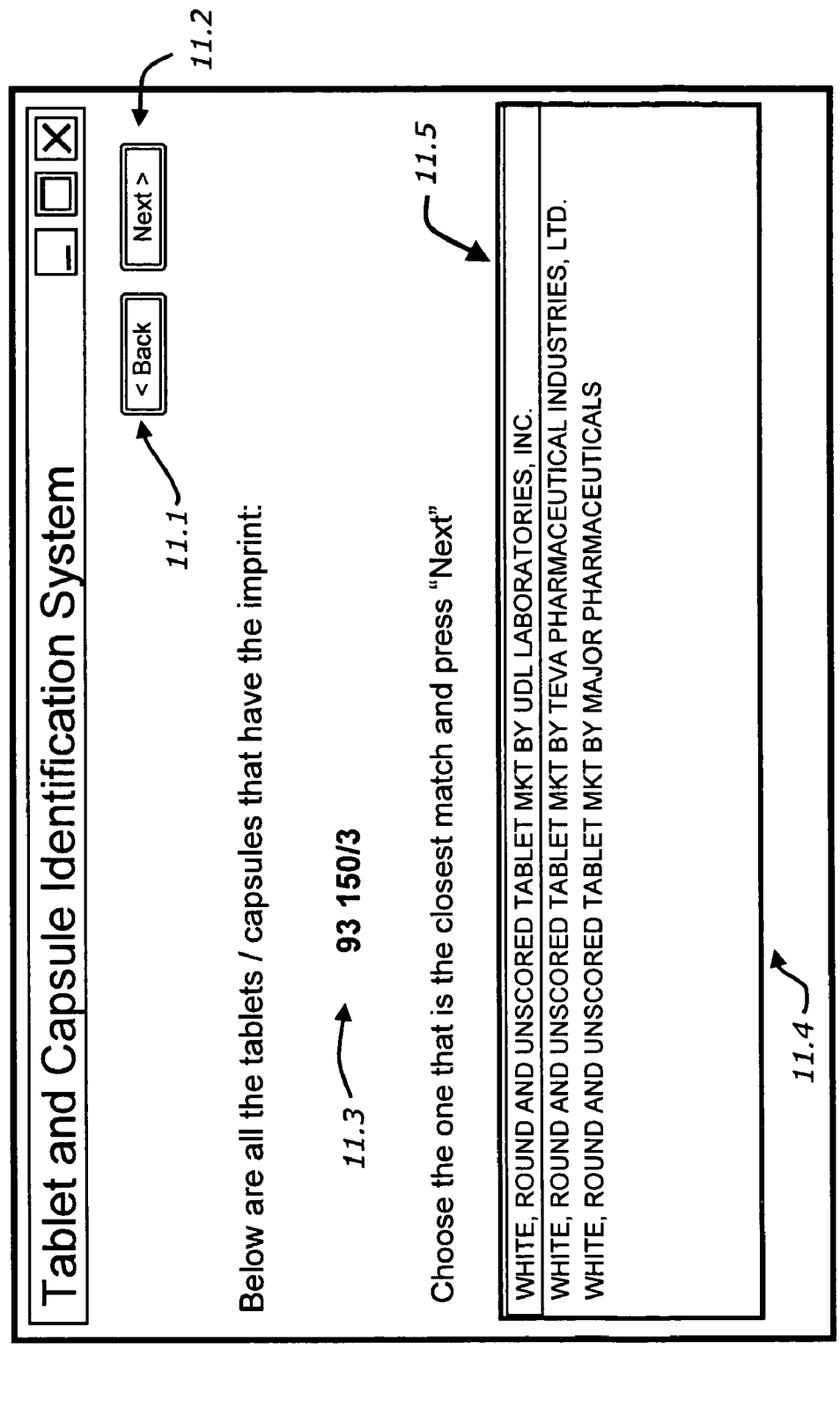
FIG. 11 is a screen shot illustrating a "Below are the tablets/capsules that have the imprint:" screen accessed by designation of the next user option in FIG. 10 and also includes an imprint recap display, reconfirming positively the imprint on the dosage form for which the current inquiry is made and physical and marketers descriptors displays that appear in an array (Choose the one that is the closest match and press Next), one of which descriptors displays is highlighted using a cursor positioning device, a next user option and a back user option.

In screen 11.0, FIG. 11, the numeric and remainder of the code component class members appear together in the imprint recap display 11.3, confirming a match has been found for the imprint on the dosage form of interest. The array 11.4 itemizes the physical and marketer descriptors of dosage forms which bear the imprint on the dosage form. The user agrees with the match between the physical and marketer descriptors display 11.5 and the appearance of the dosage form, highlights it using a cursor positioning device and actuates the next user option 11.2; had the user wished to return to the previous screen the back user option 11.1 may be actuated. The numeric and remainder of the code component class members are displayed together in the Result screen 12.0 of FIG. 12.

FIG. 12 illustrates Result screen 12.0 accessed by designating next user option 11.2 of FIG. 11. This screen presents the results of various correlations of data inputs based upon routines and systems of the present invention. The tablet is marked as display 12.1 confirms that the dosage form of interest is a tablet, followed by the imprint recap display 12.2 which presents the numeric component class member and the remainder of the code component class member as text, confirming a positive identification of the dosage form of interest as displayed in Example 2, FIG. 31. It looks like display 12.3 indicates a graphical representation of its physical appearance. The description display 12.4 indicates the descriptors that the tablet is white, round and unscored. The NDC display 12.5 indicates an NDC number of 510790161XX. The generic name(s) display 12.6 indicates that the generic name of the tablet is Acetaminophen 300 Codeine Phosphate 30 mg. This product is marketed by display and user option 12.7 which indicates that the tablet is marketed by UDL Laboratories Inc. and is equivalent to display 12.9 indicates that the tablet is generically equivalent to the trademarked product Tylenol #3™. A trademark of display and user option 12.10 names the trademark holder as McNeilab Inc. The displays and user options 12.7 and 12.10 may be clicked on by a cursor position device so that more information regarding the marketer can be supplied on a separate screen 28.0, FIG. 28. Legal status in the US display 12.11 indicates that the tablet is a schedule 3 controlled substance—Rx is required. The special notes display 12.12 provides no special notes for this drug product at this time. It is commonly used display indicates that the tablet is used to relieve moderate to severe pain 12.13 and to relieve fever 12.14. The route of administration display 12.16 (It is commonly given orally) specifies that the drug product is given orally. Screen 12.0 also includes a return to main menu user option 12.17 and a fax it user option 12.18 which can provide a hard copy of screen 12.0 to an electronic printer or facsimile device.

Repeating the routine a third time, the user designates user option 2.7 of FIG. 2 taking the user to FIG. 3, screen 3.0. The user looks at yet another dosage form that needs to be identified and compares the imprint on the dosage form with the scrollable array of exemplary logo component class members 3.4 through 3.35 but finds no logo feature in the imprint to match. In the present invention, a user actuates the next user option 3.2 in screen 3.0 and attention is drawn to screen 8.0, FIG. 8. FIG. 8 illustrates "Does your tablet/capsule have a number code (feature) on it?" screen. The user again inspects the dosage form to determine if the imprint on it has a numeric feature but finds no numeric component class member in the respective numeric codes list 8.4 to match. A user actuates the next user option 8.2 in screen 8.0 and attention is drawn to screen 13.0, FIG. 13. The imprint feature 200, when associated with primary feature type BRA, by definition is a secondary feature type and may not be listed among the primary features displayed as component class members in the numeric codes list 8.4.

Figure 14:
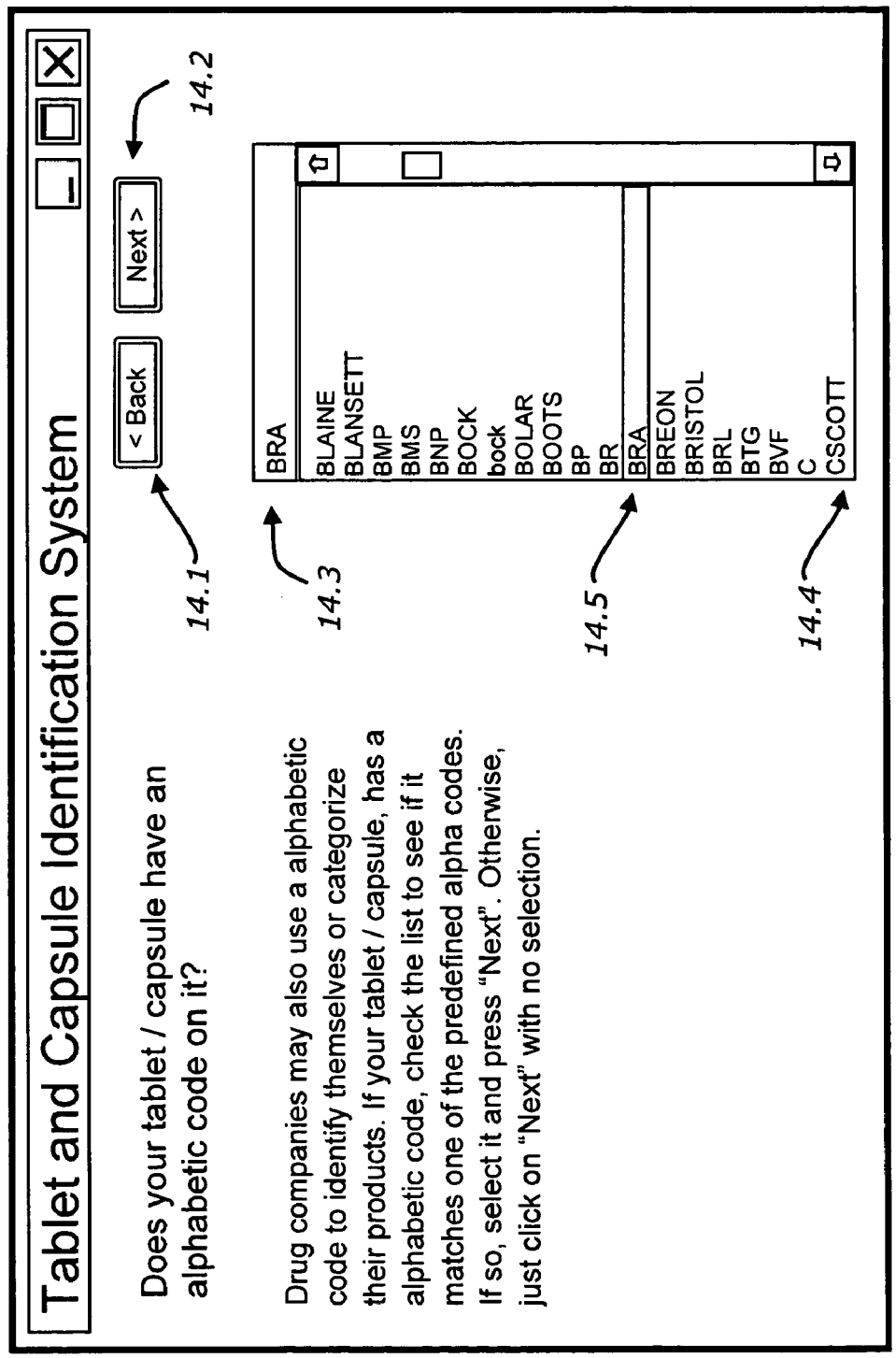
FIG. 14 is a screen shot illustrating a "Does your tablet/capsule have an alphabetic code (feature) on it?" screen in which an alphabetic code in FIG. 13 has been designated with a cursor positioning device and shows the resultant highlights in the alphabetic code input field and in the scrollable alphabetic code list and which screen also includes a back user option and a next user option.

FIG. 13 illustrates a "Does your tablet/capsule have an alphabetic code (feature) on it?" screen 13.0. In this routine the user determines if the imprint has an alphabetic feature and compares the imprint features, as displayed in FIGS. 31, 31.7, with scrollable alphabetic component class members in list 13.4. The user highlights the matching alphabetic component class member BRA in the scrollable list, using a cursor positioning device, enters the alphabetic component class member into alphabetic codes input field 13.3. For the exemplary imprint BRA 200, composed of both an alphabetic feature BRA and a remainder of the code feature 200, FIG. 14 illustrates screen 14.0 where the alphabetic component class member BRA, 14.5, appears highlighted by the prospective user using a cursor positioning device in both the scrollable alphabetic codes list 14.4 and in the alphabetic codes user input field 14.3. The user then actuates the next user option 14.2 to move to screen 15.0, FIG. 15. The various routines of the present invention then associate or correlate the alphabetic component class member in the alphabetic codes field 14.3 with remainder of the code component class members hierarchically inputted in an applicable database.

Figure 15:
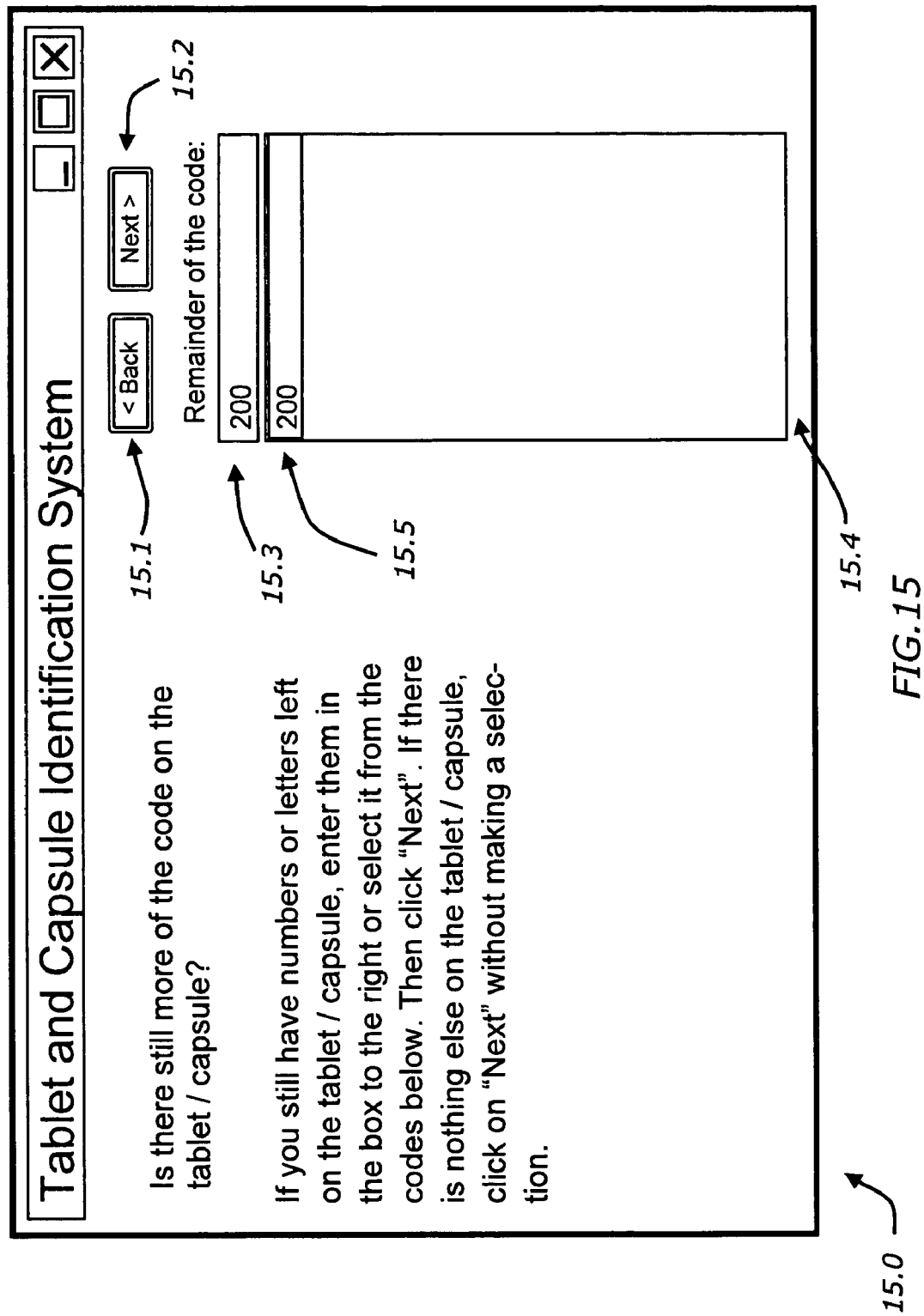
FIG. 15 is a screen shot illustrating a "Is there still more of the code (features) on the tablet/capsule?" screen that follows the screen of FIG. 14 upon designation of the next user option and also includes a remainder of the code input field and a remainder of the code list, both of which have been highlighted using a cursor positioning device for the remainder of the code component class member matching the remaining feature found on the dosage form of the current inquiry, a next user option and a back user option.

FIG. 15 illustrates "Is there still more of the code (features) on the tablet/capsule?" screen 15.0. Screen 15.0 includes a remainder of the code input field 15.3, a scrollable remainder of the code list 15.4, a back user option 15.1 and a next user option 15.2. The user looks at the dosage form to determine if the imprint has any remaining features on it, which is in this example the secondary feature 200 which is not included among primary features in the numeric class in an applicable database. The remaining feature on the dosage form in the scrollable remainder of the code list 15.4 presents as a secondary feature and remainder of the code component class member. The matched remainder of the code component class member 15.5 is highlighted in both the remainder of the code list 15.4, by the prospective user using a cursor positioning device, and in the remainder of the code input field 15.3, as illustrated in FIG. 15, screen 15.0. Actuation of the next option 15.2 on screen 15.0 brings up screen 16.0, FIG. 16.

It is appreciated that the scrollable remainder of the code list 15.4 appears as a unique set of component class members, derived from secondary features, which correlate with only one alphabetic component class member, derived from a unique primary feature, in the alphabetic codes list 13.4 of FIG. 13, by definition of primary and secondary imprint feature types. The relationship between the components of a specific remainder of the code list and a specific alphabetic component class member is a direct consequence of method in the present invention.

Figure 16:
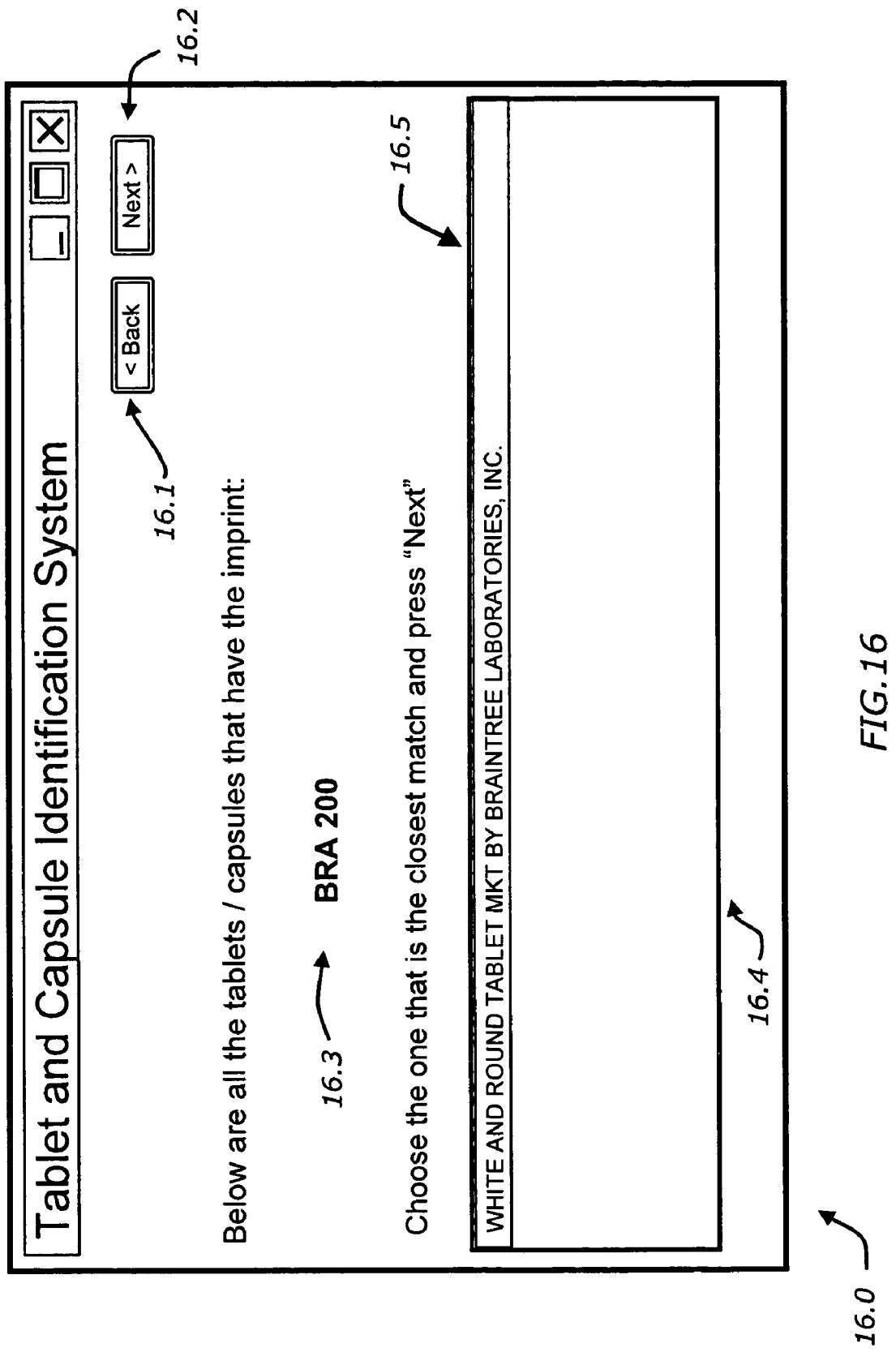
FIG. 16 is a screen shot illustrating a "Below are all the tablets/capsules that have the imprint" screen accessed by designating the next user option of FIG. 15 and also includes an imprint recap display, reconfirming positively the imprint on the dosage form for which the current inquiry is made, a physical and marketer descriptors display that appears in an array (Choose the one that is the closest match and press Next) and highlighted by a cursor positioning device, a next user option and a back user option.

Screen 16.0 of FIG. 16 illustrates "Below are all the tablet/capsules that have the imprint" BRA 200, appearing in field 16.3, confirming a match has been found in the present invention. The array 16.4 itemizes the physical and marketer descriptors display 16.5 of the dosage form which bears the imprint of interest. The user agrees with the match between the physical and marketer descriptors display 16.5 and the appearance of the dosage form, highlights it using a cursor positioning device and actuates the next user option 16.2; had the user wished to return to the previous screen the back user option 16.1 may be actuated. The alphabetic and remainder of the code component class members are displayed together in the Results screen 17.0.

FIG. 17 illustrates a Result screen 17.0 accessed by designating next user option 16.2 of FIG. 16. This screen presents the results of various correlations of data inputs based upon routines and systems of the present invention. The tablet is marked as display 17.1 confirms that the dosage form of interest is a tablet, followed by the imprint recap display 17.2 which presents both the alphabetic and remainder of the code component class members textually as BRA 200. It looks like display 17.3 indicates a graphical. representation of its physical appearance. The description display 17.4 indicates that the tablet is white and round. The NDC display 17.5 indicates an NDC number of 522680200XX. The generic name(s) display 17.6 indicates that the generic name of the tablet is Calcium Acetate 667 mg. This product is marketed by display and user option 12.7 indicates that the tablet is marketed by Braintree Laboratories Inc. And is equivalent to display 17.9 indicates that the tablet is generically equivalent to the trademarked product Phoslo™. A trademark of display and user option 17.10 names the trademark holder as Braintree Laboratories Inc. The displays and user options 17.7 and 17.10 may be clicked on by a cursor position device so that more information regarding the marketer can be supplied on a separate screen 28.0, FIG. 28. Legal status in the US display 17.11 indicates that the tablet is a prescription drug, but not a controlled substance. The special notes display 17.12 provides no special notes for this drug product at this time. It is commonly used display indicates that the tablet is used to provide sugar and/or salts in the blood 17.13. It is commonly given orally display 17.16 indicates that the tablet is taken by mouth. Screen 17.0 also includes a return to main menu user option 17.17 and a fax it user option 17.18 which can provide a hard copy of screen 17.0 to an electronic printer or facsimile device.

Repeating the routine a fourth and last alliteration, the user designates user option 2.7, FIG. 2. The user looks at a fourth dosage form that needs to be identified and compares the imprint on the dosage form, as displayed in FIGS. 31, 31.8, with the list of exemplary logo component class members 3.4 through 3.35 but finds no logo feature to match. In the present invention, a user actuates the next user option 3.2 in screen 3.0 and attention is drawn to screen 8.0, FIG. 8. FIG. 8 illustrates "Does your tablet/capsule have a number code (feature) on it?" screen 8.0. The user again inspects the dosage form to determine if it has a numeric feature which matches a numeric component class member in the scrollable numeric codes list 8.4 but finds no numeric component class member matching imprint feature(s) on the dosage form. In the present invention a user actuates the next user option 8.2 in screen 8.0 and is drawn to FIG. 13. The feature 230 is a tertiary feature type and is not included as component class members in the scrollable list 8.4 derived from primary features in the present routine; consequently it may not be found here.

FIG. 13 illustrates a "Does your tablet/capsule bear an alphabetic code (feature) on it?" screen 13.0. A user in this example, inspecting the dosage form, finds no match. On actuation of next user option 13.2, the user arrives at FIG. 18, the fourth and last routine that assesses imprint features on dosage forms.

FIG. 18 illustrates an "Is there still more of the code (features) on the tablet/capsule?" screen 18.0. Screen 18.0 prompts the user to examine the dosage form to determine if there is any remaining features that match any qualified remainder of the code component class members in the scrollable remainder of the code list 18.4. The user finds a match by scrolling the remainder of the code list 18.4 for the remainder of the code component class member that is 230.

It is appreciated that scrollable remainder of the code list 18.4 is generated by the routines of the present invention based upon the preceding inputs so that list 18.4 contains a subset of remainder of the codes component class members, exclusive of any association with logo, numeric and alphabetic (and any other classes of import) components. These remainder of the code component class members at this point in the routine and in the scrollable list 18.4 have no other component class members hierarchically associated with them, and by definition are tertiary imprint features after the method of this invention. The serial exclusion of logo, numeric and alphabetic component class members, derived from primary and secondary imprint features, measurably improves the efficiency and precision of the search in this fourth routine. The improvement in search precision is a novel attribute of the present invention since the remainder of the code component, derived from a tertiary imprint feature, can be now solely used to make a positive identification.

Figure 19:
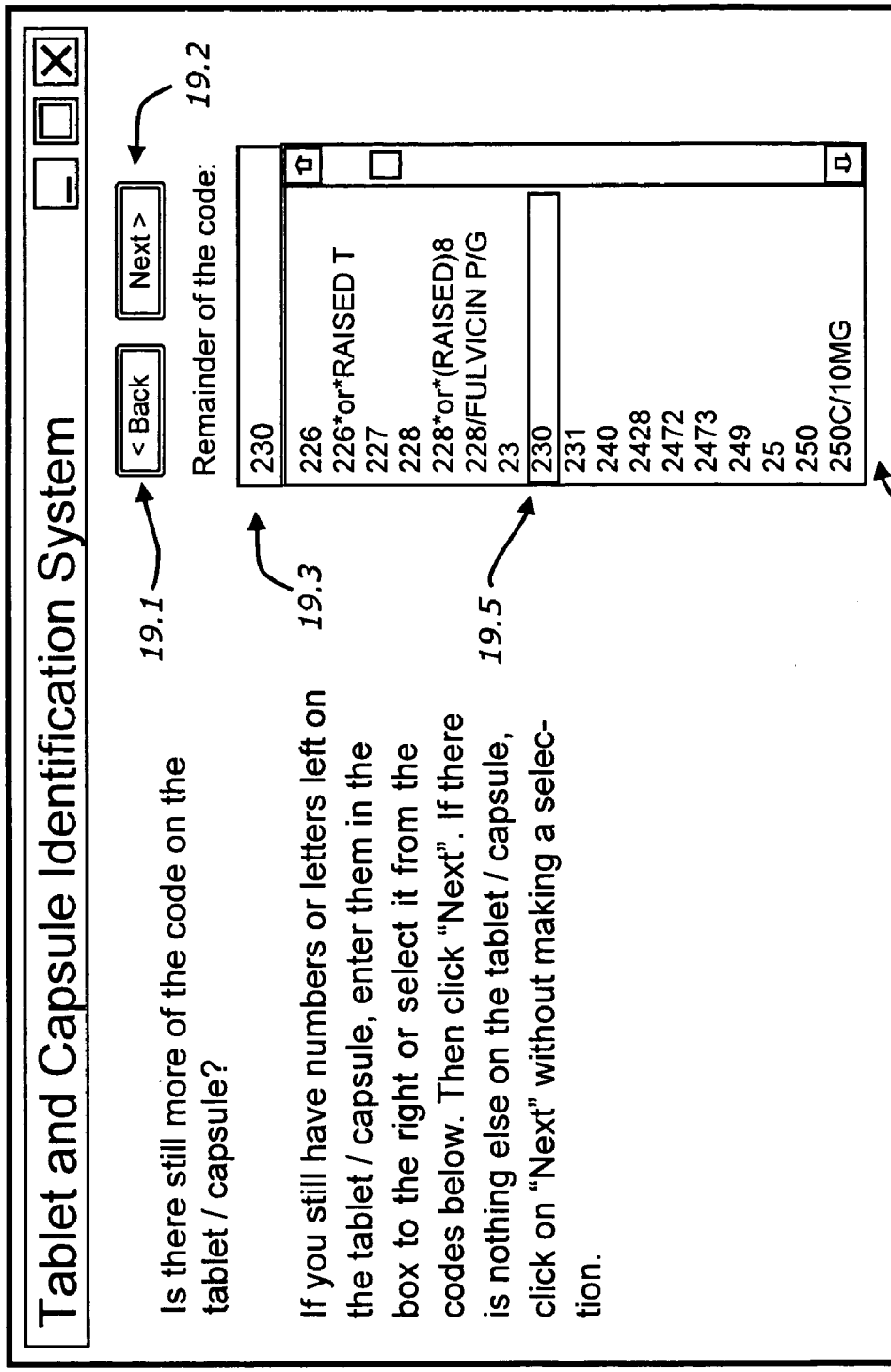
FIG. 19 is a screen shot illustrating "Is there still more of the code (features) on the tablet/capsule?" screen in which a remainder of the code component class member in FIG. 18 has been designated and highlighted in the remainder of the code input field and in the scrollable remainder of the code list by a cursor positioning device and which screen further includes a back user option and a next user option.

In screen 19.0 of FIG. 19 the remainder of the component class member 230 is shown highlighted both in the remainder of the code input field 19.3 and in the scrollable remainder of the code list 19.4. The user then actuates next user option 19.2.

Upon actuating next user option 19.2, FIG. 19, for the exemplary remainder of the code component class member 230, FIG. 20 appears and illustrates "Below are all the tablet/capsules that have the imprint:" and the component class member 230 appears in the imprint recap display 20.3. The array 20.4 itemizes the physical and marketer descriptors displays of dosage forms which bear the imprint. The user agrees with the match between the physical and marketer descriptors display 20.5 and the appearance of the dosage form, highlights it with a cursor positioning device and actuates the next user option 20.2. The remainder of the code component class member 230 appears in the Results screen 21.0, FIG. 21.

Figure 20:
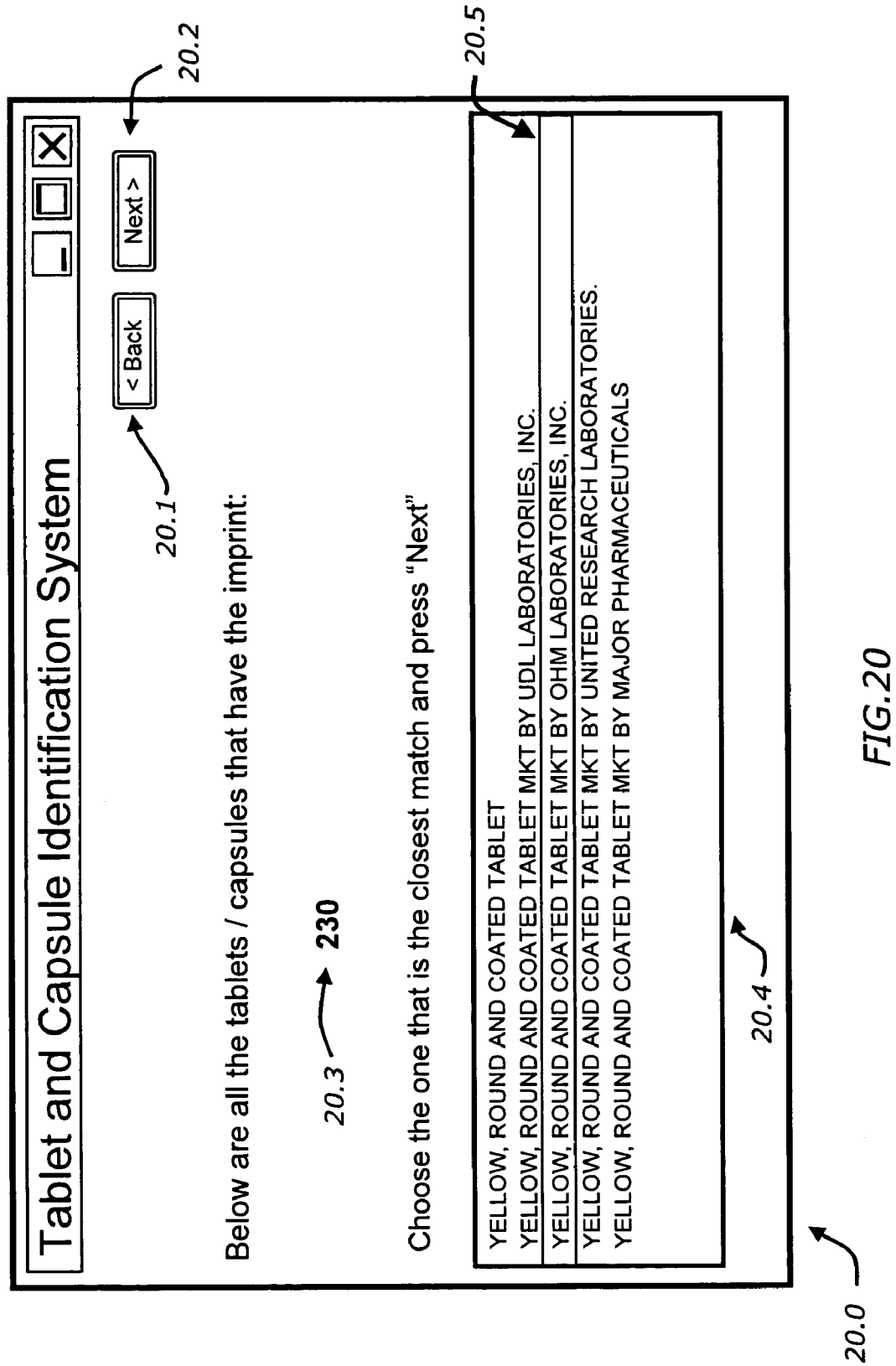
FIG. 20 is a screen shot illustrating a "Below are all the tablets/capsules that have the imprint" screen accessed by designating the next user option of FIG. 19 and also includes an imprint recap display, reconfirming positively the imprint on the dosage form for which the current inquiry is made, physical and marketer descriptors displays that appear in an array (Choose the one that is the closest match and press Next), one of which descriptors displays is highlighted by a cursor positioning device, a next user option and a back user option.

FIG. 21 illustrates a Result screen 21.0 accessed by designating next user option 20.2 of FIG. 20. This screen presents the results of various correlations of data inputs based upon routines and systems of the present invention. The tablet is marked as display 21.1 confirms that the dosage form of interest is a tablet, followed by the imprint recap display 21.2 which presents the component class member 230 textually and confirms that a positive identification has been made using an exemplary database and computer programs. It looks like display 21.3 indicates the shape of the tablet with a graphical representation of its physical appearance. The description display 21.4 indicates that the tablet is yellow, round and coated. The NDC display 21.5 indicates an NDC number of 516600230XX. The generic name(s) display 21.6 indicates that the generic name of the tablet is Bisacodyl 5 mg Enteric Coated. This product is marketed by display and user option 21.7 indicates that the tablet is marketed by Ohm Laboratories Inc. And is equivalent to display 21.9 indicates that the tablet is equivalent to Dulcolax™ and is a trademark of Ciba Self Medication Inc which is indicated in the display and user option 21.10. The displays and user options 21.7 and 21.10 may be clicked on providing more information regarding the company on a separate screen 28.0, FIG. 28. Legal status in the US display 21.11 indicates that the tablet is an over-the-counter drug (OTC). The special notes display 21.12 provides no special notes for this drug product at this time. It is commonly used display indicates that the tablet is used to relieve constipation and to move the bowels 21.13. The route of administration (It is commonly given orally) is the display 21.16. Screen 21.0 also includes a return to main menu user option 21.17 and a fax it user option 21.18 which can provide a hard copy of screen 21.0 to an electronic printer or facsimile device.

Figure 22:
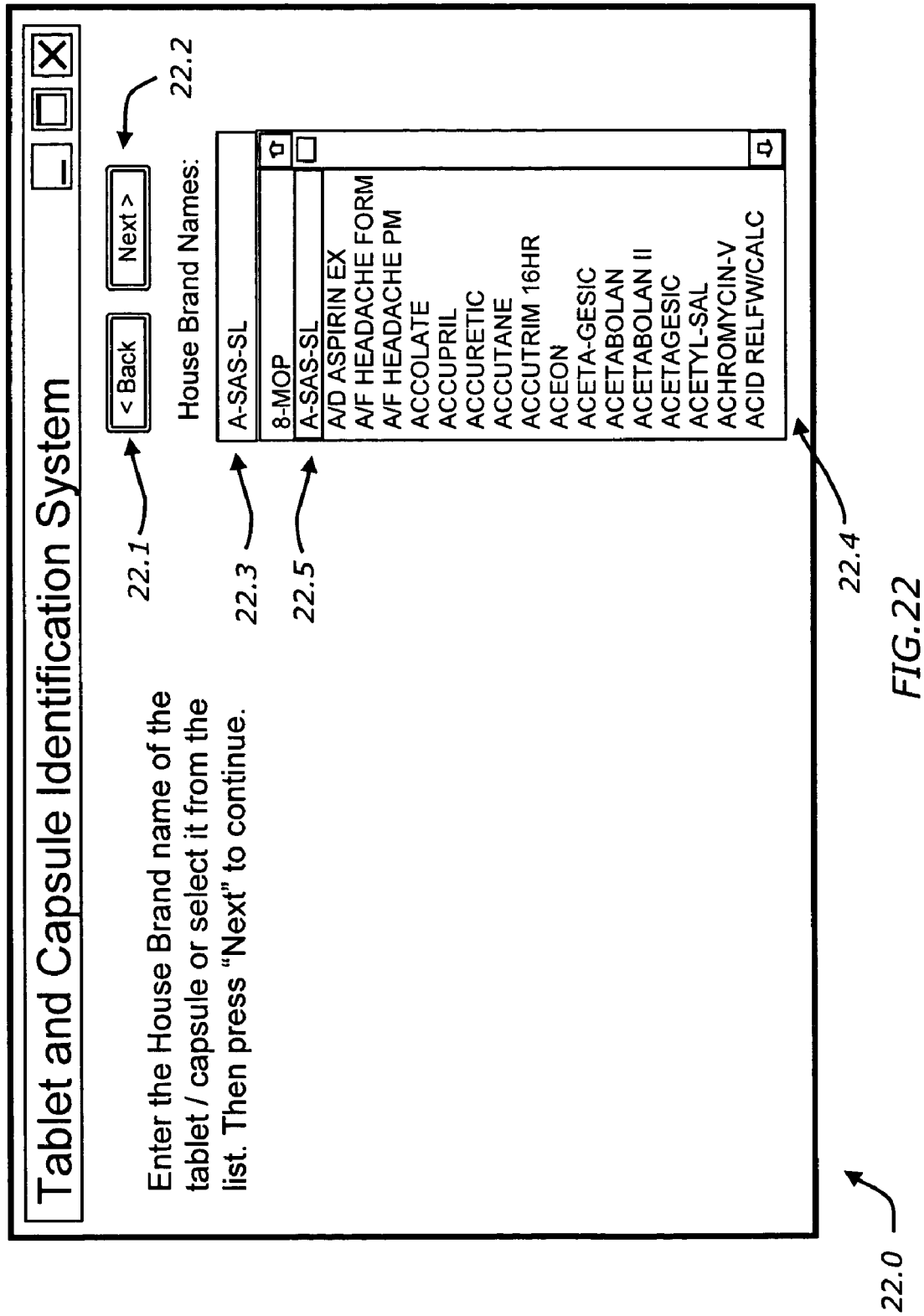
FIG. 22 is a screen shot illustrating an "Enter the house brand name." screen, accessed by designating house brand name user option of FIG. 2, in which a highlighted brand name using a cursor positioning device appears in a house brand names input field and scrollable house brand names list and further includes a back user option and a next user option.

In the present invention the user may access information about a drug product, not only by imprint on the dosage form, but also by name of the house brand from the graphical user interface of FIG. 2. The user presumptively has a prescription container bearing the name of, or has an interest in, a branded drug product. The user designates user option 2.8, FIG. 2, taking the user to FIG. 22. FIG. 22 illustrates the "Enter the House Brand name of the tablet/capsule." screen 22.0. The user scrolls through the house brand names list 22.4 until the branded drug product A-SAS-SL appears, highlights the descriptor matching the brand name 22.5 with a cursor positioning device and enters the house brand name into house brand input name field 22.3. FIG. 22, Screen 22.0 includes also a back user option 22.1 and a next user option 22.2. The user then actuates next user option 22.2. By the selection of the house brand name and the actuation of user option 22.2, the user arrives at screen 23.0 on FIG. 23.

Figure 23:
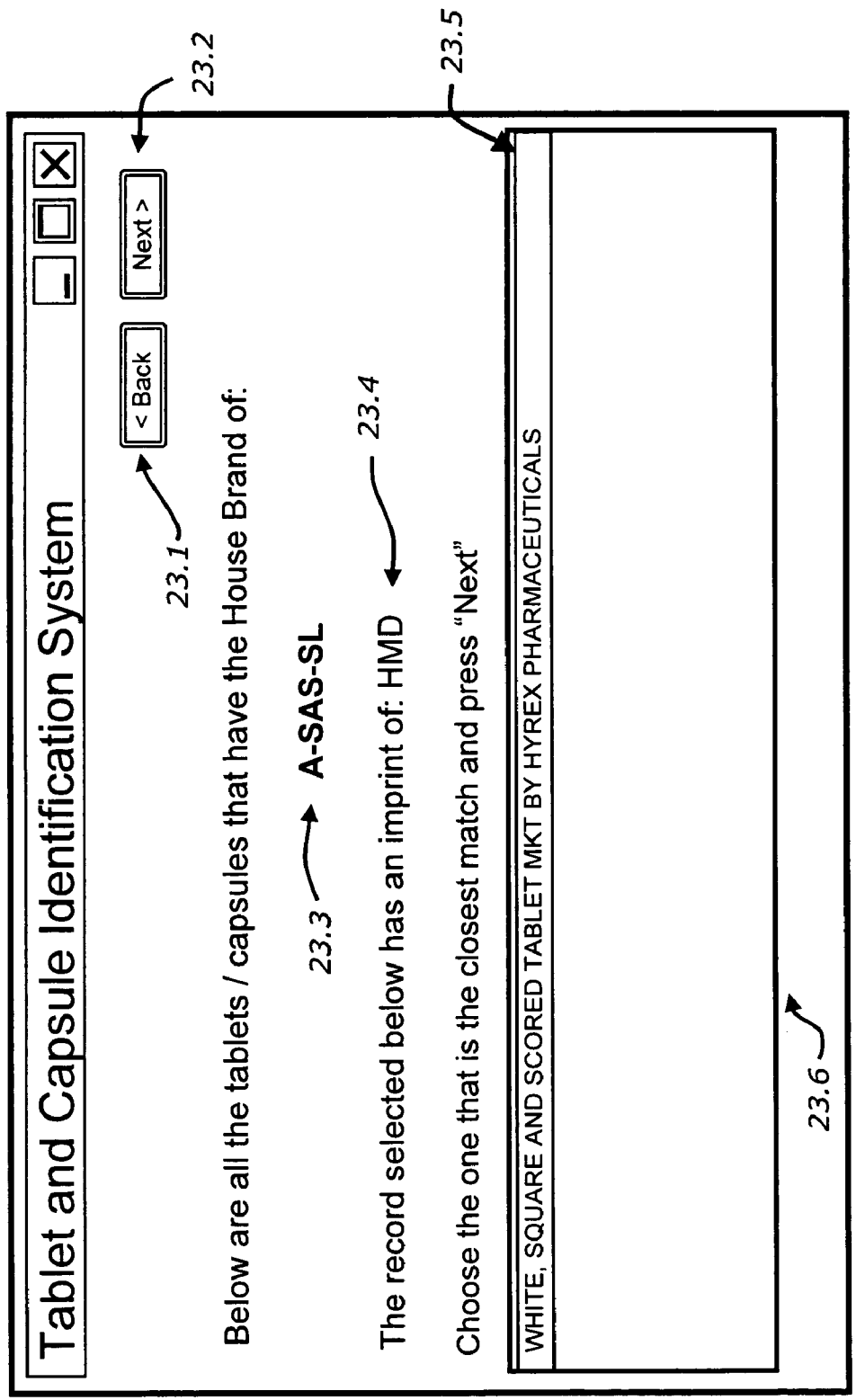
FIG. 23 is a screen shot illustrating a "Below are all the tablets/capsules that have the House Brand of" screen accessed by designating the next user option of FIG. 22, followed by the display of the house brand name of the exemplary drug product in the current inquiry, an imprint recap display (The record selected below has an imprint of), confirming a positive identification of the imprint of the branded drug product, physical identification descriptors that appear in a field (Choose the one that is the closest match and press Next) which is highlighted by a cursor positioning device, a next user option and a back user option.

FIG. 23 illustrates "Below are all the tablets/capsules that have the House Brand of:" screen 23.0 and includes a display 23.3 which in the example confirms the house brand name of A-SAS-SL™ and the record selected below has an imprint of display 23.4 which presents the remainder of the code component class member of the exemplary branded product as HMD and confirms a positive identification of the dosage form for the branded product. The user then is directed to a selectable match array 23.6 to select an option in this field. In the example given, the option 23.5 is listed with descriptors as "white square and scored tablet marketed by Hyrex pharmaceuticals" and is shown highlighted by a cursor-positioning device. The user is then directed to press next user option 23.2; user option 23.1 is a back option. Upon pressing next user option 23.2 the user is then presented with screen 24.0 of FIG. 24.

FIG. 24 illustrates a Result screen 24.0 accessed by designating next user option 23.2 of FIG. 23. This screen presents the results of various correlations of data inputs based hierarchically upon routines and systems of the present invention. The tablet is marked as display 24.1 confirms that the dosage form of interest is a tablet, followed by the imprint recap display 24.2 which presents the remainder of the code component class member HMD textually. It looks like display 24.3 indicates descriptors that the tablet has the shape of a square with a single score and displays a graphical representation of its physical appearance. The description display 24.4 indicates that the tablet is white, square and scored. The NDC display 24.5 indicates an NDC number of 003140011XX. The generic name(s) display 24.6 indicates that the generic name of the tablet is Hyoscyamine Sulfate 0.125 mg oral/sl. This product is marketed by display and user option 24.7 indicates that the tablet is marketed by Hyrex Pharmaceuticals. Under the trademark display 24.8 indicates that the tablet has a trademark of A-sas-sl™. And is equivalent to display 24.9 indicates that the tablet is equivalent to Levinex SL™ and is a trademark of Hyrex Pharmaceuticals which is indicated in the display and user option 24.10. The displays and user options 24.7 and 24.10 may be clicked on providing more information regarding the company on a separate screen 28.0, FIG. 28. Legal status in the US display 24.11 indicates that the tablet is a prescription drug, but not a controlled substance. The special notes display 24.12 provides no special notes for this drug product at this time. It is commonly used display indicates that the tablet is used to relax spasms of or to stimulate the urinary tract 24.13 and to treat stomach conditions 24.14. The route of administration (It is commonly given orally) display 24.16 indicates that the drug product is taken orally. Screen 24.0 also includes a return to main menu user option 24.17 and a fax it user option 24.18, which can provide a hard copy of screen 24.0 to an electronic printer or facsimile device.

In the present invention the user may access information for a drug product from the graphical user interface of FIG. 2, not only by the imprint on the dosage form and by house brand name but also by the National Drug Code (NDC) using applicable computer. programs and database. A user presumptively has an interest in an exemplary NDC, whether it be associated with a written prescription order, prescription label or found on the label of a branded product, but not limited to these examples alone. The user designates user option 2.9, FIG. 2 and is drawn to screen 25.0 of FIG. 25.

Figure 25:
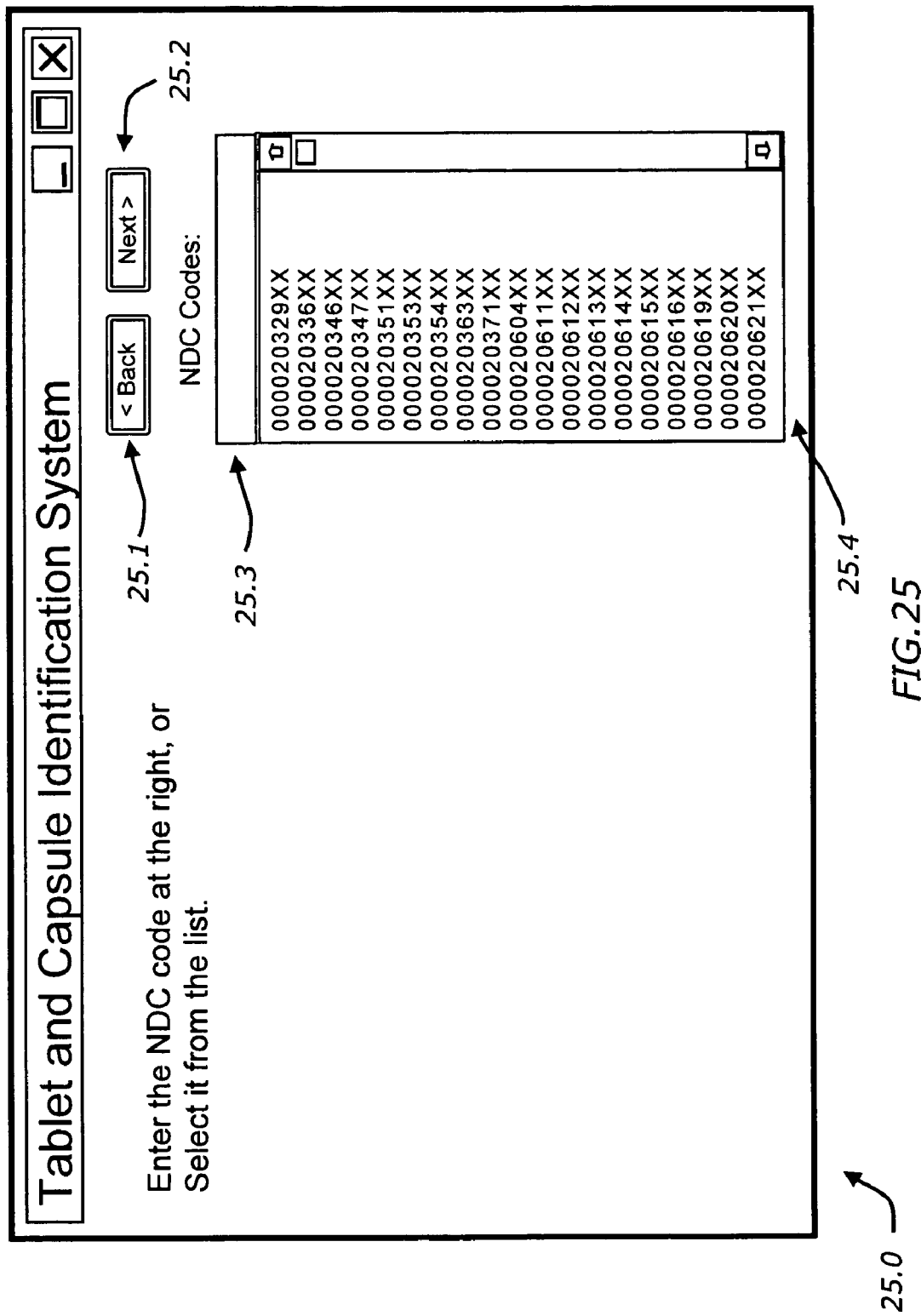
FIG. 25 is a screen shot illustrating an "Enter the NDC code at the right or select it from the list" screen accessed by designating national drug code (NDC) user option on FIG. 2 and also includes a NDC Codes input field, a scrollable NDC codes list, a back user option and a next user option.
Figure 26:
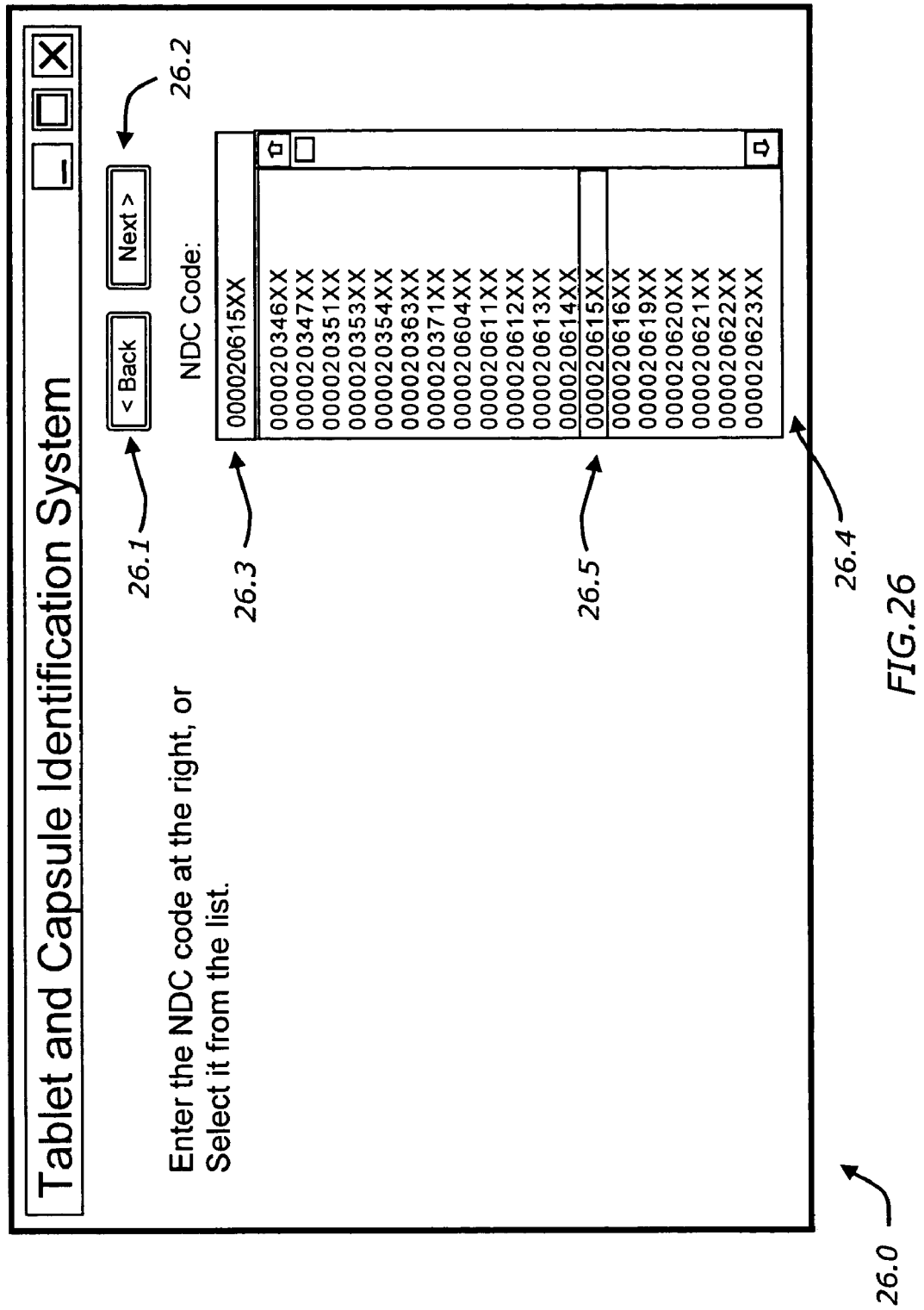
FIG. 26 is a screen shot illustrating an "Enter the NDC code at the right or select it from the list" screen in which an exemplary NDC code in FIG. 25 has been designated and highlighted in the NDC code input field and in the scrollable NDC code list using a cursor positioning device and which screen also includes a back user option and a next user option.

FIG. 25 illustrates an "Enter the NDC code at the right or select it from the list" screen 25.0 accessed by designating user option 2.9 and the next user option of FIG. 2. The NDC may be designated in the NDC codes list 25.4 by scrolling to the exemplary NDC arranged numerically or it can be inputted into NDC codes input field 25.3. Screen 26.0 of FIG. 26 illustrates the highlighting of the exemplary NDC 000020615XX as descriptor 26.5 in the scrollable NDC Codes list 26.4, using a cursor positioning device, and its entry in NDC Codes input field 26.3. The user may either actuate back user option 26.1 or next user option 26.2. If next user option 26.2 is actuated, then the user is presented with screen 27.0 of FIG. 27.

Figure 27:
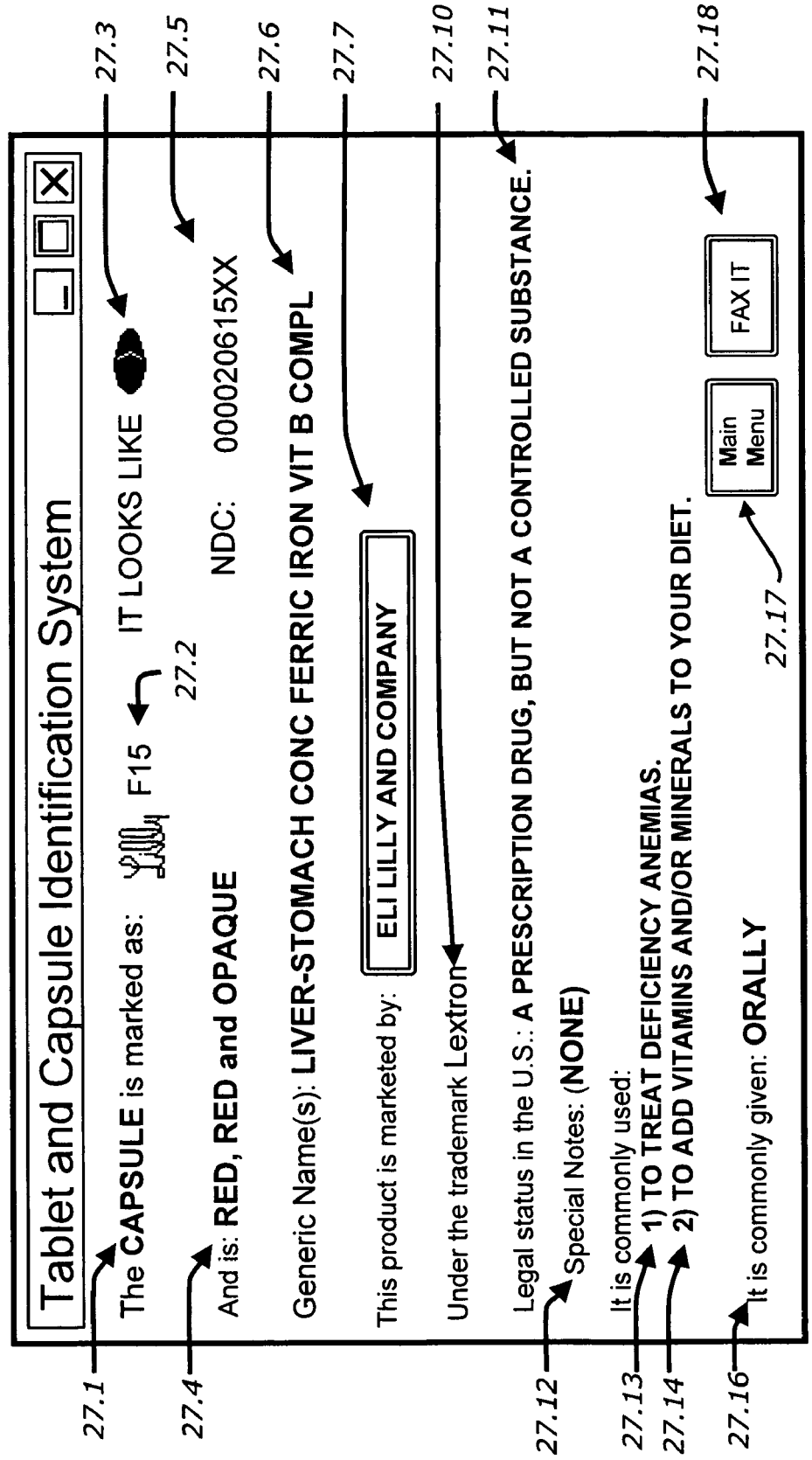
FIG. 27 is a screen shot illustrating a Result screen accessed by designating the next user option of FIG. 26 and includes the dosage form descriptor within the display (The capsule is marked as) followed by an imprint recap display including the graphic of the logo feature reconfirming positively the imprint on the dosage form for which the current inquiry is made, a graphical display of the capsule shape (It looks like field), a physical description display (red/red and opaque), a NDC display, a generic name(s) display, a drug manufacturer's name display and user option (This product is marketed by), the manufacturer's trademark display (Under the trademark), a legal status in the US display, a special notes display, it is commonly used display, it is commonly given display, a main menu user option and a fax it user option.

FIG. 27 illustrates a Result screen 27.0 accessed by designating next user option 26.2 of FIG. 26. This screen presents the results of various correlations of data inputs based hierarchically upon routines and systems of the present invention. The capsule is marked as display 27.1 confirms that the dosage form of interest is a capsule, followed by the imprint recap display 27.2 which presents the logo component class member graphically and remainder of the code component class member as text. It looks like display 27.3 indicates that a graphical representation of its physical appearance. The description display 27.4 indicates descriptors that the capsule is red/red and opaque. The NDC display 27.5 indicates an NDC number of 000020615XX, confirming the selection in screen 26.0 of FIG. 26. The generic name(s) display 27.6 indicates that the generic name of the tablet is Liver-Stomach Conc Ferric Iron Vit B Compl. This product is marketed by display and user option 27.7 indicates that the capsule is marketed by Eli Lilly and Company. The display and user option 27.7 may be clicked by a cursor position device so that more information regarding the marketer can be supplied on a separate screen 28.0, FIG. 28. Under the trademark display 27.10 indicates that the tablet has a trademark of Lextron™. Legal status in the US display 27.11 indicates that the tablet is a prescription drug, but not a controlled substance. The special notes display 27.12 provides no special notes for this drug product at this time. It is commonly used display indicates that the capsule is used to treat deficiency anemia 27.13 and to add vitamins and/or minerals to your diet 27.14. The route of administration display (It is commonly given orally) 27.16 specifies that the drug product is taken orally. Screen 27.0 also includes a return to main menu user option 27.17 and a fax it user option 27.18 which can provide a hard copy of screen 27.0 to an electronic printer or facsimile device.

It is appreciated that the presentation of Result screens 7.0, 12.0, 17.0, 21.0, 24.0 and 27.0 in the exemplary computer program vary one from other as the system and routines of the present invention accommodate the applicable data fields recorded for the designated drug product while avoiding the inclusion and confusion of blank data fields on the screen. The screen composed of systematically selected data fields are intended to be a custom report as nearly readable as possible by laity whose use of the resulting pharmaceutical and medical information is intended.

In the present invention the user may further access information about a drug maker by designating display and user options 7.7, 12.7, 17.7, 21.7, 21.10, 24.7 24.10, and 27.7 in the several Results screens 7.0, 12.0, 17.0, 21.0, 24.0 or 27.0; the present configuration limits, in no way, the subsequent addition of display and user options in the above screens or in the graphical user interface of FIG. 2, in future renditions of the invention. Presently, by actuating appropriate display and user options in the above respective screens, with a mouse or other cursor-positioning device, the user arrives at screen 28.0 of FIG. 28.

FIG. 28 illustrates a company information screen 28.0 accessed by designating display and user options in the Results screens enumerated above. The screen shown in FIG. 28 is exemplary and can include more or less information than that provided. In this example, company identifier 28.1 identifies the company as Hyrex Pharmaceuticals. The division identifier 28.2 qualifies the company address and specifies Hyrex with a corporate address. The address identifier 28.3 identifies the company address as 3494 Democrat Road. The P.O. Box identifier 28.4 gives the P.O. Box number as 18385. The city identifier 28.5 gives the city as Memphis. The state identifier 28.6 gives the state as Tennessee. The zip code identifier 28.7 gives the zip code as 38181-0385. The country identifier 28.8 gives the United States. The phone number displays 28.9 through 28.13 give the general phone number of the company as well as after hours, medical, consumer and fax phone numbers as applicable. Screen 28.0 also includes a close user option 28.14. The present configuration limits in no way the subsequent addition of user options or displays to the above routines in future renditions of the invention.

It is appreciated that the method, routines and system of the present invention utilize the various component classes described above. Generally, at least one of the component classes is selected from the group consisting of a logo class, a numeric class, an alphabetical class and a remainder of the code class. In order to provide for a failsafe feature and to minimize the risk of an incorrect identification, the routine includes the option of confirming one or more special descriptors of the identified imprint, from the physical characteristics of the drug product. The special descriptor is selected from the group consisting of a color descriptor, an opacity descriptor, a scoring descriptor, a shape descriptor, a generic name descriptor, a brand name descriptor, a drug maker descriptor, a strength descriptor, a dosage form descriptor, and a route of administration descriptor. It is appreciated that other special descriptors can also be used as are known in the art.

In one variant of the invention, the special dosage form can be scanned using a scanner. The data from the scanned image is then digitized and compared to one of the descriptors described above.

In a further variant of the invention, the method includes accessing the database described above using a computer network. The computer network comprises a wireless computer network using computer network enabled cell phones, PDA's or other electronic devices. The user can then pay for the imprint identification over the computer network. Various computer networks are used in the invention including a publicly accessible computer network and a privately accessible computer network. In one variant, the Internet is used.

The routines, system, devices and computer network of the present invention use a computer program for identifying an imprint of a dosage form. The program includes a routine for a searching an applicable database having a plurality of component classes and component class members therein; a routine for partitioning the imprint into at least one of the component classes; and a routine for matching at least one of the component class members within the plurality of component classes to obtain an identified imprint.

It is appreciated that a user accesses various screens by designating a selected user option with a keyboard or other cursor positioning device using a graphic terminal device. FIG. 29, Personal Computer, illustrates one embodiment of a computer 29.1 used in the system and routines 1.1 through 1.9 shown in Flowchart, FIG. 1. As shown in FIG. 29, computer 29.1 preferably includes graphic terminal device 29.2 equipped with conventional hardware, including central processing unit (CPU) 29.3, random access memory (RAM) 29.4, display memory 29.5, video interface circuit (VIC) 29.6, input/output controller (I/O) 29.7, data storage device (disk) 29.8, input device 29.9, display 29.10, external device 29.11, and optional network interface 29.12 which provides access to the Internet via an Internet service provider (ISP). Graphic terminal device 29.2 basically functions as a conventional data processor.

As shown in FIG. 29, CPU 29.3 is directly coupled to each of the other elements of graphic terminal device 29.2. CPU 29.3 executes program code (not shown) stored in one or more RAM 29.4 or disk 29.8 to carry out the functions and acts described in connection with graphic terminal device 29.2. CPU 29.3 preferably comprises at least one high-speed digital data processor adequate to execute program modules consistent with the invention, such as accumulation of data on dosage forms, transmission of such data and the processing of programs for identification of dosage forms. The processes performed by these modules are described in connection with FIGS. 2 through 28. CPU 29.3 interacts with RAM 29.4 and disk 29.8 to execute stored program code according to conventional data processing techniques.

As also shown in FIG. 29, input device 29.9 permits graphic terminal device 29.2 to receive information about dosage forms and, although shown as a single device, may comprise one or more data input devices of various types, such as a cursive pointing device, an alphanumeric keyboard, a numeric keypad, a bar code scanner, a credit card reader, a disk drive, a memory, an electronic communication line, and a wireless transceiver. Input device 29.9 preferably transmits received information to CPU 29.3 for storage in disk 29.8. VIC 29.6 comprises a video driver sending signals to display 29.10 displaying both text and graphics based on the contents of display memory 29.5. Display 29.10 is preferably large enough to display information relating to dosage forms. External device 29.11 allows operability of other components with computer, such as, for example, a modem, a printer, a scanner, a photocopying device, or any other form of input or output device. Optional network interface 29.12 links CPU 29.3 to allow communication with other collector devices, such as multiple collector graphic terminal devices, as seen in FIG. 30.

As shown in FIG. 29, disk 29.8 preferably comprises a large capacity memory capable of maintaining file database 29.13. File database 29.13 contains data pertaining to dosage forms. The contents of file database 29.13 are transmitted to CPU 29.3 for processing. For updating the file database 29.13, an electronic data interface (EDI) 29.14 is used. Electronic Data Interface 29.14 contains the disbursement information from file database 29.13. Data contained in one or more of these Drug Product Records and Relational Records databases may be periodically updated via input device 29.9, external device 29.11, or optional network interface 29.12. Samples of records, and their respective fields contained in, are shown in and described in connection with FIGS. 32 and 33.

As illustrated in FIG. 30, Modalities of Data Distribution via Network, the invention includes systems 30.1 through 30.13 for accessing, storing, compiling and transferring the information described herein by way of a web network of interconnected computer networks 30.1 or by way of intranet 30.2. In one embodiment, the web of interconnected computer networks is connected to the Internet 30.3. The systems 30.1 through 30.13 include servers 30.4 communicatively linked to a plurality of data packet receiving personal computers 30.5, workstations 30.6 and PDA 30.7 or other graphic terminal devices by way of data packet transferring communication links 30.8, 30.9, 30.10 and 30.11. The use of other communication links is also contemplated herein. Data packet transferring servers 30.4 provide to the personal computers 30.5 or workstations 30.6 a data packet based graphical user interface for introducing and navigating throughout the knowledge based systems 30.1 through 30.13.

Network 30.1 may comprise local area networks, metropolitan area networks, and wide area networks. Network 30.1 connects computers of organizations and individuals globally. The networks that comprise networks 30.1 are communicatively linked together by way of data packet transferring communication links, e.g., 30.8, 30.9, 30.10, and 30.11, or other communication links. These communication links further may include a router 30.12 and a firewall 30.13. These data packet transferring communication links and others described herein comprise, by way of example, dialup phone lines, high-speed dedicated leased lines, satellites, fiber optic communication links, microwave communication links, and/or wireless satellite communication links and combinations thereof. Network 30.1 communicatively connects computers nationally and/or globally in another variant. The data packet receiving computers on network 30.1 communicates using a variety of known protocols such as HTML.

The systems 30.1 through 30.13 have a data packet based graphical user interface that optionally provides cross-referenced and hypertext links to other information sources and files. These files are all interrelated and accessed on an as needed or as designated basis utilizing various routines.

The system also provides expository presentation of prerequisite and support information in data files, includes a communication link to a data packet transferred on-line support, and "when, as, and if" information and support. Based upon user data input and user option designation the routines automatically access screens and supplemental user options that tailor the user's particular expertise with the data screens and cross-reference and hypertext link with appropriate dosage form information.

The systems 30.1 through 30.13 also include practice area files that provide the opportunity to become familiar with drug concepts and terminology, and provide the opportunity to use the knowledge gained through use of the systems 30.1 through 30.13. The graphical user interface of systems 30.1 through 30.13 is truly multi-media and includes sound files, video files, graphics files, in black and white or color in another variant of the invention.

The screens, user options, files and routines herein embody a multiple-target audience approach. Separate, but related and cross-linked, screens, user options, files and routines are provided for different areas of user needs. These users include practitioners, law enforcement, students and members of the general public. Each respective user need, in one variant of the invention, has an appropriate user option, screen and file associated or correlated therewith.

In another variant, the invention includes a data packet transferring network and a computer readable medium. The computer readable medium includes at least one of a floppy disk, a magnetic tape, a CD-ROM, and a hard drive.

It is further appreciated that various method steps described herein can be added or deleted without departing from the spirit and scope of the invention.

The database in use can be built one record at a time and can include upwards of about 50,000 records. The database can be continually in an update mode, adding (never deleting in one variant of the invention) records on a daily basis. Each record is documented and signed off by a pharmacist. More than 1600 drug firms are cataloged and routinely contacted (at varying time intervals) for update information.

Users inquire daily into the identification of tablets and capsules, referred by several sources throughout the U.S. Since no distributor or major generic drug maker makes all of their catalog items at any one point in time, their product lists, catalogs and identification lists are rich sources of information beyond the specific manufacturer's line itself. The appearance in a distributor's catalog of a heretofore unknown imprint or drug maker provides a clue for contact and inclusion of an entire new product line.

The database described herein, in one variant, is unique in that it has cataloged more than 200 logo graphics. Logo graphics are non-alphabetic, non-numeric features found on tablets and capsules. The collection is comprehensive for drug products in the U.S. The comprehensive logo collection also identifies the situation where new logos are appearing on products in the marketplace. Imprints when taken with color, shape and scoring definitively and fully identify drug products—their maker and the drug, their strength, type of formulation and route of administration.

It is appreciated that the method of the present invention broadly includes: (a) assessing imprints, (b) partitioning the features in imprints of dosage forms into components, (c) assigning each component to only one of at least four (4) searchable classes, (d) further assigning a numerical value to non-numeric, non-alphabetic components found in features of imprints, (e) maintaining the relationship among class and components of an applicable database and (f) exhausting all imprints in the US market. The methodology then is programmed using computer technology. The use of the resulting search routine together with an appropriate database of component class members derived from imprints features leads to unique solutions and confidence in the results and provides a 98% probability of discovering the identity of the product bearing the imprint. Imprints on drug products are unique in the U.S.

The invention provides a computer program for identifying an imprint of a dosage form. The computer program includes a routine for searching a database having a plurality of component classes. Each of the component classes includes a plurality of component class members. Component classes comprise a respective type of feature of a plurality of imprints. The program also includes a matching routine for matching a feature of the imprint to at least one of the component class members to obtain an identified imprint.

This is an exemplary way to construct one variant of the program of the invention. Imprints appear to be made up of a company logo, numbers or letter(s) feature and/or a feature using numbers or letters to designate the company's product. As a result, three primary routines and a routine for those remaining features that do not fit this rule are provided in the program:

a) look up by logo, e.g., lavender, oval tablet with Abbott Laboratories logo (103) and NS,
b) look up numerically, e.g., white, round, unscored tablet bearing 93 and 150/3,
c) look up alphabetically, e.g., white, round tablet marked BRA 200, and
d) none of the above (Remainder), e.g., 230 (note that 230 is not found in NUMERIC CODES, FIGS. 8 and 9).

In the above referenced examples, the features of the imprint that identify the maker or distributor are the Abbott Laboratories logo (103), 93 or BRA. The remaining feature of the imprint identifies the product; examples from above respectively are NS, 150/3 and 200. The remainder of the code routine accommodates the imprints that only have a product feature in the imprint, e.g., 230. This fourth routine also contains component class members of imprint features which specifically are composed of the product name itself, e.g., A2A/ALKERAN. By placing these otherwise obvious imprint features here, precision and efficiency of the alphabetic routine improves and is a further sophistication of method benefiting search routines in the present invention.

The following terms are used to describe products and are commonly used by pharmacists and the public. A tablet is a hard dosage form, varying in color, shape and scoring. A capsule is a two-piece dosage form, possibly varying in color of the two halves (body and cap) and opacity (clear or opaque) which determines if its contents can be seen through the gelatin. A softgel is a liquid-filled dosage form, varying in color, shape and opacity. A geltab is a tablet with a gelatin coat, is round and varies in color. A gelcap is a tablet with a gelatin coat or a tablet within a capsule, is oblong, is typically opaque and varies in color. A caplet is a tablet that is oblong and made to swallow as easily as a capsule. A score is the indentation in a tablet that permits it to be broken easily and multiple scores may be present. The term clear means that an observer can see through the gelatin of the capsule or softgel. The term opaque means that an observer cannot see through the gelatin of the capsule or softgel; tablets, geltabs and gelcaps are always opaque.

It is appreciated that an imprint may relate to multiple National Drug Codes but for each NDC a single imprint exists. The imprint identifies a specific drug product by descriptors, no matter which company distributes it by whichever NDC. But for a specific NDC, identified to a specific distributor, only one imprint exists. This latter fact makes it possible to print on the prescription container label the imprint and color, shape and scoring descriptors of the drug product dispensed by its NDC. This provides an innovative means of reducing dispensing errors by pharmacists and to elicit the cooperation of the patient to the same end.

EXAMPLES

The following examples are provided to illustrate the ease of the routines to make an ID. A comment provides the various considerations that are used in the method and routines of the present invention to arrive at a positive identification of an unknown product of interest. FIG. 31 presents graphical images of four exemplary imprints.

Example 1

Identify a lavender, oval tablet marked with 'a funny, little, printed a' and NS. Start with a click on Imprint on tablet/capsule user option 2.7 (FIG. 2), double click on Abbott Laboratories logo 3.8 (103 in top row of logo component class members, screen 3.0), scroll down the list in screen 5.0, FIG. 5 (NS is but one of many Abbott remainder of the codes in this screen) and double click on NS. See PICK IMPRINT screen 6.0 of FIG. 6, double click on descriptor and see RESULT screen 7.0, FIG. 7, describing the product. To return to main screen, click on MAIN user option. Comment: the remainder of the code NS may be read by the observer as SN, since the two alphabetic characters have concurrence in two directions and the accompanying Abbott Laboratories logo is not intuitively obvious regarding its proper perspective. Observe that Remainder of the code list in screen 5.0 does not include SN, obviating a possible ID in error. Also only four 'clicks' in the exemplary computer programs result in a declarative identification of the drug product.

Example 2

Identify a white, round, unscored tablet marked 93/150 and 3 on the obverse. Start with a click on imprint on tablet/capsule user option 2.7 (FIG. 2). At LOGO screen 3.0 click NEXT user option and see NUMERIC CODES screen, FIG. 8. Pull down the slide bar to find 93 as viewed in screen 9.0, FIG. 9, double click on 93 and see IMPRINT REMAINDER screen, FIG. 10. Pull down the slide bar to find 150/3; double click on it (150/3 is one of many Teva remainder of the codes). See Pick Imprint screen, FIG. 11 and double click on a descriptor and see RESULT screen describing the product, FIG. 12. To return to main screen, click on MAIN user option. Comment: five clicks of the cursor-positioning device make a positive identification.

Example 3

Identify a white, oval, scored tablet marked BRA 200. Start with a click on Imprint on tablet/capsule user option 2.7 (FIG. 2); at each of the LOGOS and NUMERIC CODES screens, FIGS. 3 and 8, click on NEXT user option and then see ALPHA CODES screen, FIG. 13. Pull down the slide bar to find BRA as seen in FIG. 14. Double click on BRA, see IMPRINT REMAINDER screen, FIG. 15, come up and double click on 200. See PICK IMPRINT screen, FIG. 16 and double click on the descriptor to see RESULT screen, FIG. 17. Click MAIN user option to return. Comment: six clicks make a positive ID.

Example 4

Identify a yellow, round coated tablet marked only with the imprint 230. Start with a click on imprint on tablet/capsule user option 2.7 in FIG. 2; at each of the LOGOS, NUMBER and ALPHA CODES screens click on NEXT user option and wait for the program to sort the database excluding all the codes implicit in the three screens passed by. See IMPRINT REMAINDER screen in FIG. 18 and put the cursor in the input field below REMAINDER OF the CODE, type 230 and then click on NEXT. In the PICK IMPRINT screen in FIG. 20, double click a descriptor. See RESULT screen which describes the product; to return to main screen, click on MAIN user option. Comment: as in this example, some imprints do not have a primary logo, numeric or alphabetic component class member but ONLY the tertiary remainder of the code component class member which designates a product with no clue to its maker (note that 230 is not found in numeric component class, not shown). The fourth and last alliteration of the search routine is not remainders of the code per se, but a tertiary subset of components unto itself.

Example 5

Identify a pink, round and scored tablet marked LO17. Start with a click on Imprint on tablet/capsule user option 2.7, FIG. 2; at each of the LOGOS and NUMERIC CODES screens click on NEXT and see ALPHA CODES screen (analogous to the screen in FIG. 13). Pull down the slide bar to find LO; no LO is found in the scrollable alpha codes list (nothing bears the alphabetic characters LO as an imprint). Scroll to L and double click on L in the same list. Now double click on 017 in the IMPRINT REMAINDER screen (analogous to the screen in FIG. 15) and see the PICK IMPRINT screen (analogous to the screen in FIG. 16) in which two products, not identical in physical appearance, bear the same imprint (not shown). Double click on the product that matches the physical description of the tablet you are searching for, in the descriptor field and see RESULT screen describing the product. To return to main screen, click MAIN user option. Comment: the SPECIAL NOTE "Imprint on several different products; COMPARE dosage form, color and shape" appears. The means of differentiating duplicate imprints, for the few that exist, are in the present invention a fail-safe attribute of the routines.

Example 6

Identify a yellow, round, unscored tablet with "a Bull with a Ball on its Head," as an imprint. Start with a click on Imprint on tablet/capsule 2.7, FIG. 2 and double click Logo number 266 in the LOGO screen (not shown). See the IMPRINT REMAINDER screen (analogous to the screen in FIG. 5) and click on NEXT user option, since no remainder of the code is associated with the logo component class member, to arrive at the PICK IMPRINT screen. In the PICK IMPRINT screen (analogous to the screen in FIG. 6), click on each of the descriptors and note that the imprint does not change. Double click on the descriptor for "yellow, round, unscored tablet" and now you will see the RESULT screen (analogous to the screen in FIG. 7), describing the product and the SPECIAL NOTE "Imprint on products with same active ingredient but check for different strengths." To return to the main screen, click on the MAIN user option. Comment: in this example, three tablets of varying strengths for the same active ingredient have the same imprint but differ in color. Color along with the right primary logo component class member makes the identification.

Example 7

Identify a pink, round tablet which is scored in two directions with an imprint of two capital letters C in a rectangle followed by 105. Start with a click on Imprint on tablet/capsule 2.7, FIG. 2 and double click on Logo number 179 (not shown). See the IMPRINT REMAINDER screen (analogous to the screen in FIG. 5) and scroll down to remainder of the code 105 and double click on it. In the PICK IMPRINT screen (analogous to the screen in FIG. 6), double click on the record having the right color and now see RESULT screen describing the product and the SPECIAL NOTE "Imprint on products with same ingredient; CHECK for color." To return to main screen, click on MAIN user option. Comment: in this example, the manufacturer makes varying colored tablets, all containing the same drug and strength and bearing the same imprint.

The specificity of imprints makes it possible to identify immediately, accurately, reliably and inexpensively a dosage form. In a minority of cases, far less than 1 in a thousand, the imprint must be used in conjunction with a physical descriptor, as seen in examples 5, 6 and 7 above, to arrive at a positive identification. The imprint is the only reliable means of making an ID, alone or in conjunction with physical descriptors and order makes the difference—assess imprint first and then descriptor. The reliability is sufficient to be used by poison centers, pharmacists and forensic laboratories and certain jurisdictions as probable cause in drug cases.

Lastly, being able via the Web to match an imprint on a tablet or capsule to the graphics of a database with a searchable format is a technological break-through. A positive identification is as few as four (Example 1 above), sometimes six, clicks away for both laity and professionals, whether familiar or unfamiliar with medical and pharmaceutical jargon, using the present invention. Such a resource has major public health implications.

While only a few, preferred embodiments of the invention have been described herein above, those of ordinary skill in the art will recognize that the embodiment may be modified and altered without departing from the central spirit and scope of the invention. Thus, the preferred embodiment herein above is to be considered in all respects as illustrative and not restrictive.

We claim:

1. A computer implemented method of identifying a dosage form by identifying an imprint on the dosage form, comprising:
   a) creating a database by:
      i) partitioning a plurality of features of imprints into a plurality of respective component classes, wherein said features comprise logo characters, numeric characters, alphabetical characters, and remainder characters;
      ii) assigning imprint features to mutually exclusive classes, wherein said classes comprise a logo class, a numeric class, an alphabetical class, and a remainder of the code class;
      (iii) requiring a relationship to be maintained between components within classes and the respective set of imprint features; and
   b) matching said imprint to at least one of said component class members to obtain an identified imprint.

2. The method of claim 1 in which said dosage form is selected from at least one of said group comprising of a tablet, a capsule, a softgel, a lozenge, an implant, an insert, a geltab, and a gelcap.

3. The method of claim 1 further comprising a special descriptor to confirm the identity of said imprint.

4. The method of claim 3 in which said special descriptor is selected from at least one of the group consisting of a color descriptor, an opacity descriptor, a scoring descriptor, a shape descriptor, a drug descriptor, a strength descriptor, a dosage descriptor, and a route of administration descriptor.

5. The method of claim 1 further comprising accessing said database using a computer network.

6. The method of claim 5 in which said computer network comprises a wireless computer network.

7. The method of claim 5 further comprising paying for said identification of an imprint of a dosage form over said computer network.

8. The method of claim 7 further comprising paying for identifying an imprint of a dosage form over a publicly accessible telephone network.

9. The method of claim 5 in which said computer network is selected from the group consisting of a publicly accessible computer network and a privately accessible computer network.

10. The method of claim 9 in which said publicly accessible computer network comprises the Internet.

11. The method of claim 1 in which a recognized dosage form is substance suitable for human or animal ingestion.

12. The method of claim 1 in which a recognized dosage form is a confectionery product.

13. A computer implemented method of identifying a dosage form by identifying an imprint on the dosage form, comprising:
   a) creating a database by:
      i) partitioning a plurality of features of imprints into a plurality of respective component classes, wherein said features comprise logo characters, numeric characters, and alphabetical characters;
      ii) assigning imprint features to mutually exclusive classes, wherein said classes comprise a logo class, a numeric class, and an alphabetical class;
      iii) requiring a relationship to be maintained between components within classes and the respective set of imprint features; and
   b) matching said imprint to at least one of said component class members to obtain an identified imprint.

14. The method of claim 13 further comprising a component class wherein said component class comprises a remainder of the code class.

15. The method of claim 13 further comprising a special descriptor to confirm the identity of said imprint.

16. The method of claim 15 in which said special descriptor is selected from at least one of the group consisting of a color descriptor, an opacity descriptor, a scoring descriptor, a shape descriptor, a drug descriptor, a strength descriptor, a dosage descriptor, and a route of administration descriptor.

17. A computer implemented method of identifying a dosage form by identifying an imprint on the dosage form, comprising:
   a) partitioning said imprints into a plurality of mutually exclusive feature types, including primary, secondary and tertiary features,
   b) assigning said imprint features to a database as components in a plurality of mutually exclusive classes,
      i) placing said primary features respectively into logo, numeric and alphabetic classes, and
      ii) placing said secondary and tertiary features into a remainder code class,
   c) identifying a graphical expression of each logo feature as a logo graphic,
   d) assigning a unique number to each logo graphic within the logo class, and
   e) requiring that a specified a relationship be maintained between components within classes and the respective set of imprint descriptors, in the records of any applicable database comprising imprint feature types.

18. A computer implemented method of identifying a dosage form by an imprint on the dosage form, where the user selects features of an imprint from classes presented through a graphical user interface, comprising:
   a) dividing an imprint into features comprising, logos, numbers, and letters;
   b) creating a data set of logo features as electronic drawings;
   c) assigning said imprint features to a database as components in a plurality of mutually exclusive classes, including logo, number and letter classes;
   d) requiring that a specified relationship be maintained between components within classes;
   e) identifying an imprint by a user-interactive routine, comprising
      i) presenting classes of logo, number and letter imprint features;
      ii) excluding features within each class from further consideration that have no specified relationship with the feature that the user selects;
      iii) matching said imprint to at least one of said component class members to obtain an identified imprint.

* * * * *